(12) United States Patent
Zhang et al.

(10) Patent No.: US 6,699,855 B2
(45) Date of Patent: Mar. 2, 2004

(54) INHIBITORS OF HEPATITIS C VIRUS NS3 PROTEASE

(75) Inventors: Xiaojun Zhang, Hockessin, DE (US); Wei Han, Newark, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/795,410

(22) Filed: Feb. 28, 2001

(65) Prior Publication Data

US 2002/0065248 A1 May 30, 2002

Related U.S. Application Data

(60) Provisional application No. 60/185,618, filed on Feb. 29, 2000.

(51) Int. Cl.$^7$ .................. A61K 31/55; A61K 31/495; C07D 223/00; C07D 251/00; C07F 7/02
(52) U.S. Cl. .............. 514/214.02; 514/7; 514/64; 514/80; 514/85; 514/249; 514/250; 540/541; 540/542; 540/579; 544/183; 544/214; 544/229; 544/337; 544/349; 544/350; 260/1 T
(58) Field of Search ................ 514/7, 64, 80, 514/85, 214.02, 250, 249; 540/541, 542, 579; 544/337, 350, 349, 229, 183, 214; 260/1 T

(56) References Cited

U.S. PATENT DOCUMENTS

6,277,851 B1 * 8/2001 De Nanteuil et al. ....... 514/249

FOREIGN PATENT DOCUMENTS

| WO | WO98/17679 | 4/1998 |
|---|---|---|
| WO | WO99/64442 | 12/1999 |

OTHER PUBLICATIONS

Poynard, T., et. al., Lancet 352; 1426–1432 (1998).
The Peptides, vol. 3; 3–88 (1981).
Yoshifugi, S., et. al., Chem. Pharma. Bull. 34; 3873–3878 (1986).
Fukuyama. T., et. al., J. Am. Chem. Soc. 112; 7050–7051 (1990).
Matteson, D. S., et. al., Organometallics, 3; 1284–1288 (1984).
B. Tao, et. al., Tetrahedron Lett., 39; 2507–2510 (1998).
Edwards, P. D., et. al., Medicinal Res. Reviews, 14; 127–194 (1994).
Skiles, J. W., et. al., J. Med. Chem., 35; 641–662 (1992).
Ogilvie, W., et. al., J. Med. Chem., 40; 4113–4135 (1997).
Poupart, M. A., et. al., J. Org. Chem., 64; 1356–1361 (1999).
Veale, C. Z., et. al., J. Med. Chem., 40; 3173–3181 (1997).
Wolfe, M. S., et. al., J. Med. Chem., 41; 6–9 (1998).
Scheidt, K. A., et. al., Bioorg. Med. Chem., 6; 2477–2494 (1998).
Carpino, et. al., J. Chem. Soc. Chem. Commun., 201–203 (1994).
D. Dess, et. al., J. Org. Chem., 48; 4155–4156 (1983).
Young, et. al., Antimicrobial Agents and Chemotherapy, 2602–2605 (1995).
Still, W. C., et. al., J. Orgn. Chem., 43; 2923 (1978).
Steinkuhler, C., et. al., Journal of Virology, 70; 6694–6700, 1996.
Steinkuhler, C., et. al., Journal of Biological Chemistry, 271; 6367–6373 (1996).
Taliana, et. al., Anal. Biochem., 240; 60–67 (1996).
Andrew S. Thompson, et. al., Tet. Lett., 36; 8937–8940 (1995).
Sharpless, K. B., et. al., Angew. Chem. Int. Ed. Engl. 35; 2813 (1996).
Suzuki, et. al., Chem. Rev. 95; 2457–2483 (1995).
N. P., et. al., Tetrahedron Lett. Peet., 3433–3436 (1988).

\* cited by examiner

*Primary Examiner*—Mukund J. Shah
*Assistant Examiner*—Tamthom N. Truong
(74) *Attorney, Agent, or Firm*—James Epperson; Scott K. Larsen; Louis A. Piccone

(57) ABSTRACT

The present invention relates to compounds of Formula (I):

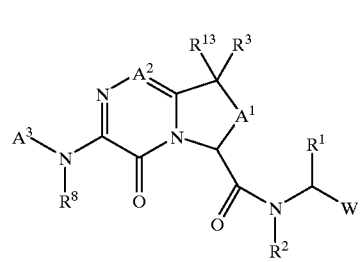

(I)

wherein $A^1$ is methylene, ethylene or propylene group and $A^2$ is N or $CR^5$, or stereoisomeric forms, stereoisomeric mixtures, or pharmaceutically acceptable salt forms thereof, which are useful as inhibitors of HCV NS3 protease, and to pharmaceutical compositions and diagnostic kits comprising the same, and methods of using the same for treating viral infection or as an assay standard or reagent.

10 Claims, No Drawings

US 6,699,855 B2

INHIBITORS OF HEPATITIS C VIRUS NS3 PROTEASE

This application claims the benefit of U.S. Provisional Application No. 60/185,618, filed Feb. 29, 2000.

FIELD OF THE INVENTION

The present invention relates generally to a novel class of pyrrolopyrazinones which are useful as serine protease inhibitors, and more particularly as Hepatitis C virus NS3 protease inhibitors. This invention also relates to pharmaceutical compositions comprising these compounds and methods of using the same.

BACKGROUND OF THE INVENTION

Hepatitis C virus (HCV) is the major cause of transfusion and community-acquired non-A, non-B hepatitis worldwide. Approximately 2% of the world's population are infected with the virus. In the Unites States, hepatitis C represents approximately 20% of cases of acute hepatitis. Unfortunately, self-limited hepatitis is not the most common course of acute HCV infection. In the majority of patients, symptoms of acute hepatitis resolve, but alanine aminotransferase (a liver enzyme diagnostic for liver damage) levels often remain elevated and HCV RNA persists. Indeed, a propensity to chroninicity is the most distinguishing characteristic of hepatitis C, occurring in at least 85% of patients with acute HCV infection. The factors that lead to chronicity in hepatitis C are not well defined. Chronic HCV infection is associated with increased incidence of liver cirrhosis and liver cancer. No vaccines are available for this virus, and current treatment is restricted to the use of alpha interferon, which is effective in only 15–20% of patients. Recent clinical studies have shown that combination therapy of alpha interferon and ribavirin leads to sustained efficacy in 40% of patients (Poynard, T. et al. *Lancet* 1998, 352, 1426–1432.). However, a majority of patients still either fail to respond or relapse after completion of therapy. Thus, there is a clear need to develop more effective therapeutics for treatment of HCV-associated hepatitis.

HCV is a positive-stranded RNA virus. Based on comparison of deduced amino acid sequence and the extensive similarity in the 5' untranslated region, HCV has been classified as a separate genus in the Flaviviridae family, which also includes flaviviruses such as yellow fever virus and animal pestiviruses like bovine viral diarrhea virus and swine fever virus. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. As was determined by transient expression of cloned HCV cDNAs, the precursor protein is cotranslationally and posttranslationally processed into at least 10 viral structural and nonstructural (NS) proteins by the action of a host signal peptidase and by two distinct viral proteinase activities. The translated product contains the following proteins: core-E1-E2-p7-NS2-NS3-NS4A-NS4B-NS5A-NS5B.

The N-terminal portion of NS3 functions as a proteolytic enzyme that is responsible for the cleavage of sites liberating the nonstructural proteins NS4A, NS4B, NS5A, and NS5B. NS3 has further been shown to be a serine protease. Although the functions of the NS proteins are not completely defined, it is known that NS4A is a protease cofactor and NS5B is an RNA polymerase involved in viral replication. Thus agents that inhibit NS3 proteolytic processing of the viral polyprotein are expected to have antiviral activity.

There are several patents which disclose HCV NS3 protease inhibitors. WO98/17679 describes peptide and peptidomimetic inhibitors with the following formula: U—$E^8$—$E^7$-$E^6$-$E^5$-$E^4$-NH—CH(CH$_2$G$^1$)-W1, where W is one of a variety of electrophilic groups, including boronic acid or ester. E4 represents either an amino acid or one of a series of peptidomimetic groups, the sythesis of which are not exemplified. HCV protease inhibitors described in the present case are not covered.

Based on the large number of persons currently infected with HCV and the limited treatments available, it is desirable to discover new inhibitors of HCV NS3 protease.

SUMMARY OF THE INVENTION

Accordingly, one object of the present invention is to provide novel HCV NS3 protease inhibitors.

It is another object of the present invention to provide a novel method of treating HCV infection which comprises administering to a host in need of such treatment a therapeutically effective amount of at least one of the compounds of the present invention or a pharmaceutically acceptable salt form thereof.

It is another object of the present invention to provide pharmaceutical compositions with HCV NS3 protease inhibiting activity comprising a pharmaceutically acceptable carrier and a therapeutically effective amount of at least one of the compounds of the present invention or a pharmaceutically acceptable salt form thereof. It is another object of the present invention to provide a method of inhibiting HCV present in a body fluid sample which comprises treating the body fluid sample with an effective amount of a compound of the present invention. It is another object of the present invention to provide a kit or container containing at least one of the compounds of the present invention in an amount effective for use as a standard or reagent in a test or assay for determining the ability of a potential pharmaceutical to inhibit HCV NS3 protease, HCV growth, or both.

It is another object of the present invention to provide novel compounds for use in therapy.

It is another object of the present invention to provide the use of novel compounds for the manufacture of a medicament for the treatment of HCV.

These and other objects, which will become apparent during the following detailed description, have been achieved by the inventors' discovery that compounds of Formula (I):

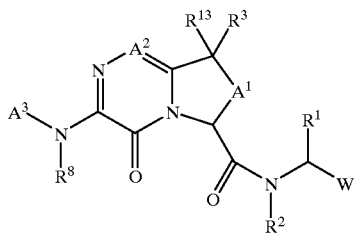

(I)

wherein W, $R^1$, $R^2$, $R^3$, $R^8$, $R^{13}$, $A^1$, $A^2$, and $A^3$ are defined below, stereoisomeric forms, mixtures of stereoisomeric forms, or pharmaceutically acceptable salt forms thereof, are effective HCV NS3 protease inhibitors.

DETAILED DESCRIPTION OF PREFERRED EMBODIMENTS

[1] Thus, in a first embodiment, the present invention provides a novel compound of Formula I:

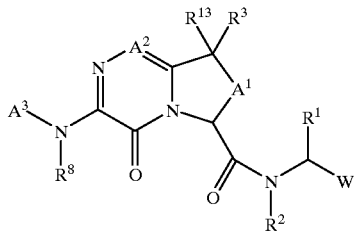

(I)

or a stereoisomer or pharmaceutically acceptable salt form thereof, wherein;

$A^1$ is —$CH_2$—, —$CH_2CH_2$—, or —$CH_2CH_2CH_2$—;
$A^2$ is —N= or —$CR^6$=;
$A^3$ is selected from —$R^9$, —$A^4$—$R^9$, —$A^4$—$A^5$—$R^9$, and —$A^4$—$A^5$—$A^6$—$R^9$;
W is selected from the group
  —$B(OR^{26})$ $(OR^{27})$,
  —$C(=O)C(=O)$—Q,
  —$C(=O)C(=O)NH$—Q,
  —$C(=O)C(=O)$—O—Q,
  —$C(=O)CF_2C(=O)NH$—Q,
  —$C(=O)CF_3$,
  —$C(=O)CF_2CF_3$,
  —$C(=O)H$,
  an amino acid residue,
  —$A^7$—$A^8$, and
  —$A^7$—$A^8$—$A^9$;
Q is selected from —$(CR^{10}R^{10c})_r$—$Q^1$, $(CR^{10}R^{10c})_r$—$Q^2$,
  $C_1$–$C_4$ alkyl substituted with $Q^1$,
  $C_2$–$C_4$ alkenyl substituted with $Q^1$,
  $C_2$–$C_4$ alkynyl substituted with $Q^1$,
  an amino acid residue,
  —$A^7$—$A^8$, and
  —$A^7$—$A^8$—$A^9$;
$Q^1$ is selected from
  —$CO_2R^{11}$, —$SO_2R^{11}$, —$SO_3R^{11}$, —$P(O)_2R^{11}$, —$P(O)_3R^{11}$,
  aryl substituted with 0–4 $Q^{1a}$,
  5–6 membered heterocyclic group consisting of carbon atoms and 1–4 heteroatoms selected from the group: O, S, and N, said heterocyclic group substituted with 0–4 $Q^{1a}$;
$Q^{1a}$ is H, F, Cl, Br, I, —$NO_2$, —CN, —NCS, —$CF_3$, —$OCF_3$, —$CH_3$, —$OCH_3$, —$CO_2R^{19}$, —$C(=O)NR^{19}R^{19}$, —$NHC(=O)R^{19}$, —$SO_2R^{19}$, —$SO_2NR^{19}R^{19}$, —$NR^{19}R^{19}$, —$OR^{19}$, —$SR^{19}$, $C_1$–$C_4$ alkyl, $C_1$–$C_4$ alkoxy, $C_1$–$C_4$ haloalkyl, $C_1$–$C_4$ haloalkoxy
alternatively, $NR^{19}R^{19}$ may form a 5–6 membered heterocyclic group consisting of carbon atoms, a nitrogen atom, and optionally a second heteroatom selected from the group:
  O, S, and N;
$Q^2$ is —X—$NR^{12}$—Z, —$NR^{12}$—Y—Z, or —X—$NR^{12}$—Y—Z;
X is selected from the group: —C(=O)—, —S—, —S(=O)—, —$S(=O)_2$—, —P(O)—, —$P(O)_2$—, and —$P(O)_3$—;
Y is selected from the group: —C(=O)—, —S—, —S(=O)—, —$S(=O)_2$—, —P(O)—, —$P(O)_2$—, and —$P(O)_3$—;
Z is $C_1$–$C_4$ haloalkyl,
  $C_1$–$C_4$ alkyl substituted with 0–3 $Z^a$,
  $C_2$–$C_4$ alkenyl substituted with 0–3 $Z^a$,
  $C_2$–$C_4$ alkynyl substituted with 0–3 $Z^a$,
  $C_3$–$C_{10}$ cycloalkyl substituted with 0–5 $Z^b$,
  $C_3$–$C_{10}$ carbocyle substituted with 0–5 $Z^b$,
  aryl substituted with 0–5 $Z^b$,
  5–10 membered heterocyclic group consisting of carbon atoms and 1–4 heteroatoms selected from the group: O, S, and N, said heterocyclic group substituted with 0–4 $Z^b$;
  an amino acid residue,
  —$A^7$—$A^8$, or
  —$A^7$—$A^8$—$A^9$;
$Z^a$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$, —$NR^{20}R^{20}$, —$OR^{20}$, —$SR^{20}$, —$S(=O)R^{20}$, —$SO_2R^{20}$, —$SO_2NR^{20}R^{20}$, $C_1$–$C_4$ alkyl, $C_1$–$C_4$ alkoxy, $C_1$–$C_4$ haloalkyl, $C_1$–$C_4$ haloalkoxy,
  $C_3$–$C_{10}$ cycloalkyl substituted with 0–5 $Z^b$,
  $C_3$–$C_{10}$ carbocyle substituted with 0–5 $Z^b$,
  aryl substituted with 0–5 $Z^b$, or
  5–10 membered heterocyclic group consisting of carbon atoms and 1–4 heteroatoms selected from the group: O, S, and N, said heterocyclic group substituted with 0–4 $Z^b$;
$Z^b$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$, —$NR^{20}R^{20}$, —$OR^{20}$, —$SR^{20}$, —$S(=O)R^{20}$, —$SO_2R^{20}$, —$SO_2NR^{20}R^{20}$, $C_{1-C4}$ alkyl, $C_1$–$C_4$ alkoxy, $C_1$–$C_4$ haloalkyl, $C_1$–$C_4$ haloalkoxy,
  $C_3$–$C_{10}$ cycloalkyl substituted with 0–5 $Z^c$,
  $C_3$–$C_{10}$ carbocyle substituted with 0–5 $Z^c$,
  aryl substituted with 0–5 $Z^c$, or
  5–10 membered heterocyclic group consisting of carbon atoms and 1–4 heteroatoms selected from the group: O, S, and N, said heterocyclic group substituted with 0–4 $Z^c$;
$Z^c$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$, —$NR^{20}R^{20}$, —$OR^{20}$, —$SR^{20}$, —$S(=O)R^{20}$, —$SO_2R^{20}$, —$SO_2NR^{20}R^{20}$, $C_1$–$C_4$ alkyl, $C_1$–$C_4$ alkoxy, $C_1$–$C_4$ haloalkyl, $C_1$–$C_4$ haloalkoxy;

alternatively, $NR^{20}R^{20}$ may form a 5–6 membered heterocyclic group consisting of carbon atoms, a nitrogen atom, and optionally a second heteroatom selected from the group:
O, S, and N;

$OR^{26}$ and $OR^{27}$ are independently selected from:
  a) —OH,
  b) —F,
  c) —$NR^{28}R^{29}$,
  d) $C_1$–$C_8$ alkoxy, or
when taken together, $OR^{26}$ and $OR^{27}$ form:
  e) a cyclic boron ester where said chain or ring contains from 2 to 20 carbon atoms, and, optionally, 1, 2, or 3 heteroatoms which can be N, S, or O,
  f) a cyclic boron amide where said chain or ring contains from 2 to 20 carbon atoms, and, optionally, 1, 2, or 3 heteroatoms which can be N, S, or O,
  g) a cyclic boron amide-ester where said chain or ring contains from 2 to 20 carbon atoms and, optionally, 1, 2, or 3 heteroatoms which can be N, S, or O;

$R^1$ is selected from the group: H, F,
  $C_1$–$C_6$ alkyl substituted with 0–3 $R^{1a}$,
  $C_2$–$C_6$ alkenyl substituted with 0–3 $R^{1a}$,
  $C_2$–$C_6$ alkynyl substituted with 0–3 $R^{1a}$,
  aryl substituted with 0–5 $R^{1a}$, and
  $C_3$–$C_6$ cycloalkyl substituted with 0–3 $R^{1a}$;

$R^{1a}$ is selected at each occurrence from the group:
  Cl, F, Br, I, $CF_3$, $CHF_2$, OH, =O, SH, —$CO_2R^{1b}$, —$SO_2R^{1b}$, —$SO_3R^{1b}$, —$P(O)_2R^{1b}$, —$P(O)_3R^{1b}$, —C(=O)$NHR^{1b}$, —NHC(=O)$R^{1b}$, —$SO_2NHR^{1b}$, —$OR^{1b}$, —$SR^{1b}$, $C_1$–$C_3$ alkyl, $C_3$–$C_6$ cycloalkyl, $C_1$–$C_6$ alkoxy, —S—($C_1$–$C_6$ alkyl),
  aryl substituted with 0–5 $R^{1c}$,
  —O—$(CH_2)_q$-aryl substituted with 0–5 $R^{1c}$,
  —S—$(CH_2)_q$-aryl substituted with 0–5 $R^{1c}$,
  5–10 membered heterocyclic group consisting of carbon atoms and 1–4 heteroatoms selected from the group:
  O, S, and N, and substituted with 0–3 $R^{1c}$;

$R^{1b}$ is H,
  $C_{1-C4}$ alkyl substituted with 0–3 $R^{1c}$,
  $C_2$–$C_4$ alkenyl substituted with 0–3 $R^{1c}$,
  $C_2$–$C_4$ alkynyl substituted with 0–3 $R^{1c}$,
  $C_3$–$C_6$ cycloalkyl substituted with 0–5 $R^{1c}$,
  $C_3$–$C_6$ carbocyle substituted with 0–5 $R^{1c}$,
  aryl substituted with 0–5 $R^{1c}$,
  5–6 membered heterocyclic group consisting of carbon atoms and 1–4 heteroatoms selected from the group:
  O, S, and N, said heterocyclic group substituted with 0–4 $R^{1c}$;

$R^{1c}$ is selected at each occurrence from the group:
  $C_1$–$C_4$ alkyl, Cl, F, Br, I, OH, $C_1$–$C_4$ alkoxy, —CN, —$NO_2$, —$OR^{1d}$, —(=O)$OR^{1d}$, —$NR^{1d}R^{1d}$, —$CF_3$, —$OCF_3$, and aryl substituted by 0–3 $R^{1e}$;

$R^{1d}$ is H, $C_1$–$C_4$ alkyl, phenyl or benzyl;

$R^{1e}$ is selected at each occurrence from the methyl, ethyl, Cl, F, Br, I, OH, methoxy, ethoxy, —CN, —$NO_2$, —C(=O)$OR^{1d}$, $NR^{1d}R^{1d}$, $CF_3$, and $OCF_3$;

$R^2$ is H, $C_1$–$C_4$ alkyl, $C_2$–$C_4$ alkenyl, $C_2$–$C_4$ alkynyl, or $C_3$–$C_4$ cycloalkyl;

$R^3$ is —$R^4$, —$NR^4R^5$, —$OR^4$, or —$SR^4$;

$R^4$ is selected from the group: H,
  $C_1$–$C_8$ alkyl substituted with 0–3 $R^{4a}$,
  $C_2$–$C_8$ alkenyl substituted with 0–3 $R^{4a}$,
  $C_2$–$C_8$ alkynyl substituted with 0–3 $R^{4a}$,
  $C_3$–$C_{10}$ cycloalkyl substituted with 0–4 $R^{4b}$,
  aryl substituted with 0–5 $R^{4b}$,
  5–10 membered heterocyclic group consisting of carbon atoms and 1–4 heteroatoms selected from the group:
  O, S, and N, and said heterocyclic group is substituted with 0–3 $R^{4b}$;

$R^{4a}$ is, at each occurrence, independently selected from:
  H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, $OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy,
  $C_3$–$C_{10}$ cycloalkyl substituted with 0–4 $R^{4b}$,
  aryl substituted with 0–5 $R^{4b}$, and
  5–10 membered heterocyclic group consisting of carbon atoms and 1–4 heteroatoms selected from the group:
  O, S, and N, and said heterocyclic group is substituted with 0–3 $R^{4b}$;

$R^{4b}$ is, at each occurrence, independently selected from:
  H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy,
  $C_1$–$C_6$ alkyl substituted with 0–3 $R^{4c}$,
  $C_2$–$C_6$ alkenyl substituted with 0–3 $R^{4c}$,
  $C_2$–$C_6$ alkynyl substituted with 0–3 $R^{4c}$,
  $C_3$–$C_6$ cycloalkyl substituted with 0–4 $R^{4d}$,
  aryl substituted with 0–5 $R^{4d}$, and
  5–10 membered heterocyclic group consisting of carbon atoms and 1–4 heteroatoms selected from the group:
  O, S, and N, and said heterocyclic group is substituted with 0–3 $R^{4d}$;

$R^{4c}$ is, at each occurrence, independently selected from:
  H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, $OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy,
  $C_3$–$C_6$ cycloalkyl substituted with 0–4 $R^{4d}$,
  aryl substituted with 0–5 $R^{4d}$,
  5–10 membered heterocyclic group consisting of carbon atoms and 1–4 heteroatoms selected from the group:
  O, S, and N, and said heterocyclic group is substituted with 0–3 $R^{4d}$;

$R^{4d}$ is, at each occurrence, independently selected from:
  H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ alkyl, $C_1$–$C_4$ alkoxy, $C_1$–$C_4$ haloalkyl, and $C_1$–$C_4$ haloalkoxy;

$R^5$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^6$ is selected from the group: H, F, Cl, Br, I,
  $C_1$–$C_6$ alkyl substituted with 0–3 $R^{6a}$,
  $C_2$–$C_6$ alkenyl substituted with 0–3 $R^{6a}$,
  $C_2$–$C_6$ alkynyl substituted with 0–3 $R^{6a}$,
  $C_3$–$C_6$ cycloalkyl substituted with 0–4 $R^{6b}$,
  aryl substituted with 0–5 $R^{6b}$,
  5–6 membered heterocyclic group consisting of carbon atoms and 1–4 heteroatoms selected from the group: O, S, and N, and said heterocyclic group is substituted with 0–3 $R^{6b}$;

$R^{6a}$ is selected from the group: H, F, Cl, Br, I, —$CO_2R^{11}$, —$NR^{11}R^{11}$, —$OR^{11}$, —$SR^{11}$, —$C(=NH)NH_2$,
  $C_3$–$C_6$ cycloalkyl substituted with 0–4 $R^{6b}$,
  aryl substituted with 0–5 $R^{6b}$,
  5–6 membered heterocyclic group consisting of carbon atoms and 1–4 heteroatoms selected from the group: O, S, and N, and said heterocyclic group is substituted with 0–3 $R^{6b}$;

$R^{6b}$ is selected from the group: H, F, Cl, Br, I, —$CO_2R^{11}$, —$NR^{11}R^{11}$, —$OR^{11}$, —$SR^{11}$, —$C(=NH)NH_2$;
  $C_1$–$C_6$ alkyl substituted with 0–3 $R^{6c}$,
  $C_2$–$C_6$ alkenyl substituted with 0–3 $R^{6c}$,
  $C_2$–$C_6$ alkynyl substituted with 0–3 $R^{6c}$,
  $C_3$–$C_6$ cycloalkyl substituted with 0–4 $R^{6d}$,
  aryl substituted with 0–5 $R^{6d}$,
  5–6 membered heterocyclic group consisting of carbon atoms and 1–4 heteroatoms selected from the group: O, S, and N, and said heterocyclic group is substituted with 0–3 $R^{6d}$;

$R^{6c}$ is selected from the group: H, F, Cl, Br, I, —$CO_2R^{11}$, —$NR^{11}R^{11}$, —$OR^{11}$, —$SR^{11}$, —$C(=NH)NH_2$,
  $C_3$–$C_6$ cycloalkyl substituted with 0–4 $R^{6d}$,
  aryl substituted with 0–5 $R^{6d}$,
  5–6 membered heterocyclic group consisting of carbon atoms and 1–4 heteroatoms selected from the group: O, S, and N, and said heterocyclic group is substituted with 0–3 $R^{6d}$;

$R^{6d}$ is selected from the group: H, F, Cl, Br, I, —$CO_2R^{11}$, —$NR^{11}R^{11}$, —$OR^{11}$, —$SR^{11}$, —$C(=NH)NH_2$;

$R^8$ is H, $C_1$–$C_4$ alkyl, $C_2$–$C_4$ alkenyl, $C_2$–$C_4$ alkynyl, or $C_3$–$C_4$ cycloalkyl;

$R^9$ is selected from the group: —$S(=O)R^{9a}$, —$S(=O)_2R^{9a}$, —$C(=O)R^{9a}$, —$C(=O)OR^{9a}$, —$C(=O)NHR^{9a}$, $C_1$–$C_3$ alkyl-$R^{9a}$, $C_2$–$C_6$ alkenyl-$R^{9a}$, and $C_2$–$C_6$ alkynyl-$R^{9a}$;

$R^{9a}$ is selected from the group: H
  $C_1$–$C_6$ alkyl substituted with 0–3 $R^{9b}$,
  $C_3$–$C_6$ cycloalkyl substituted with 0–3 $R^{9c}$ and
  aryl substituted with 0–3 $R^{9c}$ and
  5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group:
  phenyl substituted with 0–3 $R^{9c}$,
  naphthyl substituted with 0–3 $R^{9c}$,
  benzyl substituted with 0–3 $R^{9c}$, and
  5–10 membered heterocyclic group consisting of carbon atoms and 1–4 heteroatoms selected from the group: O, S, and N; and said heterocyclic group is substituted with 0–3 $R^{9c}$;

$R^{9c}$ is selected at each occurrence from the group:
  H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, $OR^{11a}$, —$SR^{11a}$, $C(=O)R^{11a}$, —$S(=O)R^{11a}$, —$SO_2R^{11}$, —$SO_2NR^{11}R^{11}$, $C_1$–$C_4$ haloalkyl, $C_1$–$C_4$ haloalkoxy,
  $C_1$–$C_4$ alkyl substituted with 0–3 $R^{9d}$,
  $C_1$–$C_4$ alkoxy substituted with 0–3 $R^{9d}$,
  $C_3$–$C_6$ cycloalkyl substituted with 0–3 $R^{9d}$,
  aryl substituted with 0–5 $R^{9d}$, and
  5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
  H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, $OR^{11a}$, —$SR^{11a}$, —$C(=O)R^{11a}$, —$S(=O)R^{11a}$, —$SO_2R^{11}$, —$SO_2NR^{11}R^{11}$, $C_1$–$C_4$ alkyl, $C_1$–$C_4$ alkoxy, $C_1$–$C_4$ haloalkyl, and $C_1$–$C_4$ haloalkoxy;

$R^{10}$ is selected from the group: —$CO_2R^{11}$, —$NR^{11}R^{11}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, —$NR^{11}R^{11}$, —$OR^{11}$, —$SR^{11}$, —$C(=NH)NH_2$, and aryl substituted with 0–1 $R^{10b}$;

$R^{10b}$ is selected from the group: —$CO_2H$, —$NH_2$, —OH, —SH, and —$C(=NH)NH_2$;

$R^{10}c$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ is, at each occurrence, independently H or $C_1$–$C_4$ alkyl;

$R^{11a}$ is, at each occurrence, independently H, $C_1$–$C_4$ alkyl, aryl, or $C_1$–$C_4$ haloalkyl;

$R^{12}$ is H or $C_1$–$C_4$ alkyl;

$R^{13}$ is H or $C_1$–$C_4$ alkyl;

$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl);

$R^{20}$ is H, $C_1$–$C_4$ alkyl, $C_1$–$C_4$ haloalkyl, aryl, aryl($C_1$–$C_4$ alkyl)—, $C_3$–$C_6$ cycloalkyl, or $C_3$–$C_6$ cycloalkyl($C_{1C4}$ alkyl)-;

$R^{28}$ and $R^{29}$, are independently selected from: H, $C_1$–$C_4$ alkyl, aryl($C_1$–$C_4$ alkyl)-, and $C_3$–$C_7$ cycloalkyl;

$A^4$, $A^5$, $A^6$, $A^7$, $A^8$, and $A^9$ are independently selected from an amino acid residue;

an amino acid residue, at each occurence, independently comprises a natural amino acid, a modified amino acid or an unnatural amino acid wherein said natural, modified or unnatural amino acid is of either D or L configuration;

t is 1, 2, 3, or 4; and q is 0, 1 or 2.

[2] In a preferred embodiment, the present invention provides a novel compound of Formula (Ia), (Ib), or (Ic):

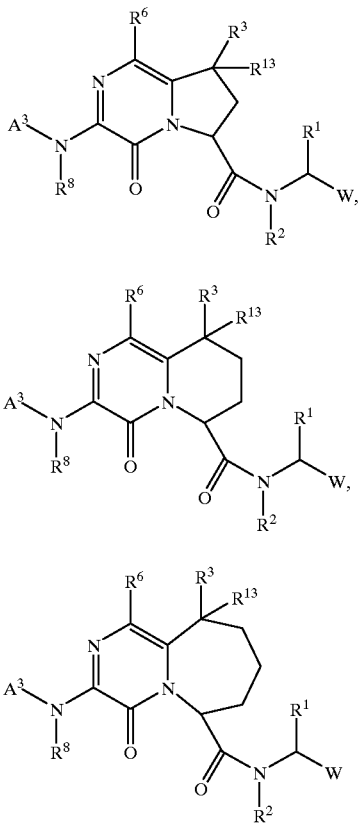

(Ia)

(Ib)

(Ic)

or a stereoisomer or pharmaceutically acceptable salt form thereof.

[3] In a more preferred embodiment, the present invention provides a compound of Formula (Ia):

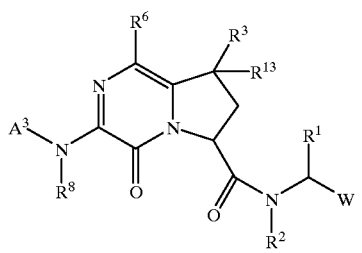

(Ia)

or a stereoisomer or pharmaceutically acceptable salt form thereof, wherein:

$A^3$ is selected from —$R^9$, —$A^4$—$R^9$, and —$A^4$—$A^5$—$R^9$;

W is selected from the group

—B($OR^{26}$) ($OR^{27}$),

—C(=O)C(=O)—Q,

—C(=O)C(=O)NH—Q,

—C(=O)C(=O)—O—Q,

—C(=O)$CF_2$C(=O)NH—Q,

—C(=O)$CF_3$,

—C(=O)$CF_2CF_3$,

—C(=O)H, an amino acid residue,

—$A^7$—$A^8$, and

—$A^7$—$A^8$—$A^9$;

Q is selected from —$(CR^{10}R^{10c})_t$—$Q^1$, —$(CR^{10}R^{10c})_t$—$Q^2$, $C_1$-$C_4$ alkyl substituted with $Q^1$, $C_2$-$C_4$ alkenyl substituted with $Q^1$, $C_2$-$C_4$ alkynyl substituted with $Q^1$, an amino acid residue, —$A^7$—$A^8$, and

—$A^7$—$A^8$—$A^9$;

$Q^1$ is selected from

—$CO_2R^{11}$, —$SO_2R^{11}$, —$SO_3R^{11}$, —$P(O)_2R^{11}$, —$P(O)_3R^{11}$, aryl substituted with 0–4 $Q^{1a}$, 5–6 membered heterocyclic group consisting of carbon atoms and 1–4 heteroatoms selected from the group: O, S, and N, said heterocyclic group substituted with 0–4 $Q^{1a}$;

$Q^{1a}$ is H, F, Cl, Br, I, —$NO_2$, —CN, —NCS, —$CF_3$, —$OCF_3$, —$CH_3$, —$OCH_3$, —$CO_2R^{19}$, —C(=O)$NR^{19}R^{19}$, —NHC(=O)$R^{19}$, —$SO_2R^{19}$, —$SO_2NR^{19}R^{19}$, —$NR^{19}R^{19}$, —$OR^{19}$, —$SR^{19}$, $C_1$-$C_4$ alkyl, $C_1$-$C_4$ alkoxy, $C_1$-$C_4$ haloalkyl, $C_1$-$C_4$ haloalkoxy alternatively, $NR^{19}R^{19}$ may form a 5–6 membered heterocyclic group consisting of carbon atoms, a nitrogen atom, and optionally a second heteroatom selected from the group:

O, S, and N;

$Q^2$ is —X—$NR^{12}$—Z, —$NR^{12}$—Y—Z, or —X—$NR^{12}$—Y—Z;

X is selected from the group: —C(=O)—, —S—, —S(=O)—, —S(=O)$_2$—, —P(O)—, —P(O)$_2$—, and —P(O)$_3$—;

Y is selected from the group: —C(=O)—, —S—, —S(=O)—, —S(=O)$_2$—, —P(O)—, —P(O)$_2$—, and —P(O)$_3$—;

Z is $C_1$-$C_4$ haloalkyl, $C_1$-$C_4$ alkyl substituted with 0–3 $Z^a$, $C_2$-$C_4$ alkenyl substituted with 0–3 $Z^a$, $C_2$-$C_4$ alkynyl substituted with 0–3 $Z^a$, $C_3$-$C_{10}$ cycloalkyl substituted with 0–5 $Z^b$, $C_3$-$C_{10}$ carbocyle substituted with 0–5 $Z^b$, aryl substituted with 0–5 $Z^b$, 5–10 membered heterocyclic group consisting of carbon atoms and 1–4 heteroatoms selected from the group: O, S, and N, said heterocyclic group substituted with 0–4 $Z^b$;

an amino acid residue,

—$A^7$—$A^8$, or

—$A^7$—$A^8$—$A^9$;

$Z^a$ is H, F, Cl, Br, I, —$NO_2$, —CN, —NCS, —$CF_3$, —$OCF_3$, —$CH_3$, —$OCH_3$, —$CO_2R^{20}$, —C(=O)$NR^{20}R^{20}$, —NHC(=O)$R^{20}$, —$NR^{20}R^{20}$, —$OR^{20}$, —$SR^{20}$, —S(=O)$R^{20}$, —$SO_2R^{20}$, —$SO_2NR^{20}R^{20}$, $C_1$-$C_4$ alkyl, $C_1$-$C_4$ alkoxy, $C_1$-$C_4$ haloalkyl, $C_1$-$C_4$ haloalkoxy, $C_3$-$C_{10}$ cycloalkyl substituted with 0–5 $Z^b$, $C_3$-$C_{10}$ carbocyle substituted with 0–5 $Z^b$, aryl substituted with 0–5 $Z^b$, or 5–10 membered heterocyclic group consisting of carbon atoms and 1–4 heteroatoms selected from the group: O, S, and N, said heterocyclic group substituted with 0–4 $Z^b$;

$Z^b$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$, —$NR^{20}R^{20}$, —$OR^{20}$, —$SR^{20}$, —$S(=O)R^{20}$, —$SO_2R^{20}$, —$SO_2NR^{20}R^{20}$, $C_1$-$C_4$ alkyl, $C_1$-$C_4$ alkoxy, $C_1$-$C_4$ haloalkyl, $C_1$-$C_4$ haloalkoxy, $C_3$-$C_{10}$ cycloalkyl substituted with 0–5 $Z^c$, $C_3$-$C_{10}$ carbocyle substituted with 0–5 $Z^c$, aryl substituted with 0–5 $Z^c$, or 5–10 membered heterocyclic group consisting of carbon atoms and 1–4 heteroatoms selected from the group: O, S, and N, said heterocyclic group substituted with 0–4 $Z^c$;

$Z^c$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$, —$NR^{20}R^{20}$, —$OR^{20}$, —$SR^{20}$, —$S(=O)R^{20}$, —$SO_2R^{20}$, —$SO_2NR^{20}R^{20}$, —$C_1$-$C_4$ alkyl, $C_1$-$C_4$ alkoxy, $C_1$-$C_4$ haloalkyl, $C_1$-$C_4$ haloalkoxy;

alternatively, $NR^{20}R^{20}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:

a) —OH, b) —F, c) —$NR^{28}R^{29}$, d) $C_1$-$C_8$ alkoxy, or when taken together, $OR^{26}$ and $OR^{27}$ form:

e) a cyclic boron ester where said chain or ring contains from 2 to 20 carbon atoms, and, optionally, 1, 2, or 3 heteroatoms which can be N, S, or O, f) a cyclic boron amide where said chain or ring contains from 2 to 20 carbon atoms, and, optionally, 1, 2, or 3 heteroatoms which can be N, S, or O, g) a cyclic boron amide-ester where said chain or ring contains from 2 to 20 carbon atoms and, optionally, 1, 2, or 3 heteroatoms which can be N, S, or O;

$R^1$ is selected from the group: H, F, $C_1$-$C_6$ alkyl substituted with 0–3 $R^{1a}$, $C_2$-$C_6$ alkenyl substituted with 0–3 $R^{1a}$, $C_2$-$C_6$ alkynyl substituted with 0–3 $R^{1a}$, aryl substituted with 0–5 $R^{1a}$, and $C_3$-$C_6$ cycloalkyl substituted with 0–3 $R^{1a}$;

$R^{1a}$ is selected at each occurrence from the group:

Cl, F, Br, I, $CF_3$, $CHF_2$, OH, =O, SH, —$CO_2R^{1b}$, —$SO_2R^{1b}$, —$SO_3R^{1b}$, —$P(O)_2R^{1b}$, —$P(O)_3R^{1b}$, —$C(=O)NHR^{1b}$, —$NHC(=O)R^{1b}$, —$SO_2NHR^{1b}$, —$OR^{1b}$, —$SR^{1b}$, $C_1$-$C_3$ alkyl, $C_3$-$C_6$ cycloalkyl, $C_1$-$C_6$ alkoxy, —S—($C_1$-$C_6$ alkyl), aryl substituted with 0–5 $R^{1c}$, —O—$(CH_2)_q$-aryl substituted with 0–5 $R^{1c}$, —S—$(CH_2)_q$-aryl substituted with 0–5 $R^{1c}$, 5–10 membered heterocyclic group consisting of carbon atoms and 1–4 heteroatoms selected from the group: O, S, and N, and substituted with 0–3 $R^{1c}$;

$R^{1b}$ is H, $C_1$-$C_4$ alkyl substituted with 0–3 $R^{1c}$, $C_2$-$C_4$ alkenyl substituted with 0–3 $R^{1c}$, $C_2$-$C_4$ alkynyl substituted with 0–3 $R^{1c}$, $C_3$-$C_6$ cycloalkyl substituted with 0–5 $R^{1c}$, $C_3$-$C_6$ carbocyle substituted with 0–5 $R^{1c}$, aryl substituted with 0–5 $R^{1c}$, 5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:

$C_1$-$C_4$ alkyl, Cl, F, Br, I, OH, $C_1$-$C_4$ alkoxy, —CN, —$NO_2$, —$OR^{1d}$, —$C(=O)OR^{1d}$, $NR^{1d}R^{1d}$, $CF_3$, $OCF_3$, and aryl substituted by 0–3 $R^{1e}$;

$R^{1d}$ is H, methyl, ethyl, propyl, butyl, phenyl, or benzyl;

$R^{1e}$ is selected at each occurrence from the methyl, ethyl, Cl, F, Br, I, OH, methoxy, ethoxy, —CN, —$NO_2$, —$C(=O)$ $OR^{1d}$, $NR^{1d}R^{1d}$, $CF_3$, and $OCF_3$;

$R^2$ is H, methyl, ethyl, propyl, butyl, or cyclopropyl;

$R^3$ is —$R^4$, —$NR^4R^5$, —$OR^4$, or —$SR^4$;

$R^4$ is selected from the group: H, $C_1$-$C_8$ alkyl substituted with 0–3 $R^{4a}$, $C_2$-$C_8$ alkenyl substituted with 0–3 $R^{4a}$, $C_2$-$C_8$ alkynyl substituted with 0–3 $R^{4a}$, $C_3$-$C_{10}$ cycloalkyl substituted with 0–4 $R^{4b}$, aryl substituted with 0–5 $R^{4b}$, 5–10 membered heterocyclic group consisting of carbon atoms and 1–4 heteroatoms selected from the group: O, S, and N, and said heterocyclic group is substituted with 0–3 $R^{4b}$;

$R^{4a}$ is, at each occurrence, independently selected from:

H, F, Cl, Br, I, —$NO_2$, —CN, —NCS, —$CF_3$, —$OCF_3$, —$CH_3$, —$OCH_3$, =O, OH, —$CO_2H$, phenyl, —$C(=NH)NH_2$, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, $OR^{11a}$, —$SR^{11a}$, —$C(=O)R^{11a}$, —$S(=O)R^{11a}$, —$SO_2R^{11}$, —$SO_2NR^{11}R^{11}$, $C_1$-$C_4$ haloalkyl, $C_1$-$C_4$ haloalkoxy, $C_3$-$C_{10}$ cycloalkyl substituted with 0–4 $R^{4b}$, aryl substituted with 0–5 $R^{4b}$, and 5–10 membered heterocyclic group consisting of carbon atoms and 1-4 heteroatoms selected from the group: O, S, and N, and said heterocyclic group is substituted with 0–3 $R^{4b}$;

$R^{4b}$ is, at each occurrence, independently selected from:

H, F, Cl, Br, I, —$NO_2$, —CN, —NCS, —$CF_3$, —$OCF_3$, —$CH_3$, $OCH_3$, =O, OH, —$CO_2H$, phenyl, —$C(=NH)NH_2$, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, —$OR^{11a}$, $SR^{11a}$, —$C(=O)R^{11a}$, —$S(=O)R^{11a}$, —$SO_2R^{11}$, —$SO_2NR^{11}R^{11}$, $C_1$-$C_4$ haloalkyl, $C_1$-$C_4$ haloalkoxy, $C_1$-$C_6$ alkyl substituted with 0–3 $R^{4c}$, $C_2$-$C_6$ alkenyl substituted with 0–3 $R^{4c}$, $C_2$-$C_6$ alkynyl substituted with 0–3 $R^{4c}$, $C_3$-$C_6$ cycloalkyl substituted with 0–4 $R^{4d}$, aryl substituted with 0–5 $R^{4d}$, and 5–10 membered heterocyclic group consisting of carbon atoms and 1–4 heteroatoms selected from the group: O, S, and N, and said heterocyclic group is substituted with 0–3 $R^{4d}$;

$R^{4c}$ is, at each occurrence, independently selected from:

H, F, Cl, Br, I, —$NO_2$, —CN, —NCS, —$CF_3$, —$OCF_3$, —$CH_3$, —$OCH_3$, =O, OH, —$CO_2H$, phenyl, —$C(=NH)NH_2$, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, $OR^{11a}$, —$SR^{11a}$, —$C(=O)R^{11a}$, $S(=O)$ $R^{11a}$, —$SO_2R^{11}$, —$SO_2NR^{11}R^{11}$, $C_1$-$C_4$ haloalkyl, $C_1$-$C_4$ haloalkoxy, $C_3$-$C_6$ cycloalkyl substituted with 0–4 $R^{4d}$, aryl substituted with 0–5 $R^{4d}$, 5–10 membered heterocyclic group consisting of carbon atoms and 1–4 heteroatoms selected from the group: O, S, and N, and said heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —NH($CH_3$), -N($CH_3$)$_2$, —$CO_2R^{11}$, —C(=O)$NR^{11}R^{11}$, —NHC(=O)$R^{11}$, —$NR^{11}R^{11a}$, —$OR^{11a}$, —$SR^{11a}$, C(=O)$R^{11a}$, —S(=O)$R^{11a}$, —$SO_2R^{11}$, —$SO_2NR^{11}R^{11}$, $C_1$–$C_4$ alkyl, $C_1$–$C_4$ alkoxy, $C_1$–$C_4$ haloalkyl, and $C_1$–$C_4$ haloalkoxy;

$R^5$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^6$ is H, Cl, Br, methyl, ethyl, or cyclopropyl;

$R^8$ is H, methyl, ethyl, propyl, butyl, or cyclopropyl;

$R^9$ is selected from the group: —S(=O)$R^{9a}$, —S(=O)$_2R^{9a}$, —C(=O)$R^{9a}$, —C(=O)$OR^{9a}$, —C(=O)$NHR^{9a}$, $C_1$–$C_3$ alkyl-$R^{9a}$, $C_2$–$C_6$ alkenyl-$R^{9a}$, and $C_2$–$C_6$ alkynyl-$R^{9a}$;

$R^{9a}$ is selected from the group:
H $C_1$–$C_6$ alkyl substituted with 0–3 $R^{9b}$,
$C_3$–$C_6$ cycloalkyl substituted with 0–3 $R^{9c}$ and
aryl substituted with 0–3 $R^{9c}$ and
5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group:
phenyl substituted with 0–3 $R^{9c}$,
naphthyl substituted with 0–3 $R^{9c}$,
benzyl substituted with 0–3 $R^{9c}$, and
5–10 membered heterocyclic group consisting of carbon atoms and 1–4 heteroatoms selected from the group: O, S, and N; and said heterocyclic group is substituted with 0–3 $R^{9c}$;

$R^{9c}$ is selected at each occurrence from the group:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy,
$C_1$–$C_4$ alkyl substituted with 0–3 $R^{9d}$,
$C_1$–$C_4$ alkoxy substituted with 0–3 $R^{9d}$,
$C_3$–$C_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ alkyl, $C_1$–$C_4$ alkoxy, $C_1$–$C_4$ haloalkyl, and $C_1$–$C_4$ haloalkoxy;

$R^{10}$ is selected from the group: —$CO_2R^{11}$, —$NR^{11}R^{11}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, —$NR^{11}R^{11}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ is, at each occurrence, independently H or $C_1$–$C_4$ alkyl;

$R^{11a}$ is, at each occurrence, independently H, $C_1$–$C_4$ alkyl, aryl, or $C_1$–$C_4$ haloalkyl;

$R^{12}$ is H or $C_1$–$C_4$ alkyl;

$R^{13}$ is H, methyl, ethyl, propyl, or butyl;

$A^4$, $A^5$, $A^7$, $A^8$, and $A^9$ are independently selected from an amino acid residue;

an amino acid residue, at each occurence, independently comprises a natural amino acid, a modified amino acid or an unnatural amino acid wherein said natural, modified or unnatural amino acid is of either D or L configuration;

$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl); $R^{20}$ is H, $C_1$–$C_4$ alkyl, $C_1$–$C_4$ haloalkyl, aryl, aryl($C_1$–$C_4$ alkyl)- , $C_3$–$C_6$ cycloalkyl, or $C_3$–$C_6$ cycloalkyl($C_1$–$C_4$ alkyl)-;

$R^{28}$ and $R^{29}$, are independently selected from: H, $C_1$–$C_4$ alkyl, aryl($C_1$–$C_4$ alkyl)-, and $C_3$–$C_7$ cycloalkyl;

t is 1, 2, or 3; and q is 0, 1 or 2.

[4] In a further more preferred embodiment, the present invention provide a novel compound of Formula (Ia): wherein $A^3$ is selected from —$R^9$, —$A^4$—$R^9$, and —$A^4$—$A^5$—$R^9$; and W is —B($OR^{26}$)($OR^{27}$), —C(=O)C(=O)NH—Q, —C(=O)$CF_2$C(=O)NH—Q, —C(=O)$CF_3$, —C(=O)H, or an amino acid residue.

[5] In an even more preferred embodiment, the present invention provide a novel compound of Formula (II):

(II)

or a stereoisomer or pharmaceutically acceptable salt form thereof, wherein:

$A^3$ is selected from —$R^9$, —$A^4$—$R^9$, and —$A^4$—$A^5$—$R^9$;

$OR^{26}$ and $OR^{27}$ are independently selected from:

a) —OH, b) —F, c) —$NR^{28}R^{29}$, d) $C_1$–$C_8$ alkoxy, or when taken together, $OR^{26}$ and $OR^{27}$ form:

e) a cyclic boron ester where said chain or ring contains from 2 to 20 carbon atoms, and, optionally, 1, 2, or 3 heteroatoms which can be N, S, or O, f) a cyclic boron amide where said chain or ring contains from 2 to 20 carbon atoms and, optionally, 1, 2, or 3 heteroatoms which can be N, S, or O, g) a cyclic boron amide-ester where said chain or ring contains from 2 to 20 carbon atoms and, optionally, 1, 2, or 3 heteroatoms which can be N, S, or O;

$R^1$ is selected from the group:
H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$,
aryl substituted with 0–5 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH,
—$CO_2R^{1b}$, —$SO_2R^{1b}$, —$SO_3R^{1b}$, —$P(O)_2R^{1b}$, —$P(O)_3R^{1b}$,
—C(=O)$NHR^{1b}$, —NHC(=O)$R^{1b}$, —$SO_2NHR^{1b}$,
—$OR^{1b}$, —$SR^{1b}$, $C_1$–$C_3$ alkyl, $C_3$–$C_6$ cycloalkyl, $C_1$–$C_6$ alkoxy, —S—($C_1$–$C_6$ alkyl),
aryl substituted with 0–5 $R^{1c}$,
—O—$(CH_2)_q$-aryl substituted with 0–5 $R^{1c}$,
—S—$(CH_2)_q$-aryl substituted with 0–5 $R^{1c}$,
5–10 membered heterocyclic group consisting of carbon atoms and 1–4 heteroatoms selected from the group: O, S, and N, and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocyle substituted with 0–5 $R^{1c}$,
aryl substituted with 0–5 $R^{1c}$,
5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:
$C_1$–$C_4$ alkyl, Cl, F, Br, I, OH, $C_1$–$C_4$ alkoxy, —CN, —$NO_2$, —$OR^{1d}$, —C(=O)$OR^{1d}$, $NR^{1d}R^{1d}$, $CF_3$, $OCF_3$, and aryl substituted by 0–3 $R^{1e}$;

$R^{1d}$ is H, methyl, ethyl, propyl, butyl, phenyl, or benzyl;
$R^{1e}$ is selected at each occurrence from the methyl, ethyl, Cl, F, Br, I, OH, methoxy, ethoxy, —CN, —$NO_2$, —C(=O)$OR^{1d}$, $NR^{1d}R^{1d}$, $CF_3$, and $OCF_3$;

$R^2$ is H, methyl, ethyl, propyl, butyl, or cyclopropyl;
$R^3$ is —$R^4$, —$NR^4R^5$, —$OR^4$, or —$SR^4$;
$R^4$ is selected from the group:
H,
$C_1$–$C_8$ alkyl substituted with 0–3 $R^{4a}$,
$C_2$–$C_8$ alkenyl substituted with 0–3 $R^{4a}$,
$C_2$–$C_8$ alkynyl substituted with 0–3 $R^{4a}$,
$C_3$–$C_{10}$ cycloalkyl substituted with 0–4 $R^{4b}$,
aryl substituted with 0–5 $R^{4b}$,
5–10 membered heterocyclic group consisting of carbon atoms and 1–4 heteroatoms selected from the group: O, S, and N, and said heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy,
$C_3$–$C_{10}$ cycloalkyl substituted with 0–4 $R^{4b}$,
aryl substituted with 0–5 $R^{4b}$, and
5–10 membered heterocyclic group consisting of carbon atoms and 1–4 heteroatoms selected from the group: O, S, and N, and said heterocyclic group is substituted with 0–3 $R^{4b}$;

$R^{4b}$ is, at each occurrence, independently selected from:
H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, $OR^{11a}$, $SR^{11a}$, C(=O)$R^{11a}$, S(=O)$R^{11a}$, —$SO_2R^{11}$, —$SO_2NR^{11}R^{11}$, $C_1$–$C_4$ haloalkyl, $C_1$–$C_4$ haloalkoxy,
$C_1$–$C_6$ alkyl substituted with 0–3 $R^{4c}$,
$C_2$–$C_6$ alkenyl substituted with 0–3 $R^{4c}$,
$C_2$–$C_6$ alkynyl substituted with 0–3 $R^{4c}$,
$C_3$–$C_6$ cycloalkyl substituted with 0–4 $R^{4d}$,
aryl substituted with 0–5 $R^{4d}$, and
5–10 membered heterocyclic group consisting of carbon atoms and 1–4 heteroatoms selected from the group: O, S, and N, and said heterocyclic group is substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy,
$C_3$–$C_6$ cycloalkyl substituted with 0–4 $R^{4d}$,
aryl substituted with 0–5 $R^{4d}$,
5–10 membered heterocyclic group consisting of carbon atoms and 1–4 heteroatoms selected from the group: O, S, and N, and said heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —NH($CH_3$), —N($CH_3$)$_2$, —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ alkyl, $C_1$–$C_4$ alkoxy, $C_1$–$C_4$ haloalkyl, and $C_1$–$C_4$ haloalkoxy;

$R^5$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;
$R^6$ is H, Cl, Br, methyl, ethyl, or cyclopropyl;
$R^8$ is H, methyl, ethyl, propyl, butyl, or cyclopropyl;
$R^9$ is selected from the group: —S(=O)$R^{9a}$, —S(=O)$_2R^{9a}$, —C(=O)$R^{9a}$, —C(=O)$OR^{9a}$, —C(=O)$NHR^{9a}$, $C_1$–$C_3$ alkyl-$R^{9a}$, $C_2$–$C_6$ alkenyl-$R^{9a}$, and $C_2$–$C_6$ alkynyl-$R^{9a}$;
$R^{9a}$ is selected from the group: H
$C_1$–$C_6$ alkyl substituted with 0–3 $R^{9b}$,
$C_3$–$C_6$ cycloalkyl substituted with 0–3 $R^{9c}$0 and
aryl substituted with 0–3 $R^{9c}$ and
5–14 membered heterocyclic group consisting of carbon atoms and 1–4 heteroatoms selected from the group: O, S, and N, and said heterocyclic group is substituted with 0–3 $R^{9c}$;
$R^{9b}$ is selected from the group:
phenyl substituted with 0–3 $R^{9c}$,
naphthyl substituted with 0–3 $R^{9c}$, benzyl substituted with 0–3 $R^{9c}$, and 5–10 membered heterocyclic group consisting of carbon atoms and 1–4 heteroatoms selected from the group: O, S, and N; and said heterocyclic group is substituted with 0–3 $R^{9c}$;

$R^{9c}$ is selected at each occurrence from the group:

H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —$NH(CH_3)$, —$N(CH_3)_2$, —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$, $C_1$–$C_4$ haloalkyl, $C_1$–$C_4$ haloalkoxy, $C_1$–$C_4$ alkyl substituted with 0–3 $R^{9d}$, $C_1$–$C_4$ alkoxy substituted with 0–3 $R^{9d}$, $C_3$–$C_6$ cycloalkyl substituted with 0–3 $R^{9d}$, aryl substituted with 0–5 $R^{9d}$, and 5–6 membered heterocyclic group consisting of carbon atoms and 1–4 heteroatoms selected from the group: O, S, and N, and said heterocyclic group is substituted with 0–4 $R^{9d}$;

$R^9d$ is selected at each occurrence from the group:

H, F, Cl, Br, I, —$NO_2$, —CN, —NCS, —$CF_3$, —$OCF_3$, —$CH_3$, —$OCH_3$, =O, OH, —$CO_2H$, phenyl, —$NH_2$, —$NH(CH_3)$, —$N(CH_3)_2$, —$CO_2R^{11}$, —C(=O)$NR^{11}R^{11}$, —NHC(=O)$R^{11}$, —$NR^{11}R^{11}$, $OR^{11a}$, —$SR^{11a}$, —C(=O)$R^{11a}$, S(=O)$R^{11a}$, —$SO_2R^{11}$, —$SO_2NR^{11}R^{11}$, $C_1$–$C_4$ alkyl, $C_1$–$C_4$ alkoxy, $C_1$–$C_4$ haloalkyl, and $C_1$–$C_4$ haloalkoxy;

$R^{11}$ is, at each occurrence, independently H or $C_1$–$C_4$ alkyl;

$R^{11a}$ is, at each occurrence, independently H, $C_1$–$C_4$ alkyl, aryl, or $C_1$–$C_4$ haloalkyl;

$R^{13}$ is H, methyl, ethyl, propyl, or butyl;

$A^4$ and $A^5$ are independently selected from an amino acid residue;

an amino acid residue, at each occurence, independently comprises Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

$R^{28}$ and $R^{29}$ are independently selected from:

H, methyl, ethyl, propyl, butyl, phenylmethyl-, phenylethyl-, phenylpropyl-, cyclopropyl, cyclobutyl, cyclopentyl, and cyclohexyl;

q is 0, 1 or 2.

[6] In a further even more preferred embodiment, the present invention provides a novel compound of Formula (II):

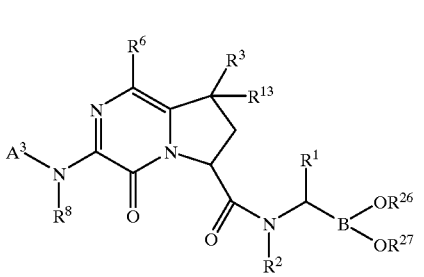

(II)

or a stereoisomer or pharmaceutically acceptable salt form thereof, wherein:

$A^3$ is —$R^9$ or —$A^4$—$R^9$;

$OR^{26}$ and $OR^{27}$ are independently selected from:

a) —OH, b) —F, c) $C_1$–$C_6$ alkoxy, or when taken together, $OR^{26}$ and $OR^{27}$ form:

d) a cyclic boron ester where said chain or ring contains from 2 to 16 carbon atoms, and, optionally, 1, 2, or 3 heteroatoms which can be N, S, or O, $R^1$ is selected from the group: H, F, $C_1$–$C_6$ alkyl substituted with 0–3 $R^{1a}$, $C_2$–$C_6$ alkenyl substituted with 0–3 $R^{1a}$, $C_2$–$C_6$ alkynyl substituted with 0–3 $R^{1a}$, and $C_3$–$C_6$ cycloalkyl substituted with 0–3 $R^{1a}$;

$R^{1a}$ is selected at each occurrence from the group:

Cl, F, Br, I, $CF_3$, $CHF_2$, OH, =O, SH, —$CO_2R^{1b}$, —$SO_2R^{1b}$, —$SO_3R^{1b}$, —P(O)$^2R^{1b}$, —P(O )$_3R^{1b}$, —C(=O)$NHR^{1b}$, —NHC(=O)$R^{1b}$, —$SO_2NHR^{1b}$, —$OR^{1b}$, —$SR^{1b}$, $C_1$–$C_3$ alkyl, $C_3$–$C_6$ cycloalkyl, $C_1$–$C_6$ alkoxy, —S—($C_1$–$C_6$ alkyl), aryl substituted with 0–5 $R^{1c}$, —O—$(CH_2)_q$-aryl substituted with 0–5 $R^{1c}$, —S—$(CH_2)_q$-aryl substituted with 0–5 $R^{1c}$, 5–10 membered heterocyclic group consisting of carbon atoms and 1–4 heteroatoms selected from the group: O, S, and N, and substituted with 0–3 $R^{1c}$;

$R^{1b}$ is H, $C_1$–$C_4$ alkyl substituted with 0–3 $R^{1c}$, $C_2$–$C_4$ alkenyl substituted with 0–3 $R^{1c}$, $C_2$–$C_4$ alkynyl substituted with 0–3 $R^{1c}$, $C_3$–$C_6$ cycloalkyl substituted with 0–5 $R^{1c}$, $C_3$–$C_6$ carbocyle substituted with 0–5 $R^{1c}$, aryl substituted with 0–5 $R^{1c}$, 5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:

$C_1$–$C_4$ alkyl, Cl, F, Br, I, OH, $C_1$–$C_4$ alkoxy, —CN, —$NO_2$, $OR^{1d}$, —C(=O)$OR^{1d}$, $NR^{1d}R^{1d}$, $CF_3$, $OCF_3$, and phenyl substituted with 0–3 $R^{1e}$;

$R^{1d}$ is H, methyl, ethyl, propyl, butyl, phenyl, or benzyl;

$R^{1e}$ is selected at each occurrence from the methyl, ethyl, Cl, F, Br, I, OH, methoxy, ethoxy, —CN, —$NO_2$, —C(=O)$OR^{1d}$, $NR^{1d}R^{1d}$, $CF_3$, and $OCF_3$;

$R^2$ is H, methyl, ethyl, propyl, butyl, or cyclopropyl;

$R^3$ is —$R^4$, —$NR^4R^5$, —$OR^4$, or —$SR^4$;

$R^4$ is selected from the group: H, $C_1$–$C_6$ alkyl substituted with 0–3 $R^{4a}$, $C_2$–$C_6$ alkenyl substituted with 0–3 $R^{4a}$, $C_2$–$C_6$ alkynyl substituted with 0–3 $R^{4a}$, $C_3$–$C_{10}$ cycloalkyl substituted with 0–4 $R^{4b}$, aryl substituted with 0–5 $R^{4b}$, 5–10 membered heterocyclic group consisting of carbon atoms and 1–4 heteroatoms selected from the group: O, S, and N, and said heterocyclic group is substituted with 0–3 $R^{4b}$;

$R^4a$ is, at each occurrence, independently selected from:

H, F, Cl, Br, I, —$NO_2$, —CN, —NCS, —$CF_3$, —$OCF_3$, —$CH_3$, —$OCH_3$, =O, OH, —$CO_2H$, phenyl, —C(=NH)$NH_2$, —$NH_2$, —$NH(CH_3)$, —$N(CH_3)_2$, —$CO_2R^{11}$, —C(=O)$NR^{11}R^{11}$, —NHC(=O)$R^{11}$, —$NR^{11}R^{11}$, $OR^{11a}$, —$SR^{11a}$, —C(=O)$R^{11a}$, —S(=O)$R^{11a}$, —$SO_2R^{11}$—$SO_2NR^{11}R^{11}$, $C_1$–$C_4$ haloalkyl, $C_1$–$C_4$ haloalkoxy, C$_3$–C$_{10}$ cycloalkyl substituted with 0–4 R$^{4b}$,
aryl substituted with 0–5 R$^{4b}$, and
5–10 membered heterocyclic group consisting of carbon atoms and 1–4 heteroatoms selected from the group: O, S, and N, and said heterocyclic group is substituted with 0–3 R$^{4b}$;

R$^{4b}$ is, at each occurrence, independently selected from:
H, F, Cl, Br, I, —NO$_2$, —CN, —NCS, —CF$_3$, —OCF$_3$, —CH$_3$, —OCH$_3$, =O, OH, —CO$_2$H, phenyl, —C(=NH)NH$_2$, —NH$_2$, —NH(CH$_3$), —N(CH$_3$)$_2$, —CO$_2$R$^{11}$, —C(=O)NR$^{11}$R$^{11}$, —NHC(=O)R$^{11}$, —NR$^{11}$R$^{11}$, OR$^{11a}$,
—SR$^{11a}$, —C(=O)R$^{11a}$, S(=O)R$^{11a}$, —SO$_2$R$^{11}$, —SO$_2$NR$^{11}$R$^{11}$,
C$_1$–C$_4$ haloalkyl, C$_1$–C$_4$ haloalkoxy,
C$_1$–C$_6$ alkyl substituted with 0–3 R$^{4c}$,
C$_2$–C$_6$ alkenyl substituted with 0–3 R$^{4c}$,
C$_2$–C$_6$ alkynyl substituted with 0–3 R$^{4c}$,
C$_3$–C$_6$ cycloalkyl substituted with 0–4 R$^{4d}$,
aryl substituted with 0–5 R$^{4d}$, and
5–6 membered heterocyclic group consisting of carbon atoms and 1–4 heteroatoms selected from the group: O, S, and N, and said heterocyclic group is substituted with 0–3 R$^{4d}$;

R$^{4c}$ is, at each occurrence, independently selected from:
H, F, Cl, Br, I, —NO$_2$, —CN, —NCS, —CF$_3$, —OCF$_3$, —CH$_3$, —OCH$_3$, =O, OH, —CO$_2$H, phenyl, —C(=NH)NH$_2$, —NH$_2$, —NH(CH$_3$), —N(CH$_3$)$_2$, —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11}$, C$_1$–C$_4$ haloalkyl, C$_1$–C$_4$ haloalkoxy,
C$_3$—C$_6$ cycloalkyl substituted with 0–4 R$^{4d}$,
aryl substituted with 0–5 R$^{4d}$,
5–6 membered heterocyclic group consisting of carbon atoms and 1–4 heteroatoms selected from the group: O, S, and N, and said heterocyclic group is substituted with 0–3 R$^{4d}$;

R$^{4d}$ is, at each occurrence, independently selected from:
H, F, Cl, Br, I, —NO$_2$, —CN, —NCS, —CF$_3$, —OCF$_3$, —CH$_3$, —OCH$_3$, =O, OH, —CO$_2$H, phenyl, —NH$_2$, —NH(CH$_3$), —N(CH$_3$)$_2$, —CO$_2$R$^{11}$, —C(=O) NR$^{11}$R$^{11}$, —NHC(=O)R$^{11}$, —NR$^{11}$R$^{11}$, OR$^{11a}$, —SR$^{11a}$, —C(=O)R$^{11a}$, —S(=O)R$^{11a}$, —SO$_2$R$^{11}$, —SO$_2$NR$^{11}$R$^{11}$, C$_1$–C$_4$ alkyl, C$_1$–C$_4$ alkoxy, C$_1$–C$_4$ haloalkyl, and C$_1$–C$_4$ haloalkoxy;

R$^5$ is selected from the group:
H, methyl, ethyl, propyl, butyl, phenyl, phenylmethyl-, phenylethyl-, cyclopropyl, cyclobutyl, cyclopentyl, cyclohexyl, cyclopropylmethyl-, cyclobutylmethyl-, cyclopentylmethyl-, cyclohexylmethyl-, cyclopropylethyl-, cyclobutylethyl-, cyclopentylethyl-, and cyclohexylethyl-;

R$^6$ is H, Cl, Br, or methyl;
R$^8$ is H, methyl, ethyl, or cyclopropyl;
R$^9$ is selected from the group: —S(=O)R$^{9a}$, —S(=O)$_2$R$^{9a}$, —C(=O)R$^{9a}$, —C(=O)OR$^{9a}$, —C(=O)NHR$^{9a}$, C$_1$–C$_3$ alkyl-R$^{9a}$, C$_2$–C$_6$ alkenyl-R$^{9a}$, and C$_2$–C$_6$ alkynyl-R$^{9a}$;

R$^{9a}$ is selected from the group: H
C$_1$–C$_6$ alkyl substituted with 0–3 R$^{9b}$,
C$_3$–C$_6$ cycloalkyl substituted with 0–3 R$^{9c}$ and
aryl substituted with 0–3 R$^{9c}$ and
5–14 membered heterocyclic group consisting of carbon atoms and 1–4 heteroatoms selected from the group:

O, S, and N, and said heterocyclic group is substituted with 0–3 R$^{9c}$;

R$^9$c is selected from the group:
phenyl substituted with 0–3 R$^{9c}$,
naphthyl substituted with 0–3 R$^{9c}$,
benzyl substituted with 0–3 R$^{9c}$, and
5–10 membered heterocyclic group consisting of carbon atoms and 1–4 heteroatoms selected from the group: O, S, and N; and said heterocyclic group is substituted with 0–3 R$^{9c}$;

R$^{9c}$ is selected at each occurrence from the group:
H, F, Cl, Br, I, —NO$_2$, —CN, —NCS, —CF$_3$, —OCF$_3$, —CH$_3$, —OCH$_3$, =O, OH, —CO$_2$H, phenyl, —NH$_2$, —NH(CH$_3$), —N(CH$_3$)$_2$, —CO$_2$R$^{11}$, —C(=O) NR$^{11}$R$^{11}$, —NHC(=O)R$^{11}$, —NR$^{11}$R$^{11}$, OR$^{11a}$, —SR$^{11a}$, —C(=O)R$^{11a}$, —S(=O)R$^{11a}$, —SO$_2$R$^{11}$, —SO$_2$NR$^{11}$R$^{11}$, C$_1$–C$_4$ haloalkyl, C$_1$–C$_4$ haloalkoxy,
C$_1$–C$_4$ alkyl substituted with 0–3 R$^{9d}$,
C$_1$–C$_4$ alkoxy substituted with 0–3 R$^{9d}$,
C$_3$–C$_6$ cycloalkyl substituted with 0–3 R$^{9d}$,
aryl substituted with 0–5 R$^{9d}$, and
5–6 membered heterocyclic group consisting of carbon atoms and 1–4 heteroatoms selected from the group: O, S, and N, and said heterocyclic group is substituted with 0–4 R$^{9d}$;

R$^{9d}$ is selected at each occurrence from the group:
H, F, Cl, Br, I, —NO$_2$, —CN, —NCS, —CF$_3$, —OCF$_3$, —CH$_3$, —OCH$_3$, =O, OH, —CO$_2$H, phenyl, —NH$_2$, —NH(CH$_3$), —N(CH$_3$)$_2$, —CO$_2$R$^{11}$, —C(=O) NR$^{11}$R$^{11}$, —NHC(=O)R$^{11}$, —NR$^{11}$R$^{11}$, —OR$^{11a}$, —SR$^{11a}$, C(=O)R$^{11a}$, S(=O)R$^{11a}$, —SO$_2$R$^{11}$, —SO$_2$NR$^{11}$R$^{11}$, C$_1$–C$_4$ alkyl, C$_1$–C$_4$ alkoxy, C$_1$–C$_4$ haloalkyl, and C$_1$–C$_4$ haloalkoxy;

R$^{11}$ is, at each occurrence, independently H or C$_1$–C$_4$ alkyl;
R$^{11a}$ is, at each occurrence, independently H, C$_1$–C$_4$ alkyl, aryl, or C$_1$–C$_4$ haloalkyl;
R$^{13}$ is H, methyl, ethyl, propyl, or butyl;
A$^4$ is selected from Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val; and
q is 0, 1 or 2.

[7] In most preferred embodiment, the present invention provides a compound of Formula (II):

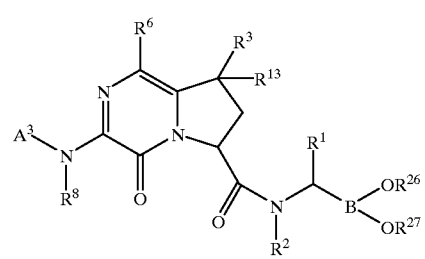

(II)

or a stereoisomer or pharmaceutically acceptable salt form thereof, wherein:
A$^3$ is —R$^9$;
OR$^{26}$ and OR$^{27}$ are independently selected from:
a) —OH,
b) —F,
c) methyloxy, ethyloxy, propyloxy, butyloxy, pentyloxy, or hexyloxy, when taken together, $OR^{26}$ and $OR^{27}$ form:
  d) a cyclic boron ester where said chain or ring contains from 2 to 12 carbon atoms, and, optionally, a heteroatom which can be N, S, or O;
$R^1$ is selected from the group: H, F,
  $C_1$–$C_6$ alkyl substituted with 0–3 $R^{1a}$,
  $C_2$–$C_6$ alkenyl substituted with 0–3 $R^{1a}$,
  $C_2$–$C_6$ alkynyl substituted with 0–3 $R^{1a}$, and
  $C_3$–$C_6$ cycloalkyl substituted with 0–3 $R^{1a}$;
$R^{1a}$ is selected at each occurrence from the group:
  Cl, F, Br, I, $CF_3$, $CHF_2$, OH, =O, SH, —$CO_2R^{1b}$, —$SO_2R^{1b}$, —$SO_3R^{1b}$, —$P(O)_2R^{1b}$, —$P(O)_3R^{1b}$, —$C(=O)NHR^{1b}$, —$NHC(=O)R^{1b}$, —$SO_2NHR^{1b}$, —$OR^{1b}$, —$SR^{1b}$, $C_1$–$C_3$ alkyl, $C_3$–$C_6$ cycloalkyl, $C_1$–$C_6$ alkoxy,
  aryl substituted with 0–5 $R^{1c}$,
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{1c}$;
$R^{1b}$ is H,
  $C_1$–$C_4$ alkyl substituted with 0–3 $R^{1c}$,
  $C_2$–$C_4$ alkenyl substituted with 0–3 $R^{1c}$,
  $C_2$–$C_4$ alkynyl substituted with 0–3 $R^{1c}$,
  $C_3$–$C_6$ cycloalkyl substituted with 0–5 $R^{1c}$,
  $C_3$–$C_6$ carbocyle substituted with 0–5 $R^{1c}$,
  aryl substituted with 0–5 $R^{1c}$,
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{1c}$;
$R^{1c}$ is selected at each occurrence from the group:
  $C_1$–$C_4$ alkyl, Cl, F, Br, I, OH, $C_1$–$C_4$ alkoxy, —CN, —$NO_2$, —$OR^{1d}$, $C(=O)OR^{1d}$, $NR^{1d}R^{1d}$, $CF_3$, $OCF_3$, and phenyl substituted with 0–3 $R^{1e}$;
$R^{1d}$ is H, methyl, ethyl, propyl, butyl or phenyl;
$R^{1e}$ is selected at each occurrence from the group:
  methyl, ethyl, Cl, F, Br, I, OH, methoxy, ethoxy, —CN, —$NO_2$, —C $(=O)OR^{1d}$, $NR^{1d}R^{1d}$, $CF_3$, and $OCF_3$;
$R^2$ is H;
$R^3$ is —$R^4$ or —$R^4$;
$R^4$ is selected from the group: H,
  $C_1$–$C_4$ alkyl substituted with 0–3 $R^{4a}$,
  $C_2$–$C_4$ alkenyl substituted with 0–3 $R^{4a}$,
  $C_2$–$C_4$ alkynyl substituted with 0–3 $R^{4a}$,
  $C_3$–$C_6$ substituted with 0–4 $R^{4b}$,
  aryl substituted with 0–5 $R^{4b}$,
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4b}$;
$R^{4a}$ is, at each occurrence, independently selected from:
  H, F, Cl, Br, I, —$NO_2$, —CN, —NCS, —$CF_3$, —$OCF_3$, —$CH_3$, —$OCH_3$, =OH, —$CO_2H$, phenyl, —$C(=NH)NH_2$, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, —$OR^{11a}$, —$SR^{11a}$, —$C(=O)R^{11a}$, —$S(=O)R^{11a}$, —$SO_2R^{11}$, —$SO_2NR^{11}R^{11}$, $C_1$–$C_4$ haloalkyl, $C_1$–$C_4$ haloalkoxy,
  $C_3$–$C_6$ cycloalkyl substituted with 0–4 $R^{4b}$,
  aryl substituted with 0–5 $R^{4b}$, and
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4b}$;
$R^{4b}$ is, at each occurrence, independently selected from:
  H, F, Cl, Br, I, —$NO_2$, —CN, —NCS, —$CF_3$, —$OCF_3$, —$CH_3$, —$OCH_3$, =O, OH, —$CO_2H$, phenyl, —$C(=NH)NH_2$, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, —$OR^{11a}$, —$SR^{11a}$, —$C(=O)R^{11a}$, —$S(=O)R^{11a}$, —$SO_2R^{11}$, —$SO_2NR^{11}R^{11}$, $C_1$–$C_4$ haloalkyl, $C_1$–$C_4$ haloalkoxy,
  $C_1$–$C_4$ alkyl substituted with 0–3 $R^{4c}$,
  $C_2$–$C_4$ alkenyl substituted with 0–3 $R^{4c}$,
  $C_2$–$C_4$ alkynyl substituted with 0–3 $R^{4c}$,
  $C_3$–$C_6$ cycloalkyl substituted with 0–4 $R^{4d}$,
  aryl substituted with 0–5 $R^{4d}$, and
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4d}$;
$R^{4c}$ is, at each occurrence, independently selected from:
  H, F, Cl, Br, I, —$NO_2$, —CN, —NCS, —$CF_3$, —$OCF_3$, —$CH_3$, —$OCH_3$, =O, OH, —$CO_2H$, phenyl, —$C(=NH)NH_2$, —$NH_2$, —$NH(CH_3)$, —$N(CH_3)_2$, —$CO_2R^{11}$, —$C(=O)NR^{11}R^{11}$, —$NHC(=O)R^{11}$, —$NR^{11}R^{11}$, $OR^{11a}$, —$SR^{11a}$, —$C(=O)R^{11a}$, —$S(=O)R^{11a}$, —$SO_2R^{11}$, —$SO_2NR^{11}R^{11}$, $C_1$–$C_4$ haloalkyl, $C_1$–$C_4$ haloalkoxy,
  $C_3$–$C_6$ cycloalkyl substituted with 0–4 $R^{4d}$,
  aryl substituted with 0–5 $R^{4d}$,
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4d}$;
$R^{4d}$ is, at each occurrence, independently selected from:
  H, F, Cl, Br, I, —$NO_2$, —CN, —NCS, —$CF_3$, —$OCF_3$, —$CH_3$, —$OCH_3$, OH, —$CO_2H$, phenyl, —$NH_2$, —NH (CH$_3$), —N(CH$_3$)$_2$, —CO$_2$R$^{11}$, —C(=O)NR$^{11}$R$^{11}$, —NHC(=O)R$^{11}$, —NR$^{11}$R$^{11}$, OR$^{11a}$, —SR$^{11a}$, C(=O)R$^{11a}$, —S(=O)R$^{11a}$, —SO$_2$R$^{11}$, —SO$_2$NR$^{11}$R$^{11}$, C$_1$–C$_4$ alkyl, C$_1$–C$_4$ alkoxy, C$_1$–C$_4$ haloalkyl, and C$_1$–C$_4$ haloalkoxy;

R$^6$ is H, Cl or Br;
R$^8$ is H;
R$^9$ is —S(=O)$_2$R$^{9a}$, —C(=O)R$^{9a}$, —C(=O)NHR$^{9a}$, —CH$_2$—R$^{9a}$, CH$_2$CH$_2$—R$^9$, or —CH$_2$CH$_2$CH$_2$—R$^{9a}$;

R$^{9a}$ is selected from the group: H
 C$_1$–C$_6$ alkyl substituted with 0–3 R$^{9b}$,
 C$_3$–C$_6$ cycloalkyl substituted with 0–3 R$^{9c}$ and
 aryl substituted with 0–3 R$^{9c}$ and
 5–10 membered heterocyclic group consisting of carbon atoms and 1–4 heteroatoms selected from the group:
  pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, moripholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 R$^{9c}$;

R$^{9b}$ is selected from the group:
 phenyl substituted with 0–3 R$^{9c}$,
 naphthyl substituted with 0–3 R$^{9c}$,
 benzyl substituted with 0–3 R$^{9c}$, and
 5–10 membered heterocyclic group consisting of carbon atoms and 1–4 heteroatoms selected from the group:
  pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 R$^{9c}$;

R$^{9c}$ is selected at each occurrence from the group:
 H, F, Cl, Br, I, —NO$_2$, —CN, —NCS, —CF$_3$, —OCF$_3$, —CH$_3$, —OCH$_3$, =O, OH, —CO$_2$H, phenyl, —NH$_2$, —NH(CH$_3$), —N(CH$_3$)$_2$, —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11}$, C$_1$–C$_4$ haloalkyl, C$_1$–C$_4$ haloalkoxy, C$_1$–C$_4$ alikyl substituted with 0–3 R$^{9d}$,
 C$_1$–C$_4$ alkoxy substituted with 0–3 R$^{9d}$,
 C$_3$–C$_6$ cycloalkyl substituted with 0–3 R$^{9d}$,
 aryl substituted with 0–5 R$^{9d}$, and
 5–6 membered heterocyclic group consisting of carbon atoms and 1–4 heteroatoms selected from the group:
  pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 R$^{9d}$;

R$^9$d is selected at each occurrence from the group:
 H, F, Cl, Br, I, —NO$_2$, —CN, —NCS, —CF$_3$, —OCF$_3$, —CH$_3$, —OCH$_3$, =O, OH, —CO$_2$H, phenyl, —NH$_2$, —NH(CH$_3$), —N(CH$_3$)$_2$, —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11}$, C$_1$–C$_4$ alkyl, C$_1$–C$_4$ alkoxy, C$_1$–C$_4$ haloalkyl, and C$_1$–C$_4$ haloalkoxy;

R$^{11}$ is, at each occurrence, independently H, methyl, ethyl propyl, or butyl;
R$^{11a}$ is, at each occurrence, independently H, methyl, ethyl propyl, butyl, phenyl, naphthyl, or trifluoromethyl;
R$^{13}$ is H, methyl, ethyl, propyl, or butyl; and
q is 0, 1 or 2.

[8] In a further more preferred embodiment, the present invention provides novel compounds of Formula (IIa):

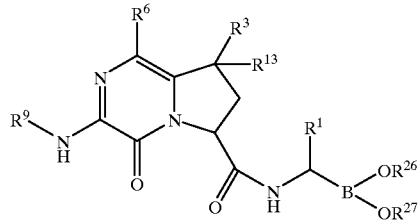

(IIa)

or a stereoisomer or pharmaceutically acceptable salt form thereof, wherein:
OR$^{26}$ and OR$^{27}$ are independently selected from:
 a) —OH,
 b) —F,
 c) methyloxy, ethyloxy, propyloxy, butyloxy, pentyloxy, or hexyloxy, and
when taken together, OR$^{26}$ and OR$^{27}$ form:
 d) pinandiol, pinacol, 1,2-ethanediol, 1,2-propanediol, 1,3-propanediol, 2,3-butanediol, 1,2-diisopropylethanediol, 5,6-decanediol, or 1,2-dicyclohexylethanediol;

R$^1$ is selected from the group: —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$C(CH$_3$)$_3$, —CH$_2$CH$_2$C(CH$_3$)$_3$, —CH$_2$CH$_2$CH$_2$C(CH$_3$)$_3$, —CH$_2$CH$_2$CH$_2$CH(CH$_3$)$_2$, —CH$_2$CH$_2$CH$_2$CH(CH$_2$CH$_3$)$_2$, —CH$_2$CH$_2$CH$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$CF$_3$, —CH$_2$CH$_2$CF$_3$, —CH$_2$CH$_2$CH$_2$CF$_3$, —CH$_2$CHF$_2$, —CH$_2$CH$_2$CHF$_2$, —CH$_2$CH$_2$CH$_2$CHF$_2$, —CH=CH$_2$, —CH$_2$CH=CH$_2$, —CH=CHCH$_3$, cis—CH$_2$CH=CH(CH$_3$), trans-CH$_2$CH=CH(CH$_3$), —CH$_2$CH$_2$CH=CH, —CH$_2$CH=C(CH$_3$)$_2$, —CH$_2$CH$_2$CH=C(CH$_3$)$_2$, —CH$_2$CO$_2$H, —CH$_2$CH$_2$CO$_2$H, —CH$_2$CO$_2$C(CH$_3$)$_3$, —CH$_2$CH$_2$CO$_2$C(CH$_3$)$_3$, —CH$_2$CH$_2$CH$_2$CH$_2$NH$_2$, phenyl, benzyl, phenethyl, phenpropyl, phenbutyl, (2-methylphenyl)ethyl-, (3-methylphenyl)ethyl-, (4-methylphenyl)ethyl-, (4-ethylphenyl)ethyl-, (4-i-propylphenyl)ethyl-, (4-t-butylphenyl)ethyl-, (4-hydroxyphenyl)ethyl-, (4-phenyl-phenyl)ethyl-, (4-phenoxy-phenyl)ethyl-, (4-cyclohexyl-phenyl)-ethyl -, (4-cyclopropyl-phenyl)ethyl-, (2,5-dimethylphenyl)ethyl-, (2,4-dimethylphenyl)ethyl-, (2,6-difluorophenyl)ethyl-, (4-cyclopentyl-phenyl) ethyl-, (4-cyclobutyl-phenyl)ethyl-, (2-trifluoromethylphenyl)ethyl-, (3-trifluoromethylphenyl)ethyl-, (4-trifluoromethylphenyl)ethyl-, (2-fluorophenyl) ethyl-, (3-fluorophenyl)ethyl-, (4-fluorophenyl)ethyl-, (2-chlorophenyl)ethyl-, (3-chlorophenyl)ethyl-, (4-chlorophenyl)ethyl-, (2-bromophenyl)ethyl-, (3-bromophenyl)ethyl-, (4-bromophenyl)ethyl-, (2,3,4,5,6-pentafluorophenyl)ethyl-(naphth-2-yl)ethyl, (cyclobutyl)methyl, (cyclobutyl)ethyl, (cyclobutyl) propyl, cyclopropyl, cyclobutyl, cyclopentyl, and cyclohexyl;

$R^3$ is selected from the group: methyl, ethyl, propyl, butyl, pentyl, hexyl, phenylmethyl, phenylethyl, phenylpropyl, (cyclopropyl)methyl, (cyclopropyl) ethyl, (cyclopropyl)propyl, (cyclohexyl)methyl, (cyclohexyl)ethyl, (cyclohexyl)propyl, (3-methylphenyl)methyl-, (4-methylphenyl)methyl-, (3-$CF_3$-phenyl)methyl-, (4-$CF_3$-phenyl)methyl-, (3-methoxyphenyl)methyl-, (4-methoxyphenyl) methyl-, phenylmethyl-O-, phenylethyl-O-, (naphth-1-yl)methyl-O-, and (naphth-2-yl)methyl-O-;

$R^6$ is H or Cl;

$R^9$ is selected from the group: methyl, ethyl, propyl, butyl, pentyl, hexyl, trifluoromethyl, phenylmethyl, phenylethyl, phenylpropyl, (3-phenyl-phenyl)methyl-, (4-phenyl-phenyl)methyl-, (2-methylphenyl)methyl-, (3-methylphenyl)methyl-, (4-methylphenyl)methyl-, (2-fluorophenyl)methyl-, (3-fluorophenyl)methyl-, (4-fluorophenyl)methyl-, (2-chlorophenyl)methyl-, (3-chlorophenyl)methyl-, (4-chlorophenyl)methyl-, (2-bromophenyl)methyl-, (3-bromophenyl)methyl-, (4-bromophenyl)methyl-, (2-cyanophenyl)methyl-, (3-cyanophenyl)methyl-, (4-cyanophenyl)methyl-, (2-nitrophenyl)methyl-, (3-nitrophenyl)methyl-, (4-nitrophenyl)methyl-, (2-aminophenyl)methyl-, (3-aminophenyl)methyl-, (4-aminophenyl)methyl-, (2-$CF_3SO_2$-phenyl)methyl-, (3-$CF_3SO_2$-phenyl) methyl-, (4-$CF_3SO_2$-phenyl)methyl-, (2-$CF_3$-phenyl) methyl-, (3-$CF_3$-phenyl)methyl-, (4-$CF_3$-phenyl) methyl-, (2-methoxyphenyl)methyl-, (3-methoxyphenyl)methyl-, (4-methoxyphenyl) methyl-, (2-$CF_3O$-phenyl)methyl-, (3-$CF_3O$-phenyl) methyl-, (4-$CF_3O$-phenyl)methyl-, (2-$CF_3S$-phenyl) methyl-, (3-$CF_3S$-phenyl)methyl-, (4-$CF_3S$-phenyl) methyl-, (3,5-di$CF_3$-phenyl)methyl-, (3,4-di$CF_3$-phenyl)methyl-, (3,5-diCl-phenyl)methyl-, (2,5-diCl-phenyl)methyl-, (3,4-diCl-phenyl)methyl-, (3,5-diF-phenyl)methyl-, (2,5-diF-phenyl)methyl-, (3,4-diF-phenyl)methyl-, (2-furanyl)methyl-, (3-furanyl) methyl-, (2-pyridyl)methyl-, (3-pyridyl)methyl-, (4-pyridyl)methyl-, (1,3-benzodioxolo-5-yl)methyl-, (cyclopropyl)methyl-, (cyclobutyl)methyl-, (cyclopentyl)methyl-, and (cyclohexyl)methyl-; $R^{11}$ is, at each occurrence, independently H, methyl, ethyl propyl, or butyl; $R^{11a}$ is, at each occurrence, independently H, methyl, ethyl propyl, butyl, or trifluoromethyl;

$R^{13}$ is H or methyl; and q is 0, 1 or 2.

[9] In a more preferred embodiment, the present invention provides a compound selected from the group:

(6S,8R)- N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[4-methoxyphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2,5-difluorophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-methylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)thiophenyl]methyl]-amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3,4-difluorophenyl]methyl]amino]-pyrrolo[1,2-a]pyrazine-6-carboxamide;

(6S, 8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3,5-bis(trifluoromethyl)phenyl]methyl]-amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[1,3-benzodioxolo-5-methyl]amino]-pyrrolo[1,2-a]pyrazine-6-carboxamide;

(6S, 8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-phenylpropyl)-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-biphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-nitro-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2-furanyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3- butenyl]-1-chloro-4,6,7,8-tetrahydro-4-oxo-8-(3-phenylpropyl)-3-[1-hexyl]amino]-pyrrolo(1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[(methyl)amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[phenylmethyl]amino]-pyrrolo(1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-fluoro-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-chloro-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-methoxy-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[4-methoxy-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-cyano-phenyl]methyl]amino]-pyrrolo [1,2-a]-pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-benzyl-3-[[[3-trifluromethyl-phenyl]methyl]amino]-pyrrolo[1,2-a]pyrazine-6 -carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-naphthylmethyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-dimethylethylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-methylbenzyl)-3-[[[3-trifluromethyl-phenyl]methyl]amino]-pyrrolo(1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-trifluoromethylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-benzyl-3-[[[3-cyano-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-methylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3,5-dimethylbenzyl)-3-(([3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-methoxybenzyl)-3-[[[3-trifluromethyl-phenyl]methyl]amino]-pyrrolo[1,2-a]pyrazine-6-carboxamide;

(6S)-1-chloro-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8,8-dimethyl-4-oxo-3-[[[3-(trifluoromethyl)phenyl]methyl]amino]pyrrolo[1,2-a]pyrazine-6-carboxamide;

(6S,8R)-1-chloro-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S,8S)-1-chloro-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S)-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8,8-dimethyl-4-oxo-3-[[[3-(trifluoromethyl)phenyl]methyl]amino]pyrrolo[1,2-a]pyrazine-6-carboxamide;

(6S,8R)-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S,8S)-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S)-1-chloro-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-4-oxo-8,8-di(3-phenylpropyl)-3-[[[3-(trifluoromethyl)phenyl]methyl]amino]pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-naphthylmethoxy)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-(4-trifluoromethylphenylethyl)]-1-chloro-4,6,7,8-tetrahydro-4-oxo-8-(3-methoxybenzyl)-3-[[[3-trifluromethyl-phenyl]methyl]amino]-pyrrolo[1, 2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-(2-naphthyl)propyl)-3-[[[3-trifluromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-ethyl]-1-chloro-4,6,7,8-tetrahydro-4-oxo-8-(3-(2-naphthyl)propyl)-3-[[[3-trifluromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-(2-naphthyl)propyl)-3-[[[3-trifluromethylthiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-ethyl]-1-chloro-4,6,7,8-tetrahydro-4-oxo-8-(3-(2-naphthyl)propyl)-3-[[[3-trifluromethylthiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-(2-naphthyl)propyl)-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-(2-naphthyl)propyl)-3-[[[3-trifluoromethylthiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[2-propyl]amino]-pyrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-(2-methylpropyl)amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-(cyclohexylmethyl)amino]-pyrrolo[1,2-]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-trifluoromethoxyphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2-difluoromethoxyphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2-pyridinyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[4-pyridinyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-pyridinyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[5-methyl-2-pyrazinyl)methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-4-oxo-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[tert-butoxylcarbonyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[(2-tert-butoxylcarbonyl)ethyl]amino]-pyrrolo[1,2-a]pyrazine-6-carboxamide;

[(1R-1-[[[(6S,8R)-1-chloro-4,6,7,8-tetrahydro-4-oxo-8-(3-phenylpropyl)-3-[[[3-(trifluoromethyl)phenyl]methyl]-amino]pyrrolo[1,2-a]pyrazin-6-yl]carbonyl]amino]-3-butenyl]-boronic acid;

[(1R-1-[[[(6S,8R)-1-chloro-4,6,7,8-tetrahydro-4-oxo-8-[3-(2-naphthyl)propyl]-3-[[[3-(trifluoromethyl)phenyl]methyl]-amino]pyrrolo[1,2-a]pyrazin-6-yl]carbonyl]amino]-3-butenyl]-boronic acid; and

[(1R-1-[[[(6S,8R)-1-chloro-4,6,7,8-tetrahydro-4-oxo-8-[3-(2-naphthyl)propyl]-3-[[[3-(trifluoromethyl)phenyl]methyl]-amino]pyrrolo[1,2-a]pyrazin-6-yl]carbonyl]amino]-3-ethyl]-boronic acid.

In a particularly preferred embodiment, the present invention provides compounds of Formula (II-r)

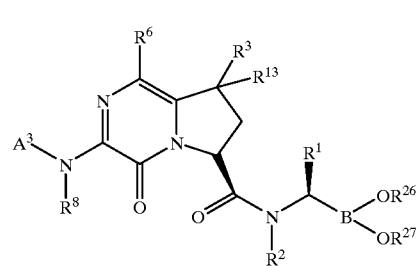

(II-r)

or pharmaceutically acceptable salt form thereof.

In a more particularly preferred embodiment, the present invention provides compounds of Formula (IIa-r):

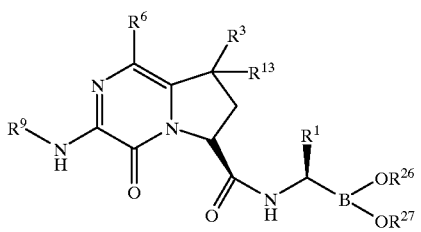

(IIa-r)

or pharmaceutically acceptable salt form thereof.

In another embodiment, the present invention provides a novel pharmaceutical composition comprising a pharmaceutically acceptable carrier and a therapeutically effective amount of a compound of Formula (I), (Ia), (Ib), (Ic), (II), (IIa) or pharmaceutically acceptable salt form thereof.

In another embodiment, the present invention provides a novel method of treating HCV infection which comprises administering to a host in need of such treatment a therapeutically effective amount of a compound of Formula Formula (I), (Ia), (Ib), (Ic), (II), (IIa) or pharmaceutically acceptable salt form thereof.

In another embodiment, the present invention provides novel compounds of Formula (I), (Ia), (Ib), (Ic), (II), (IIa) or pharmaceutically acceptable salt forms thereof for use in therapy.

In another embodiment, the present invention provides the use of novel compounds of Formula (I), (Ia), (Ib), (Ic), (II), (IIa) or pharmaceutically acceptable salt forms thereof for the manufacture of a medicament for the treatment of HCV.

DEFINITIONS

The compounds herein described have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^{1a}$) occurs more than one time in any constituent or formula for a compound, its definition at each occurrence is independent of its definition at every other occurrence. Thus, for example, if a group is shown to be substituted with 0–3 $R^{1a}$, then said group may optionally be substituted with up to three $R^{1a}$ groups and $R^{1a}$ at each occurrence is selected independently from the definition of $R^{1a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$–$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. For example, "$C_1$–$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2 v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$–$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, and phenyl.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated partially unsaturated or unsaturated (ie. aromatic or "heteroaryl"), and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aryl", "$C_6$–$C_{10}$ aryl" or "aromatic residue", is intended to mean an aromatic moiety containing, if specified, the specified number of carbon atoms; for example phenyl, pyridinyl or naphthyl. Unless otherwise specified, "aryl", "$C_6$–$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. "Natural amino acids" include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-CBZ-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used throughout the specification, the following abbreviations for amino acid residues or amino acids apply:

Abu is L-aminobutyric acid;
Ala is L-alanine;
Alg is L-2-amino-4-pentenoic acid;
Ape is L-2-aminopentanoic acid;
Arg is L-arginine;
Asn is L-asparagine;
Asp is L-aspartic acid;
Aze is azedine-2-carboxlic acid;
Cha is L-2-amino-3-cyclohexylpropionic acid;
Cpa is L-2-amino-3-cyclopropylpropionic acid
Cpg is L-2-amino-2-cyclopropylacetic acid;
Cys is L-cysteine;
Dfb is L-4,4'-difluoro-1-amino-butyric acid;
Dpa is L-2-amino-3,3-diphenylpropionic acid
Gln is L-glutamine;
Glu is L-glutamic acid;
Gly is glycine;
His is L-histidine;
HomoLys is L-homolysine;
Hyp is L-4-hydroxyproline;
Ile is L-isoleucine;
Irg is isothiouronium analog of L-Arg;
Leu is L-leucine;
Lys is L-lysine;
Met is L-methionine;
Orn is L-ornithine;
Phe is L-phenylalanine;
Phe(4-fluoro) is para-fluorophenylalanine;
Pro is L-proline;

Sar is L-sarcosine;
Ser is L-serine;
Thr is L-threonine;
Tpa is L-2-amino-5,5,5-trifluoropentanoic acid;
Trp is L-tryptophan;
Tyr is L-tyrosine; and
Val is L-valine.

"Amino acid residue" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, His, Hyp, Ile, Irg Leu, Lys, Met, Orn, Phe, Phe(4-fluoro), Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose. Additionally, said reference describes, but does not extensively list, acylic N-alkyl and acyclic α,α-disubstituted amino acids. Included in the scope of the present invention are N-alkyl, aryl, and alkylaryl analogs of amino acid residues. Similarly, alkyl, aryl, and alkylaryl maybe substituted for the alpha hydrogen. Illustrated below are examples of N-alkyl and alpha alkyl amino acid residues, respectively.

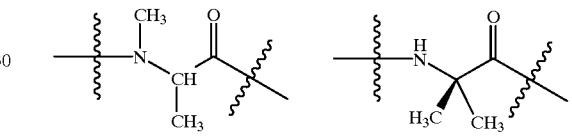

Unnatural amino acids that fall within the scope of "amino acid residue" are by way of example and without limitation: 2-aminobutanoicacid, 2-aminopentanoic acid, 2-aminohexanoic acid, 2-aminoheptanoicacid, 2-aminooctanoic acid, 2-aminononanoic acid, 2-aminodecanoic acid, 2-aminoundecanoic acid, 2-amino-3,3-dimethylbutanoic acid, 2-amino-4,4-dimethylpentanoic acid, 2-amino-3-methylhexanoic acid, 2-amino-3-methylheptanoic acid, 2-amino-3-methyloctanoic acid, 2-amino-3-methylnonanoic acid, 2-amino-4-methylhexanoic acid, 2-amino-3-ethylpentanoic acid, 2-amino-3,4-dimethylpentanoic acid, 2-amino-3,5-dimethylhexanoic acid, 2-amino-3,3-dimethylpentanoic acid, 2-amino-3-ethyl-3-methylpentanoic acid, 2-amino-3,3-diethylpentanoic acid, 2-amino-5-methylhexanoic acid, 2-amino-6-methylheptanoic, 2-amino-7-methyloctanoic, 2-amino-2-cyclopentylacetic, 2-amino-2-cylcohexylacetic acid, 2-amino-2-(1-methylcylcohexyl)acetic acid, 2-amino-2-(2-methyl-1-methylcylcohexyl)acetic acid, 2-amino-2-(3-methyl-1-methylcylcohexyl)acetic acid, 2-amino-2-(4-methyl-1-methylcylcohexyl)acetic acid, 2-amino-2-(1-ethylcycolhexyl)acetic acid, 2-amino-3-(cyclohexyl)propanoic acid, 2-amino-4-(cyclohexyl)butanoic acid, 2-amino-3-(1-adamantyl)propanoic acid, 2-amino-3-butenoic acid, 2-amino-3-methyl-3-butenoic acid, 2-amino-4-pentenoic acid, 2-amino-4-hexenoic acid, 2-amino-5-heptenoic acid, 2-amino-4-methyl-4-hexenoic acid, 2-amino-5-methyl-4-hexenoic acid, 2-amino-4-methy-5-hexenoic acid, 2-amino-6-heptenoic acid, 2-amino-3,3,4-trimethyl-4-pentenoic acid, 2-amino-4-chloro-4-pentenoic, 2-amino-4,4-dichloro-3-butenoic acid, 2-amino-3-(2-methylenecyclopropyl)-propanoic acid, 2-amino-2-(2-cyclopentenyl)acetic acid, 2-amino-2-(cyclohexenyl)acetic acid, 2-amino-3-(2-cyclopentenyl)propanoic acid, 2-amino-3-(3-cyclopentenyl)propanoic acid, 2-amino-3-(1-cyclohexyl)propanoic acid, 2-amino-2-(1-cyclopentenyl)acetic acid, 2-amino-2-(1-cylcohexyl)acetic acid, 2-amino-2-(1-cylcoheptenyl)acetic acid, 2-amino-2-(1-cyclooctenyl)acetic acid, 2-amino-3-(1-cycloheptenyl)propanoic acid, 2-amino-3-(1,4-cyclohexadienyl)propanoic acid, 2-amino-3-(2,5-cyclohexadienyl)propanoic acid, 2-amino-2-(7-cycloheptatrienyl)acetic acid, 2-amino-4,5-hexadienoic acid, 2-amino-3-butynoic acid, 2-amino-4-pentyoic acid, 2-amino-4-hexynoic acid, 2-amino-4-hepten-6-ynoic acid, 2-amino-3-fluoropropanoic acid, 2-amino-3,3,3-trifluoropropanoic acid, 2-amino-3-fluorobutanoic acid, 2-amino-3-fluoropentanoic acid, 2-amino-3-fluorohexanoic acid, 2-amino-3,3-difluorobutanoic acid, 2-amino-3,3-difluoro-3-phenylpropanoic acid, 2-amino-3-perfluoroethylpropanoic acid, 2-amino-3-perfluoropropylpropanoic acid, 2-amino-3-fluoro-3-methylbutanoic acid, 2-amino-3,5,5-trifluoropentanoic acid, 2-amino-3-methyl-4,4,4-trifluorobutanoic acid, 2-amino-3-trifluoromethyl-4,4,4-trifluorobutanoic acid, 2-amino-3,3,4,4,5,5-heptafluoropentanoic acid, 2-amino-3-methyl-5-fluoropentanoic acid, 2-amino-3-methyl-4-fluoropentanoic acid, 2-amino-5,5-difluorohexanoic acid, 2-amino-4-(fluoromethyl)-5-fluoropentanoic acid, 2-amino-4-trifluoromethyl-5,5,5-trifluoropentanoic acid, 2-amino-3-fluoro-3-methylbutanoic acid, 2-amino-3-fluoro-3-phenylpentanoic acid, 2-amino-2-(1-fluorocyclopentyl)acetic acid, 2-amino-2-(1-fluorocyclohexyl)acetic acid, 2-amino-3-chloropropanoic acid acid, 2-amino-3-chlorobutanoic acid acid, 2-amino-4,4-dichlorobutanoic acid acid, 2-amino4,4,4-trichlorobutanoic acid, 2-amino-3,4,4-trichlorobutanoic acid, 2-amino-6-chlorohexanoic acid, 2-amino-4-bromobutanoic acid, 2-amino-3-bromobutanoic acid, 2-amino-3-mercaptobutanoic acid, 2-amino-4-mercaptobutanoic acid, 2-amino-3-mercapto-3,3-dimethylpropanoic acid, 2-amino-3-mercapto-3-methylpentanoic acid, 2-amino-3-mercaptopentanoic acid, 2-amino-3-mercapto-4-methylpentanoic acid, 2-amino-3-methyl-4-mercaptopentanoic acid, 2-amino-5-mercapto-5-methylhexanoic acid, 2-amino-2-(1-mercaptocyclobutyl)acetic acid, 2-amino-2-(1-mercaptocyclopentyl)acetic acid, 2-amino-2-(1-mercaptocyclohexyl)acetic acid, 2-amino-5-(methylthio)pentanoic acid, 2-amino-6-(methylthio)hexanoic acid, 2-amino-4-methylthio-3-phenylbutanoic acid, 2-amino-5-ethylthio-5-methylpentanoic acid, 2-amino-5-ethylthio-3,5,5-trimethylpentanoic acid, 2-amino-5-ethylthio-5-phenylpentanoic acid, 2-amino-5-ethylthio-5-pentanoic acid, 2-amino-5-butylthio-5-methylpentanoic acid, 2-amino-5-butylthio-3,5,5-trimethylpentanoic acid, 2-amino-5-butylthio-5-phenylpentanoic acid, 2-amino-5-(butylthio)pentanoic acid, 2-amino-3-methy4-hydroselenopentanoic acid, 2-amino-4-methylselenobutanoic acid, 2-amino-4-ethylselenobutanoic acid, 2-amino-4-benzylselenobutanoic acid, 2-amino-3-methyl-4-(methylseleno)butanoic acid, 2-amino-3-(aminomethylseleno)propanoic acid, 2-amino-3-(3-aminopropylseleno)propanoic acid, 2-amino-4-methyltellurobutanoic acid, 2-amino-4-hydroxybutanoic acid, 2-amino-4-hydroxyhexanoic acid, 2-amino-3-hydroxypentanoic acid, 2-amino-3-hydroxyhexanoic acid, 2-amino-3methyl-4-hydroxybutanoic acid, 2-amino-3-hydroxy-3-methylbutanoic acid, 2-amino-6-hydroxyhexanoic acid, 2-amino-4-hydroxyhexanoic acid, 2-amino-3-hydroxy-4-methylpentanoic acid, 2-amino-3-hydroxy-3-methylpentanoic acid, 2-amino4-hydroxy-3,3-dimethylbutanoic acid, 2-amino-3-hydroxy4-methylpentanoic acid, 2-amino-3-hydroybutanedioic acid, 2-amino-3-hydroxy-3-phenyl-propanoic acid, 2-amino-3-hydroxy-3-(4-nitrophenyl)propanoic acid, 2-amino-3-hydroxy-3-(3-pyridyl)propanoic acid, 2-amino-2-(1-hydroxycyclopropyl)acetic acid, 2-amino-3-(1-hydroxycyclohexyl)propanoic acid, 2-amino-3-hydroxy-3-phenylpropanoic acid, 2-amino-3-hydroxy-3-[3-bis(2-chloroethyl)aminophenyl]propanoic acid, 2-amino-3-hydroxy-3-(3,4-dihydroxyphenyl)propanoic acid, 2-amino-3-hydroxy-3-(3,4-methylenedioxyphenyl)propanoic acid, 2-amino-4-fluoro-3-hydroxybutanoic acid, 2-amino-4,4,4-trichloro-3-hydroxybutanoic acid, 2-amino-3-hydroxy-4-hexynoic acid, 2-amino-3,4-dihydroxybutanoic acid, 2-amino-3,4,5,6-tetrahydroxyhexanoic acid, 2-amino-4,5-dihydroxy-3-methylpentanoic acid, 2-amino-5,6-dihydroxyhexanoic acid, 2-amino-5-hydroxy-4-(hydroxyrnethyl)pentanoic acid, 2-amino-4,5-dihydroxy-4-(hydroxymethyl)pentanoic acid, 2-amino-3-hydroxy-5-benzyloxypentanoic acid, 2-amino-3-(2-aminoethoxy)propanoic acid, 2-amino-4-(2-aminoethoxy)butanoic acid, 2-amino-4-oxobutanoic acid, 2-amino-3-oxobutanoic acid, 2-amino-4-methyl-3-oxopentanoic acid, 2-amino-3-phenyl-3-oxopropanoic acid, 2-amino-4-phenyl-3-oxobutanoic acid, 2-amino-3-methyl-4-oxopentanoic acid, 2-amino-4-oxo-4-(4-hydroxyphenyl)butanoic acid, 2-amino-4-oxo-4-(2-furyl)butanoic acid, 2-amino-4-oxo-4-(2-nitrophenyl)butanoic acid, 2-amino-4-oxo-4-(2-amino-4-chlorophenyl)butanoic acid, 2-amino-3-(4-oxo-1-cyclohexenyl)propanoic acid, 2-amino-3-(4-oxocyclohexanyl)propanoic acid, 2-amino-3-(2,5-dimethyl-3,6-dioxo-1,4-cydohexadienyl)propanoic acid, 2-amino-3-(1-hydroxy-5-methyl-7-oxo-cyclohepta-1,3,5-trien-2-yl)propanoic acid, 2-amino-3-(1-hydroxy-7-oxo-cyclohepta-1,3,5-trien-3-yl)propanoic acid, 2-amino-3-(1-hydroxy-7-oxo-cyclohepta-1,3,5-trien-4-yl)propanoic acid, 2-amino-4-methoxy-3-butenoic acid, 2-amino-4-(2-aminoethoxy)-3-butenoic acid, 2-amino-4-(2-amino-3-hydroxypropyl)-3-butenoic acid, 2-amino-2-(4-methoxy-1,4-cyclohexadienyl)acetic acid, 2-amino-3,3-diethoxypropanoic acid, 2-amino-4,4-dimethylbutanoic acid, 2-amino-2-(2,3-epoxycyclohexyl)acetic acid, 2-amino-3-(2,3-epoxycyclohexy)propanoic acid, 2-amino-8-oxo-9,10-epoxydecanoic acid, 2-amino-propanedioic acid, 2-amino-3-methylbutanedioic acid, 2-amino-3,3-dimethylbutanedioic acid, 2-amino4-methylpentanedioic acid, 2-amino-3-methylpentanedioic acid, 2-amino-3-phenylpentanedioic acid, 2-amino-3-hydroxypentanedioic acid, 2-amino-3-carboxypentanedioic acid, 2-amino-4-ethylpentanedioic acid, 2-amino-4-propylpentanedioic acid, 2-amino-4-isoamylpentanedioic acid, 2-amino-4-phenylpentanedioic acid, 2-amino-hexanedioic acid, 2-amino-heptanedioic acid, 2-amino-decanedioic acid, 2-amino-octanedioic acid, 2-amino-dodecanedioic acid, 2-amino-3-methylenebutanedioic acid, 2-amino-4-methylenepentanedioic acid, 2-amino-3-fluorobutanedioic acid, 2-amino-4-fluoropentanedioic acid, 2-amino-3,3-difluorobutanedioic acid, 2-amino-3-chloropentanedioic acid, 2-amino-3-hydroxybutanedioic acid, 2-amino-4-hydroxypentanedioic acid, 2-amino-4-hydroxyhexanedioic acid, 2-amino-3,4-dihydroxypentanedioic acid, 2-amino-3-(3-hydroxypropyl)butanedioic acid, 2-amino-3-(1-carboxy-4-hydroxy-2-cyclodienyl)propanoic acid, 2-amino-3-(aceto)butanedioic acid, 2-amino-3-cyanobutanedioic acid, 2-amino-3-(2-carboxy-6-oxo-6H-pyranyl)propanoic acid, 2-amino-3-carboxybutanedioic acid, 2-amino-4-carboxypentanedioic acid, 3-amido-2-amino-3-hydroxypropanoic acid, 3-amido-2-amino-3-methylpropanoic acid, 3-amido-2-amino-3-phenylpropanoic acid, 3-amido-2,3-diaminopropanoic acid, 3-amido-2-amino-3-[N-(4-hydroxyphenyl)amino]propanoic acid, 2,3-diaminopropanoic acid, 2,3-diaminobutanoic acid, 2,4-diaminobutanoic acid, 2,4-diamino-3-methylbutanoic acid, 2,4-diamino-3-phenylbutanoic acid, 2-amino-3-(methylamino)butanoic acid, 2,5-diamino-3-methylpentanoic acid, 2,7-diaminoheptanoic acid, 2,4-diaminoheptanoic acid, 2-amino-2-(2-piperidyl)acetic acid, 2-amino-2-(1-aminocyclohexyl)acetic acid, 2,3-diamino-3-phenylpropanoic acid, 2,3-diamino-3-(4-hydroxyphenyl)propanoic acid, 2,3-diamino-3-(4-methoxyphenyl)propanoic acid, 2,3-diamino-3-[4-(N,N'-dimethyamino)phenyl]propanoic acid, 2,3-diamino-3-(3,4-dimethoxyphenyl)propanoic acid, 2,3-diamino-3-(3,4-methylenedioxyphenyl)propanoic acid, 2,3-diamino-3-(4-hydroxy-3-methoxyphenyl)propanoic acid, 2,3-diamino-3-(2-phenylethyl)propanoic acid, 2,3-diamino-3-propylpropanoic acid, 2,6-diamino-4-hexenoic acid, 2,5-diamino-4-fluoropentanoic acid, 2,6-diamino-5-fluorohexanoic acid, 2,6-diamino-4-hexynoic acid, 2,6-diamino-5,5-difluorohexanoic acid, 2,6-diamino-5,5-dimethylhexanoic acid, 2,5-diamino-3-hydroxypentanoic acid, 2,6-diamino-3-hydroxyhexanoic acid, 2,5-diamino-4-hydroxypentanoic acid, 2,6-diamino-4-hydroxyhexanoic acid, 2,6-diamino-4-oxohexanoic acid, 2,7-diaminooctanedioic acid, 2,6-diamino-3-carboxyhexanoic acid, 2,5-diamino-4-carboxypentanoic acid, 2-amino-4-(2-(N,N'-diethylamino)ethyl)pentandioic acid, 2-amino-4-(N,N'-diethylamino)pentandioic acid, 2-amino-4-(N-morpholino)pentandioic acid, 2-amino-4-(N,N'-bis(2-chloroethyl)amino)pentandioic acid, 2-amino-4-(N,N'-bis(2-hydroxyethyl)amino)pentandioic acid, 2,3,5-triaminopentanoic acid, 2-amino-3-(N-(2-aminethyl)amino)propanoic acid, 2-amino-3-((2-aminoethyl)seleno)propanoic acid, 2-amino-3-[(2-aminoethyl)thio]propanoic acid, 2-amino4-aminooxybutanoic acid, 2-amino-5-hydroxyaminopentanoic acid, 2-amino-5-[N-(5-nitro-2-pyrimidinyl)amino]pentanoic acid, 2-amino-4-[(7-nitro-2,1,3-benzoxadiazol-4-yl)amino]butanoic acid, 2-amino-3-guanidinopropanoic acid, 2-amino-3-guanidinobutanoic acid, 2-amino-4-guanidobutanoic acid, 2-amino-6-guanidohexanoic acid, 2-amino-6-ureidohexanoic acid, 2-amino-3-(2-iminoimidiazolin-4-yl)propanoic acid, 2-amino-2-(2-iminohexahydropyrimidin-4-yl)acetic acid, 2-amino-3-(2-iminohexahydropyrimidiny-4-yl)propanoic acid, 2-amino4-fluoro-5-guanidopentanoic acid, 2-amino-4-hydroxy-5-guanidopentanoic acid, 2-amino-4-guanidooxybutanoic acid, 2-amino-6-amidinohexanoic acid, 2-amino-5-(N-acetimidoylamino)pentanoic acid, 1-aminocyclopropanecarboxylic acid, 1-amino4-ethylcyclpropanecarboxylic acid, 1-aminocyclo- pentanecarboxylic acid, 1-aminocyclopentanecarboxylic acid, 1-amino-2,2,5,5-tetramethyl-cyclohexanecarboxylic acid, 1-aminocydoheptanecarboxylic acid, 1-aminocyclononanecarboxylic acid, 2-aminoindan-2-carboxylic acid, 2-aminonorbornane-2-carboxylic acid, 2-amino-3-phenylnorbornane-2-carboxylic acid, 3-aminotetrahydrothiophene-3-carboxylic acid, 1-amino-1,3-cyclohexanedicarboxylic acid, 3-aminopyrrolidine-3-carboxylic acid, 1,4-diaminocyclohexanecarboxylic acid, 6-alkoxy-3-amino-1,2,3,4-tetrahydrocarbazole-3-carboxylic acid, 2-aminobenzobicyclo[2,2,2]octane-2-carboxylic acid, 2-aminoindan-2-carboxylic acid, 1-amino-2-(3,4-dhydroxyphenyl)cyclopropanecarboxylic acid, 5,6-dialkoxy-2-aminoindane-2-carboxylic acid, 4,5-dihydroxy-2-aminoindan-2-caroxylic acid, 5,6-dihydroxy-2-aminotetralin-2-carboxylic acid, 2-amino-2-cyanoacetic acid, 2-amino-3-cyanopropanoic acid, 2-amino-4-cyanobutanoic acid, 2-amino-5-nitropentanoic acid, 2-amino-6-nitrohexanoic acid, 2-amino-4-aminooxybutanoic acid, 2-amino-3-(N-nitrosohydroxyamino)propanoic acid, 2-amino-3-ureidopropanoic acid, 2-amino-4-ureidobutanoic acid, 2-amino-3-phosphopropanoic acid, 2-amino-3-thiophosphopropanoic acid, 2-amino-4-methanephosphonylbutanoic acid, 2-amino-3-(trimethylsilyl)propanoic acid, 2-amino-3-(dimethyl(trimethylsilylmethylsilyl)propanoic acid, 2-amino-2-phenylacetic acid, 2-amino-2-(3-chlorophenyl)acetic acid, 2-amino-2-(4-chlorophenyl)acetic acid, 2-amino-2-(3-fluorophenyl)acetic acid, 2-amino-2-(3-methylphenyl)acetic acid, 2-amino-2-(4-fluorophenyl)acetic acid, 2-amino-2-(4-methylphenyl)acetic acid, 2-amino-2-(4-methoxyphenyl)acetic acid, 2-amino-2-(2-fluorophenyl)acetic acid, 2-amino-2-(2-methylphenyl)acetic acid, 2-amino-2-(4-chloromethylphenyl)acetic acid, 2-amino-2-(4-hydroxymethylphenyl)acetic acid, 2-amino-2-[4-(methylthiomethyl)phenyl]acetic acid, 2-amino-2-(4-bromomethylphenyl)acetic acid, 2-amino-2-(4-(methoxymethy)phenyl)acetic acid, 2-amino-2-(4-((N-benzylamino)methyl)phenyl)acetic acid, 2-amino-2-(4-hydroxylphenyl)acetic acid, 2-amino-2-(3-hydroxylphenyl)acetic acid, 2-amino-2-(3-carboxyphenyl)acetic acid, 2-amino-2-(4-aminophenyl)acetic acid, 2-amino-2-(4-azidophenyl)acetic acid, 2-amino-2-(3-t-butyl-4-hydroxyphenyl)acetic acid, 2-amino-2-(3,5-difluoro-4-hydroxyphenyl)acetic acid, 2-amino-2-(3,5-dihydroxyphenyl)acetic acid, 2-amino-2-(3-carboxy-4-hydroxyphenyl)acetic acid, 2-amino-2-(3,5-di-t-butyl-4-hydroxyphenyl)acetic acid, 2-amino-3-(2-methylphenyl)propanoic acid, 2-amino-3-(4-ethylphenyl)propanoic acid, 2-amino-3-(4-phenylphenyl)propanoic acid, 2-amino-3-(4-benzylphenyl)propanoic acid, 2-amino-3-(3-fluorophenyl)propanoic acid, 2-amino-3-(4-methylphenyl)propanoic acid, 2-amino-3-(4-fluorophenyl)propanoic acid, 2-amino-3-(4-chlorophenyl)propanoic acid, 2-amino-3-(2-chlorophenyl)propanoic acid, 2-amino-3-(4-bromophenyl)propanoic acid, 2-amino-3-(2-bromophenyl)propanoic acid, 2-amino-3-(3-hydroxyphenyl)propanoic acid, 2-amino-3-(2-hydroxyphenyl)propanoic acid, 2-amino-3-(4-mercaptophenyl)propanoic acid, 2-amino-3-(3-trifluoromethylphenyl)propanoic acid, 2-amino-3-(3-hydroxyphenyl)propanoic acid, 2-amino-3-(4-hydroxyphenyl)propanoic acid, 2-amino-3-(4-(hydroxymethy)phenyl]propanoic acid, 2-amino-3-[3-(hydroxyethyl)phenyl]propanoic acid, 2-amino-3-[3-(aminomethyl)phenyl]propanoic acid, 2-amino-3-(3-carboxyphenyl)propanoic acid, 2-amino-3-(4-nitrophenyl)propanoic acid, 2-amino-3-(4-aminophenyl)propanoic acid, 2-amino-3-(4-azidophenyl)propanoic acid, 2-amino-3-(4-cyanophenyl)propanoic acid, 2-amino-3-(4-acetophenyl)propanoic acid, 2-amino-3-(4-guanidinophenyl)propanoic acid, 2-amino-3-[4-(phenylazo)phenyl]propanoic acid, 2-amino-3-[4-(2-phenylethylenyl)phenyl]propanoic acid, 2-amino-3-(4-trialkylsilylphenyl)propanoic acid, 2-amino -3-(2,4-dimethylphenyl)propanoic acid, 2-amino-3-(2,3-dimethylphenyl)propanoic acid, 2-amino-3-(2,5-dimethylphenyl)propanoic acid, 2-amino-3-(3,5-dimethylphenyl)propanoic acid, 2-amino-3-(2,4,6-trimethylphenyl)propanoic acid, 2-amino-3-(3,4,5-trimethylphenyl)propanoic acid, 2-amino-3-(2,3,4,5,6-pentamethylphenyl)propanoic acid, 2-amino-3-(2,4,-difluorophenyl)propanoic acid, 2-amino-3-(3,4,- difluorophenyl)propanoic acid, 2-amino-3-(2,5,-difluorophenyl)propanoic acid, 2-amino-3-(2,6,-difluorophenyl)propanoic acid, 2-amino-3-(2,3,5,6-tetrafluorophenyl)propanoic acid, 2-amino-3-(3,5-dichloro-2,4,6-trifluorophenyl)propanoic acid, 2-amino-3-(2,3-difluorophenyl)propanoic acid, 2-amino-3-(2,3-bistrifluoromethylphenyl)propanoic acid, 2-amino-3-(2,4-bistrifluoromethylphenyl)propanoic acid, 2-amino-3-(2-chloro-5-trifluoromethylphenyl)propanoic acid, 2-amino-3-(2,5-difluorophenyl)propanoic acid, 2-amino-3-(2,3,4,5,6-pentafluorophenyl)propanoic acid, 2-amino-3-(2,3-dibromophenyl)propanoic acid, 2-amino-3-(2,5-dibromophenyl)propanoic acid, 2-amino-3-(3,4-dibromophenyl)propanoic acid, 2-amino-3-(3,4,5-triiodophenyl)propanoic acid, 2-amino-3-(2,3-dihydroxyphenyl)propanoic acid, 2-amino-3-(2,5-dihydroxyphenyl)propanoic acid, 2-amino-3-(2,6-dihydroxyphenyl)propanoic acid, 2-amino-3-(3-bromo-5-methoxyphenyl)propanoic acid, 2-amino-3-(2,5-dimethoxyphenyl)propanoic acid, 2-amino-3-(2,5-dimethoxy-4-methylphenyl)propanoic acid, 2-amino-3-(4-bromo-2,5-dimethoxyphenyl)propanoic acid, 2-amino-3-(3-carboxy-4-hydroxyphenyl)propanoic acid, 2-amino-3-(3-carboxy-4-aminophenyl)propanoic acid, 2-amino-3-(2-hydroxy-5-nitrophenyl)propanoic acid, 2-amino-3-(2-ethoxy-5-nitrophenyl)propanoic acid, 2-amino-3-(3,4,5-trimethoxyphenyl)propanoic acid, 2-amino-3-(4-azido-2-nitrophenyl)propanoic acid, 2-amino-3-(2-hydroxy-5-nitrophenyl)propanoic acid, 2-amino-3-(2,4-bis-trimethylsilylphenyl)propanoic acid, 2-amino-3-(4-hydroxy-3,5-di-t-butylphenyl)propanoic acid, 2-amino-3-(4-hydroxy-3-benzylphenyl)propanoic acid, 2-amino-3-(4-hydroxy-3-fluorophenyl)propanoic acid, 2-amino-3-(4-hydroxy-2,3,5,6-tetrafluorophenyl)propanoic acid, 2-amino-3-(4-hydroxy-3,5-dichlorophenyl)propanoic acid, 2-amino-3-(4-hydroxy-3-iodophenyl)propanoic acid, 2-amino-3-(4-hydroxy-3,5-diiodophenyl)propanoic acid, 2-amino-3-(4-hydroxy-2-hydroxyphenyl)propanoic acid, 2-amino-3-(4-hydroxy-3-hydroxymethylphenyl)propanoic acid, 2-amino-3-(4-hydroxy-2-hydroxy-6-methylphenyl)propanoic acid, 2-amino-3-(4-hydroxy-3-carboxyphenyl)propanoic acid, 2-amino-3-(4hydroxy-3,5-dinitrophenyl)propanoic acid, substituted thyronines, 2-amino-3-(3,4-dihydroxy-2-chlorophenyl)propanoic acid, 2-amino-3-(3,4-dihydroxy-2-bromophenyl)propanoic acid, 2-amino-3-(3,4-dihydroxy-2-fluorophenyl)propanoic acid, 2-amino-3-(3,4-dihydroxy-2-nitrophenyl)propanoic acid, 2-amino-3-(3,4-dihydroxy-2-methylphenyl)propanoic acid, 2-amino-3-(3,4-dihydroxy-2-ethylphenyl)propanoic acid, 2-amino-3-(3,4-dihydroxy-2-isopropylphenyl)propanoic acid, 2-amino-3-(2-t-butyl-4,5-dihydroxyphenyl)propanoic acid, 2-amino-3-(3-fluoro-4,5-dihydroxyphenyl)propanoic acid, 2-amino-3-(2-fluoro-4,5-dihydroxyphenyl)propanoic acid, 2-amino-3-(2,5,6-trifluoro-3,4-dihydroxyphenyl)propanoic acid, 2-amino-3-(2,6-dibromo-3,4-dihydroxyphenyl)propanoic acid, 2-amino-3-(5,6-dibromo-3,4-dihydroxyphenyl)propanoic acid, 2-amino-3-(2,4,5-trihydroxyphenyl)propanoic acid, 2-amino-3-(2,3,4-trihydroxyphenyl)propanoic acid, 2-amino-3-(3,4-dihydroxy-5-methoxyphenyl)propanoic acid, 2-amino-3-methyl-3-phenylpropanoic acid, 2-amino-3-ethyl-3-phenylpropanoic acid, 2-amino-3-isopropyl-3-phenylpropanoic acid, 2-amino-3-butyl-3-phenylpropanoic acid, 2-amino-3-benzyl-3-phenylpropanoic acid, 2-amino-3-phenylethyl-3-phenylpropanoic acid, 2-amino-3-(4-chlorophenyl)-3-phenylpropanoic acid, 2-amino-3-(4-methoxyphenyl)-3-phenylpropanoic acid, 2-amino-3,3-diphenylpropanoic acid, 2-amino-3-[4-(N,N- diethylamino) phenyl]heptanoic acid, 2-amino-3-[4-(N,N-diethylamino) phenyl]pentanoic acid, 2-amino-3-(3,4-dimethoxyphenyl) pentanoic acid, 2-amino-3-(3,4-dihydroxyphenyl)pentanoic acid, 2-amino-3-methyl-3-phenylbutanoic acid, 2-amino-3-ethyl-3-phenylpentanoic acid, 2-amino-3-methyl-3-phenylpentanoic acid, 2-amino-3,3-diphenylbutanoic acid, 2-amino-3-fluoro-3-phenylpropanoic acid, 2-amino-3-methylene-3-phenylpropanoic acid, 2-amino-3-methylmercapto-3-phenylpropanoic acid, 2-amino-4-methylmercapto-4-phenylbutanoic acid, 2-amino-4-(3,4-dihydroxyphenyl)butanoic acid, 2-amino-5-(4-methoxyphenyl)pentanoic acid, 2-amino-4-phenylbutanoic acid, 2-amino-5-phenylpentanoic acid, 2-amino-3,3-dimethyl-5-phenylpentanoic acid, 2-amino-4-phenyl-3-butenoic acid, 2-amino-4-phenoxybutanoic acid, 2-amino-5-phenoxypentanoic acid, 2-amino-2-(indanyl)acetic acid, 2-amino-2-(1-tetralyl)acetic acid, 2-amino-4,4-diphenylbutanoic acid, 2-amino-2-(2-naphthyl)acetic acid, 2-amino-3-(1-naphthyl)propanoic acid, 2-amino-3-(1-naphthyl)pentanoic acid, 2-amino-3-(2-naphthyl)propanoic acid, 2-amino-3-(1-chloro-2-naphthyl)propanoic acid, 2-amino-3-(1-bromo-2-naphthyDpropanoic acid, 2-amino-3-(4-hydroxy-1-naphthyl)propanoic acid, 2-amino-3-(4-methoxy-1-naphthyl)propanoic acid, 2-amino-3-(4-hydroxy-2-chloro-1-naphthyl)propanoic acid, 2-amino-3-(2-chloro-4-methoxy-1-naphthyl)propanoic acid, 2-amino-2-(2-anthryl)acetic acid, 2-amino-3-(9-anthryl)propanoic acid, 2-amino-3-(2-fluorenyl)propanoic acid, 2-amino-3-(4-fluorenyl)propanoic acid, 2-amino-3-(carboranyl)propanoic acid, 3-methylproline, 4-methylproline, 5-methylproline, 4,4-dimethylproline, 4-fluoroproline, 4,4-difluoroproline, 4-bromoproline, 4-chloroproline, 4-aminoproline, 3,4-dehydroproline, 4-methylproline, 4-methyleneproline, 4-mercaptoproline, 4-(4-methoxybenzylmercapto)proline, 4-hydroxymethylproline, 3-hydroxyproline, 3-hydroxy-5-methylproline, 3,4-dihydroxyproline, 3-phenoxyproline, 2-aminoproline, 5-aminoproline, 3-carbamylalkylproline, 4-cyano-5-methyl-5-carboxyproline, 4,5-dicarboxyl-5-methylproline, 2-aziridinecarboxylic acid, 2-azetidinecarboxylic acid, 4-methyl-2-azetidinecarboxylic acid, pipecolic acid, 1,2,3,6-tetrahydropicolinic acid, 3,4-methyleneproline, 2.4-methyleneproline, 4-aminopipecolic acid, 5-hydroxypipecolic acid, 4,5-dihydroxypipecolic acid, 5,6-dihydroxy-2,3-dihydroindole-2-carboxylic acid, 1,2,3 4-tetrahydroquinoline-2-carboxylic acid, 6,7-dihydroxy-1,2,3,4-tetrahydroisoquinoline-3-carboxylic acid, 6-hydroxy-1-methyl-1,2,3,4-tetrahydroisoquinoline-3-carboxylic acid, 6,7-dihydroxy-1-methyl-1,2,3,4-tetrahydroisoquinoline-3-carboxylic acid, 1,3-oxazolidine-4-carboxylic acid, 1,2-oxazolidine-3-carboxylic acid, perhydro-1,4-thiazine-3-carboxylic acid, 2,2-dimethylthiazolidine-4-carboxylic acid, perhydro-1,3-thlazine-2-carboxylic acid, selenazolidine4-carboxylic acid, 2-phenylthiazolidine4-carboxylic acid, 2-(4-carboxylicyl)thiazolidine-4-carboxylic acid, 1,2,3,4,4a, 9a-hexahydro-beta-carboline-3-carboxylic acid, 2,3,3a,8a-tetrahydropyrrolo(2,3b)indole-2-carboxylic acid, 2-amino-3-(2-pyridyl)propanoic acid, 2-amino-3-(3-pyridyl) propanoic acid, 2-amino-3-(4-pyridyl)propanoic acid, 2-amino-3-(2-bromo-3-pyridyl)propanoic acid, 2-amino-3-(2-bromo-4-pyridyl)propanoic acid, 2-amino-3-(2-bromo-5-pyridyl)propanoic acid, 2-amino-3-(2-bromo-6-pyridyl) propanoic acid, 2-amino-3-(2-chloro-3-pyridyl)propanoic acid, 2-amino-3-(2-chloro-4-pyridyl)propanoic acid, 2-amino-3-(2-chloro-5-pyridyl)propanoic acid, 2-amino-3-(2-chloro-6-pyridyl)propanoic acid, 2-amino-3-(2-fluoro-3-pyridyl)propanoic acid, 2-amino-3-(2-fluoro-4-pyridyl) loropanoic acid, 2-amino-3-(2-fluoro-5-pyridyl)propanoic acid, 2-amino-3-(2-fluoro-6-pyridyl)proloanoic acid, 2-amino-3-(1,2-dihydro-2-oxo-3-pyridyl)propanoic acid, 2-amino-3-(1,2-dihydro-2-oxo4-pyridyl)propanoic acid, 2-amino-3-(1,2-dihydro-2-oxo-5-pyridyl)propanoic acid, 2-amino-3-(1,2-dihydro-2-oxo-6-pyridyl)propanoic acid, 2-amino-3-(5-hydroxy-2-pyridyl)propanoic acid, 2-amino-3-(5-hydroxy-6-iodo-2-pyridyl)propanoic acid, 2-amino-3-(3-hydroxy-4-oxo-1,4dihydro-1-pyridyl)propanoic acid, N-(5-caroxyl-5-aminopentyl)pyridinium chloride, 1,2,5-trimethyl-4-(2-amino-2-carboxy-1-hydroxyethyl) pyridinium chloride, 2-amino-2-(5-chloro-2-pyridyl)acetic acid, N-(3-amino -3-carboxypropyl)pyridinium chloride, 2-amino -3-(2-pyrryl)propanoic acid, 2-amino-3-(1-pyrryl) propanoic acid, 2-amino-4-(1-pyrryl)butanoic acid, 2-amino-5-(1-pyrryl)pentanoic acid, 2-amino-3-(5-imidazolyl) -3-methylpropanoic acid, 2-amino-3-(5-imidazolyl) -3-ethylpropanoic acid, 2-amino-3-hexyl-3-(5-imidazolyl)propanoic acid, 2-amino-3-hydroxy-3-(5-imidazolyl)propanoic acid, 2-amino-3-(4-nitro-5-imidazolyl)proloanoic acid, 2-amino-3-(4-methyl-5-imidazolyl)propanoic acid, 2-amino-3-(2-methyl-5-imidazolyl)propanoic acid, 2-amino-3-(4-fluoro-5-imidazolyl)propanoic acid, 2-amino-3-(2-fluoro-5-imidazolyl)propanoic acid, 2-amino-3-(2-amino-5-imidazolyl)propanoic acid, 2-amino-3-(2-phenylaza-5-imidazolyl)propanoic acid, 2-amino-3-(1-methyl-2-nitro-5-imidazolyl)propanoic acid, 2-amino-3-(1-methyl4-nitro-5-imidazolyl)propanoic acid, 2-amino-3-(1-methyl-5-nitro-5-imidazolyl)propanoic acid, 2-amino-3-(2-mercapto-5-imidazolyl)propanoic acid, 2-amino-4-(5-imidazolyl) butanoic acid, 2-amino-3-(1-imidazolyl)propanoic acid, 2-amino-3-(2-imidazolyl)propanoic acid, 2-amino-(1-pyrazolyl)propanoic acid, 2-amino-(3-pyrazolyl)propanoic acid, 2-amino-(3,5-dialkyl-4-pyrazolyl)propanoic acid, 2-amino-3-(3-amino-1,2,4-triazol-1-yl)propanoic acid, 2-amino-3-(tetrazol-5-yl)propanoic acid, 2-amino-4-(5-tetrazolyl)butanoic acid, 2-amino-3-(6-methyl-3-indolyl) propanoic acid, 2-amino-3-(4-fluoro-3-indolyl)propanoic acid, 2-amino-3-(5-fluoro-3-indolyl)propanoic acid, 2-amino-3-(6-fluoro-3-indolyl)propanoic acid, 2-amino-3-(4,5,6,7-tetrafluoro-3-indolyl)propanoic acid, 2-amino-3-(5-chloro-3-indolyl)propanoic acid, 2-amino-3-(6-chloro-3-indolyl)propanoic acid, 2-amino-3-(7-chloro-3-indolyl) propanoic acid, 2-amino-3-(5-bromo-3-indolyl)propanoic acid, 2-amino-3-(7-bromo-3-indolyl)propanoic acid, 2-amino-3-(2-hydroxy-3-indolyl)propanoic acid, 2-amino-3-(5-hydroxy-3-indolyl)propanoic acid, 2-amino-3-(7-hydroxy-3-indolyl)propanoic acid, 2-amino-3-(2-alkylmercapto-3 -indolyl)propanoic acid, 2-amino-3-(7-amino-3-indolyl)propanoic acid, 2-amino-3-(4-nitro-3-indolyl)propanoic acid, 2-amino-3-(7-nitro-3-indolyl) propanoic acid, 2-amino-3-(4-carboxy-3-indolyl)propanoic acid, 2-amino-3-(3-indolyl)butanoic acid, 2-amino-3-(2,3-dihydro-3-indolyl)propanoic acid, 2-amino-3-(2,3-dihydro-2-oxo-3-indolyl)propanoic acid, 2-amino-3-alkylmercapto-3-(3-indolyl)propanoic acid, 2-amino-3-(4-aza-3-indolyl) propanoic acid, 2-amino-3-(7-aza-3-indolyl)propanoic acid, 2-amino-3-(7-aza-6-chloro-4-methyl-3-indolyl)propanoic acid, 2-amino-3-(2,3-dihydrobenzofuran-3-yl)propanoic acid, 2-amino-3-(3-methyl-5-7-dialkylbenzofuran-2-yl) propanoic acid, 2-amino-3-(benzothiophen-3-yl)propanoic acid, 2-amino-3-(5-hydroxybenzothiophen-3-yl)propanoic acid, 2-amino-3-eoenzoselenol-3yl)propanoic acid, 2-amino-3-quinolylpropanoic acid, 2-amino-3-(8-hydroxy-5-quinolyl)propanoic acid, 2-amino-2-(5,6,7,8-tetrahydroquinol-5-yl)acetic acid, 2-amino-3-(3-coumarinyl)propanoic acid, 2-amino-2-(benzisoxazol-3-yl) acetic acid, 2-amino-2-(5-methylbenzisoxazol-3-yl)acetic acid, 2-amino-2-(6-methylbenzisoxazol-3-yl)acetic acid, 2-amino-2-(7-methylbenzisoxazol-3-yl)acetic acid, 2-amino-2-(5-bromobenzisoxazol-3-yl)acetic acid, 2-amino-3-(benzimidazol-2-yl)propanoic acid, 2-amino-3-(5,6-dichlorobenzimidazol-2-yl)propanoic acid, 2-amino-3-(5,6-dimethylbenzimidazol-2-yl)propanoic acid, 2-amino-3-(4,5,6,7-hydrobenzirnidazol-2-yl)propanoic acid, 2-amino-2-(benzimidazol-5-yl)acetic acid, 2-amino-2-(1,3-dihydro-2,2-dioxoisobenzothiophen-5-yl)acetic acid, 2-amino-2-(1,3-dihydro-2,2-dioxo-2,1,3-benzothiadiazol-5-yl)acetic acid, 2-amino-2-(2-oxobenzimidazol-5-yl)acetic acid, 2-amino-3-(4-hydroxybenzothiazol-6-yl)propanoic acid, 2-amino-3-(benzoxazol-2-yl)propanoic acid, 2-amino-3-(benzothiazol-2-yl)propanoic acid, 2-amino-3-(9-adeninyl)propanoic acid, 2-amino-2-(6-chloro-9-purinyl)acetic acid, 2-amino-2-(6-amino-9-purinyl)acetic acid, 2-amino-3-(6-purinyl) propanoic acid, 2-amino-3-(8-theobrominyl)propanoic acid, 2-amino-2-(1-uracilyl)acetic acid, 2-amino-2-(1-cytosinyl) acetic acid, 2-amino-3-(1-uracilyl)propanoic acid, 2-amino-3-(1-cytosinyl)propanoic acid, 2-amino-4-(1-pyrimidinyl) butanoic acid, 2-amino-4-(4-amino-1-pyrimidinyl)butanoic acid, 2-amino-4-(4-hydroxy-1-pyrimidinyl)butanoic acid, 2-amino-5-pyrimidinyl)pentanoic acid, 2-amino-5-(4-hydroxy-1-pyrimidinyl)pentanoic acid, 2-amino-3-(5-pyrimidinyl)propanoic acid, 2-amino-3-(6-uracilyl) propanoic acid, 2-amino-3-(2-pyrimidinyl)propanoic acid, 2-amino-3-(6-amino-4-chloro-2-pyrimidinyl)propanoic acid, 2-amino-3-(4-hydroxy-2-pyrimidinyl)propanoic acid, 2-amino-3-(2-amino-4-pyrimidinyl)propanoic acid, 2-amino-3-(4,5-dihydroxypyrimidin-2-yl)propanoic acid, 2-amino-3-(2-thiouracil-6-yl)propanoic acid, 2-amino-2-(5-alkyl-2-tetrahydrofuryl)acetic acid, 2-amino-2-(5-methyl-2,5-dihydro-2-furyl)acetic acid, 2-amino-2-(5-alkyl-2-furyl) acetic acid, 2-amino-2-(2-furyl)acetic acid, 2-amino-2-(3-hydroxy-5-methyl-4-isoxazolyl)acetic acid, 2-amino-3-(4-bromo-3-hydroxy-5-isoxazolyl)propanoic acid, 2-amino-3-(4-methyl-3-hydroxy-5-isoxazolyl)propanoic acid, 2-amino-3-(3-hydroxy-5-isoxazolyl)propanoic acid, 2-amino-2-(3-chloro-D2-isoxazolin-5-yl)acetic acid, 2-amino-3-(3-oxo-5-isoxazolidinyl)acetic acid, 2-amino-3-(3,5-dioxo-1,2,4-oxadiazolin-2-yl)propanoic acid, 2-amino-3-(3-phenyl-5-isoxazolyl)propanoic acid, 2-amino-3-[3-(4-hydroxyphenyl)-1,2,4-oxadiazol-5-yl]propanoic acid, 2-amino-3-(2-thienyl)propanoic acid, 2-amino-2-(2-furyl) acetic acid, 2-amino-2-(2-thienyl)acetic acid, 2-amino-2-(2-thiazolyl)acetic acid, 2-amino-3-(2-thiazolyl)propanoic acid, 2-amino-4-(4-carboxy-2-thiazolyl)butanoic acid, 2-amino-3-(4-thiazolyl)propanoic acid, 2-amino-3-(2-selenolyl)propanoic acid, 2-amino-3-(2-amino-4-selenolyl) propanoic acid, and 2-amino-3-(beta-ribofuranosyl) propanoic acid.

"Amino acids residue" also refers to various amino acids where sidechain functional groups are coupled with appropriate protecting groups known to those skilled in the art. "The Peptides", Vol 3, 3–88 (1981) discloses numerous suitable protecting groups and is incorporated herein by reference for that purpose. Examples of amino acids where sidechain functional groups are coupled with appropriate protecting groups include, but are not limited to, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), and Thr (OBzl).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit HCV infection or treat the symptoms of HCV infection in a host. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The compounds of this invention are intended to interact with the catalytic serine hydroxyl of Hepatitis C NS3 protease, and therefore incorporate an electrophilic moiety capable of such interaction. In the synthetic schemes below, this moiety, or its synthetic equivalent or precursor, is referred to as a "serine trap" and is defined by structure 1-10.

Synthesis of inhibitors 1-11, 1-12, and 1-13

Scheme 1 illustrates the synthesis of inhibitors of structure 1-11, 1-12 and 1-13. In Scheme 1, $R^3$, $A^3$, $R^8$, $R^1$, and W are as defined above; $R^{1"}$, is H or small alkyl group, for example methyl or ethyl, P is a nitrogen protecting group, and R is a standard leaving group for carboxylic acids, wherein such protecting and leaving groups are known to one skilled in the art.

a) Protected cyclic amine (n=1–3) is oxidized with ruthenium oxide in a two-phase system (Yoshifuji, S. et al, *Chem. Pharma. Bull.* 1986, 34, 3873–3878) to the corresponding lactam 1-1 (n=1–3), then treated with strong base and alkylated with electrophile. It can be monoalkylated or dialkylated with $R^3$-X" and $R^{13}$-X" to give 4-substituted pyroglutamate 1-2. Pyroglutamate 1-2 is reduced by diisobutylaluminum hydride (DIBAL) or lithium triethylborohydride (super hydride) to the corresponding aminal 1-3, which is exchanged with methanol under acidic condition through acyl-iminium ion chemistry to 5-methoxyl-1-tert-butoxycarbonylpyroglutamate 1-4. Synthesis of compound 1-4 may also be accomplished using the chemistry outlined in Scheme 2. Briefly, N-protected glutamic acid derivative 2-4a is converted to thioester 2-4b catalyzed by EDC/DMAP. The thioester 2-4b is reduced to aldehyde by triethylsilane (Fukuyama, T. et al. *J. Am. Chem. Soc.* 1990, 112, 7050–7051), which reacts in an intramolecular fashion to give compound 1-4 in methanol.

b) 5-Methoxy pyroglutamate 1-4 is reacted with trimethylsilyl cyanide catalyzed by a Lewis acid such as $ZnCl_2$ or $BF_3$ etherate in methylene chloride to give 5-cyano pyroglutamate 1-5. The protecting group is removed to generate aminonitrile salt 1-6. The salt is reacted with oxalyl chloride or bromide at elevated temperature to produce dihydropyrrolopyrazinone 1-7 wherein R6 is Cl or Br.

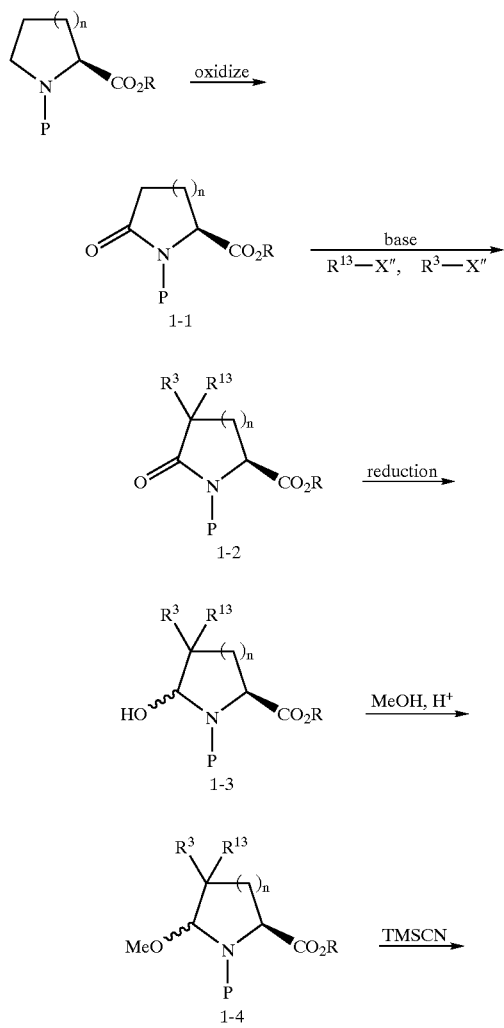

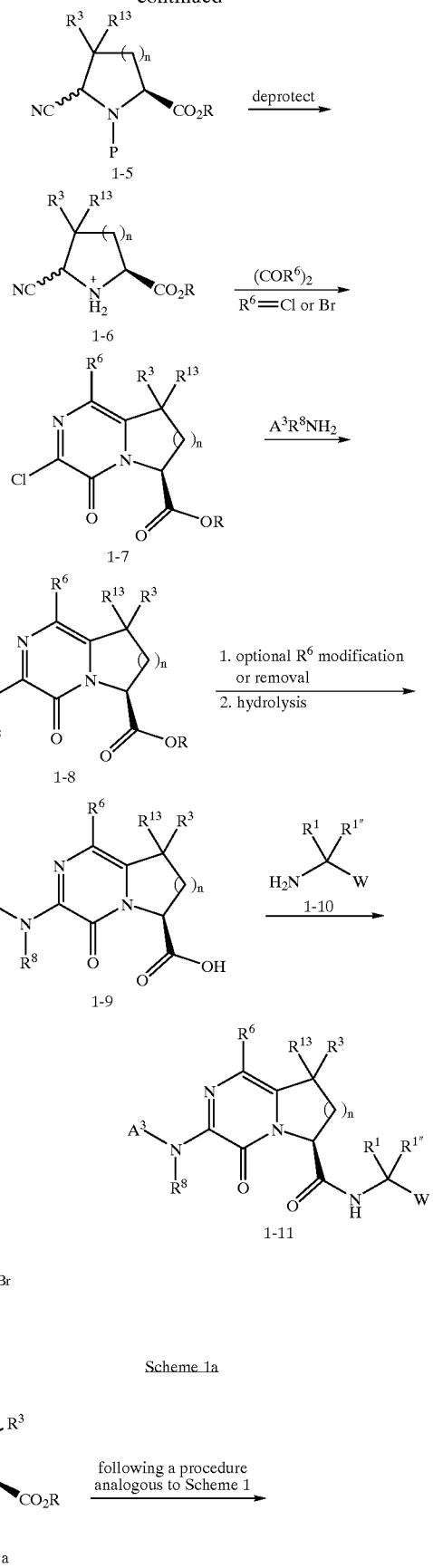

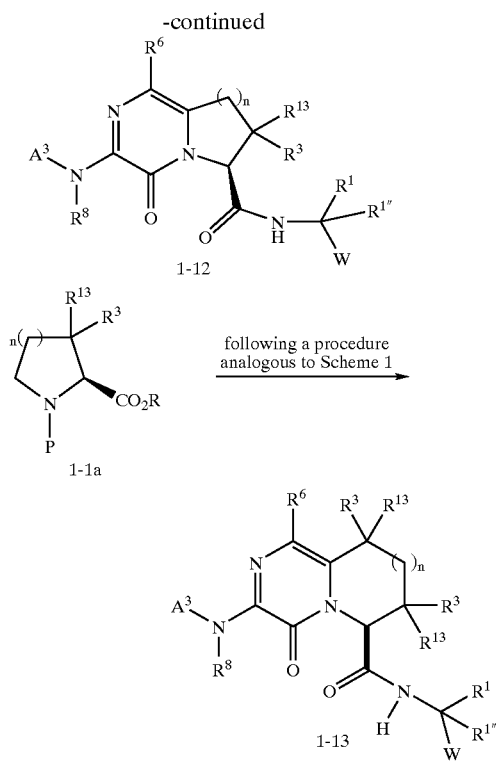

Scheme 2

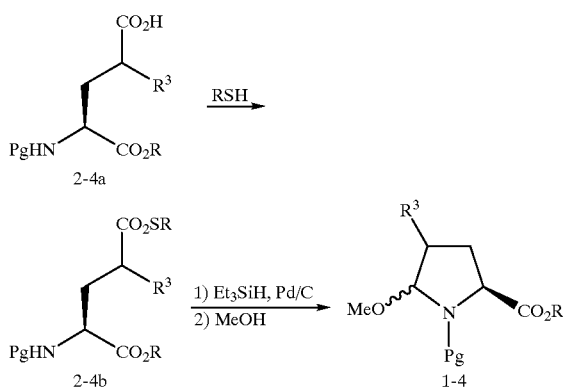

c) Dihydropyrrolopyrazinone 1-7 reacts with amine $A^3R^8NH_2$ regiospecifically to give 3-amino-dihydropyrrolopyrazinone 1-8 in ethyl acetate or dioxane. When $A^3=R^8=H$, the amino group can be coupled to a suitably protected peptide fragment by methods known to one skilled in the art. The remaining chlorine or bromine is then optionally removed by hydrogenolysis or can be coupled to organometalic reagents using the chemistry known as Heck and Suzuki coupling (Suzuki et al. Chem. Rev. 1995, 95, 2457–2483). Hydrolysis of the ester 1-8 to the free acid, and peptide coupling with a serine trap $H_2NC(R^1R^{1"})W$ (1-10) affords the inhibitor 1-11. Similarly, an inhibitor of formula 1-12 or 1-13 can be made from precursor 1-1a following the analogous chemistry describe above. 1-1a is made according to the chemistry described by Sardina et al (Blanco, M. et al, *J. Org. Chem.* 1999, 64, 8786–8793).

Compound 1-11, 1-12 or 1-13 are further purified by techniques known to those skilled in the art. These include silica gel chromatography, reverse phase HPLC, and size exclusion chromatography using Sephedex™ LH-20.

Synthesis of a serine trap of structure 1-10 a) Synthesis of •-amino boronic ester

Scheme 3 outlines a route to mono-substituted amino boronic esters. In Scheme 3, a Grignard reagent is reacted with a borate ester 3-12a, which can be prepared by the reaction of pinanediol with trialkylborate, providing boronate 3-12b. Homologation of 3-12b with the anion of dichloromethane gives the •-chloro boronic ester 3-12c. (Matteson, D. S.; Majumdar, D. *Organometallics* 1983, 2, 1529–1535). Displacement of the chloride by lithium bis (trimethylsilyl)amide gives silyl amine 3-12d, which is converted to the amine hydrochloride salt 3-12e with anhydrous HCl. (Matteson, D. S. Sadhu, K. M. *Organometallics* 1984, 3, 1284–1288). Notice that 3-12e is shown protected as the pinanediol ester. This is the preferred protecting group, but other diol protecting groups, for example but not to be limiting the scope of workable and known diol protecting groups, pinacol, 1,2-ethanediol, 1,2-propanediol, 1,3-propanediol, 2,3-butanediol, 1,2-diisopropylethanediol, 5,6-decanediol, 1,2-dicyclohexylethanediol, are known to those skilled in the art.

Peptide boronic esters can be prepared from commercially available materials by methods known to one skilled in the art of organic synthesis. Peptide boronic acids and esters are generally well known in the art; however, for a general reference to synthesis of peptide boronic esters, see: Kettner, C; Forsyth, T. *Houben-Weyl Methods of Organic Chemistry* 1999, in press; for a reference to synthesis of fluorinated peptide residues see Matassa, V. et al., PCT Application WO 9964442, published Dec. 12, 1999. More preferably, see techniques disclosed in copending commonly assigned U.S. Provisional Patent Application 60/142,561, filed Jul. 7, 1999; herein incorporated in its entirety by reference; as well as copending commonly assigned U.S. Provisional Patent Application Ser. No. 60/145,631, filed Jul. 26, 1999; herein incorporated in its entirety by reference.

Scheme 3

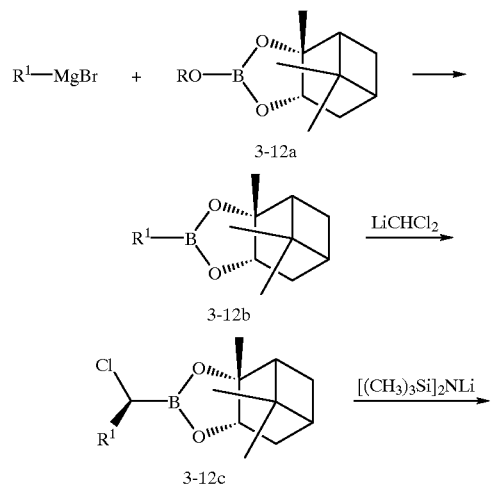

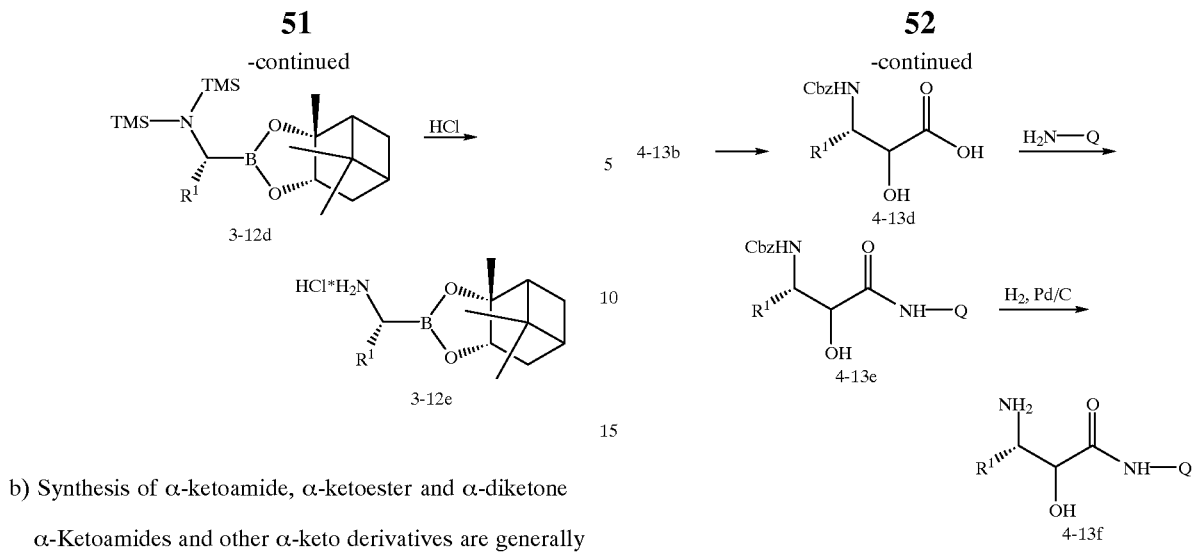

b) Synthesis of α-ketoamide, α-ketoester and α-diketone

α-Ketoamides and other α-keto derivatives are generally introduced in the hydroxy form and oxidized to the active ketone form in the final synthetic step after it is coupled to the pyrazinone carboxylic acid 1-9. Scheme 4 illustrates the synthesis of α-hydroxy esters and α-hydroxy amides. In Scheme 4, substituted acrylate ester 4-13a is aminohydroxylated using a Sharpless's procedure (Tao, B., Sharpless, K. B. et al. *Tetrahedron Lett.* 1998, 39, 2507–2510) to Cbz-protected amino alchol 4-13b. Catalytic hydrogenation of 4-13b gives a-hydroxy ketoester 4-13c. Alternatively, 4-13b is hydrolyzed to free acid 4-13d and coupled to amine $H_2N-Q$ to give Cbz-protected amino α-hydroxy amide 4–13e. Catalytic hydrogenation of 4–13e gives α-hydroxy ketoamide 4–13f. For other methods to prepare α-keto esters, amides or other electrophilic carbonyl derivatives, see: N. P. et al. *Tetrahedron Lett*. Peet, 1988, 3433–3436; Edwards, P. D.; Bernstein, P. R. *Medicinal Res. Reviews* 1994, 14, 127–194, and references cited therein; Sharpless, K. B.; et al, *Angew. Chem.* Int. Ed. Engl. 1996, 35, 451; and Sharpless, K. B. et al, *Angew. Chem.* Int. Ed. Engl. 1996, 35, 2813. Many of the α, β-unsaturated esters, 4–13a, are commercially available or may be easily prepared from commercially available materials.

Amines of formula $H_2N-Q$ can be prepared from commercially available materials by methods known to one skilled in the art of organic synthesis. More preferably, see techniques disclosed in copending commonly assigned U.S. Provisional Patent Application Ser. No. 60/168,998, filed Dec. 3, 1999; herein incorporated in its entirety by reference.

Scheme 4

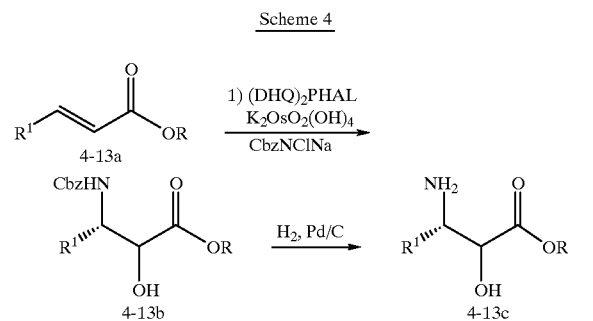

c) Synthesis of amino trifluoromethyl and pentafluoroethyl ketones.

Similar toa-ketoamides and other a-keto derivatives, the trifluoromethyl or pentafluoroethyl ketone functionality is also introduced in the hydroxy form and oxidized to the active ketone form in the final step. Scheme 5 illustrates the synthesis of amino trifluoromethyl alcohol (Skiles, J. W. et al. *J. Med. Chem.* 1992, 35, 641–662) and amino pentafluoroethyl alcohol (Ogilvie, W. et al. *J. Med. Chem.* 1997, 40, 4113–4135). In Scheme 5, a Henry reaction between a nitroalkane $R^1NO_2$ and trifluoroacetaldehyde ethyl hemiacetal affords nitro alcohol 5–14a, which is hydrogenated over Ra-Ni and the resulting amino alcohol 5–14b is converted to the N-Boc derivative 5–14c. Treatment of the Boc-amine with anhydrous HCl affords the hydrochloride salt 5–14d. A solid-phase synthesis of peptidyl trifluoromethyl ketones is also known, see: Poupart, M.-A., et al. *J. Org. Chem.* 1999, 64, 1356–1361. Alternatively, condensation of the Weinreb amide 5–15a with $CF_3CF_2Li$ followed by reduction with $NaBH_4$ gives pentafluoroethyl substituted alcohol 5–15b. Deprotection of 5–15b gives the amino alcohol salt 5–15d.

Scheme 5

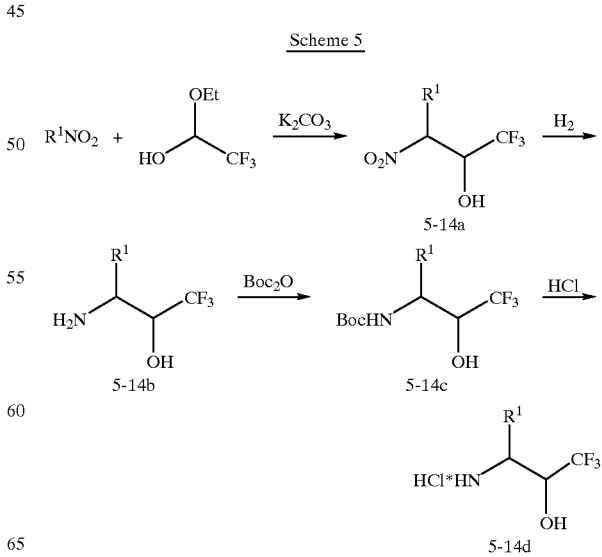

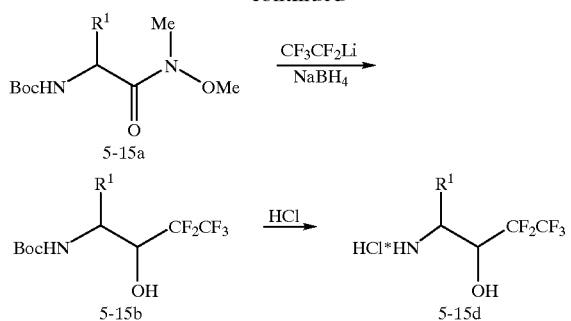

d) Synthesis of difluoro β-ketoamide

Scheme 6 outlines the synthesis of hydroxy difluoro β-ketoamides (see: Veale, C. A. et al. *J. Med. Chem.* 1997, 40, 3173–3181; Wolfe, M. S. et al. *J. Med. Chem.* 1998, 41, 6–9). In Scheme 6, protected aminoaldehyde 6–16a (For preparation of α-aminoaldehyde, see: Fukuyama, T. et al. *J. Am. Chem. Soc.* 1990, 112, 7050–7051 and Scheidt, K. A. et al. *Bioorg. Med. Chem.* 1998, 6, 2477–2499) is reacted with 2-bromo-2,2-difluoroacetate to produce difluoro alcohol 6–16b. The alcohol 6–16b is hydrolyzed to the acid and coupled to an amine $H_2N-Q$ to give 6–16c. The nitrogen protecting group Pg is removed according to procedures known to one skilled in the art (see Greene, T. W. in *Protective Groups in Organic Synthesis*, John Wiley & Sons, $2^{nd}$ Ed, 1991), producing difluoro β-ketoamide 6–16d.

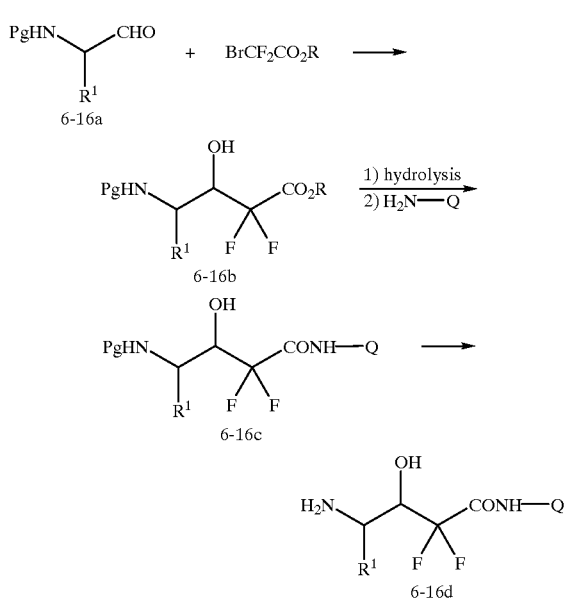

The serine traps described above are generally coupled to the free acid of the dihydropyrrolopyrazinone using known peptide coupling procedures, preferably by the phosphonium salt PyAOP (Carpino, et al. *J. Chem. Soc., Chem. Commun.* 1994, 201–203). The alcohol functionality of the hydroxy serine trap is oxidized by procedures known to those skilled in the art, such as Dess-Martin periodinane method (Dess, D. B, Martin, J. C. *J. Org. Chem.* 1983, 48, 4155–4156) in the final step to give a compound of structure 1-11 and 1-12 wherein W contains an activated carbonyl.

When required, separation of the racemic material can be achieved by HPLC using a chiral column or by a resolution using a resolving agent such as camphonic chloride (Steven D. Young, et al, *Antimicrobial Agents and Chemotheraphy* 1995, 2602–2605). A chiral compound may also be directly synthesized using a chiral catalyst or a chiral ligand (Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Solution ratio express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Abbreviations used in the Examples are defined as follows: "° C" for degrees Celsius, "MS" for mass spectrometry, "CIMS" for chemical ionization mass spectroscopy, "ESMS" for electrospray ionization mass spectroscopy, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and "α", "β", "R", and "S" are stereochemical designations familiar to one skilled in the art.

As used throughout the specification, the following abbreviations for chemical reagents apply:

Boc is tertbutyl oxycarbonyl,

Cbz is carbonylbenzyloxy, $(DHQ)_2PHAL$ is hydroquinine 1,4-phthalazinediyl diether, DIBAL is diisobutylaluminum hydride, DIEA is diethylpropyl amine, DMAP is dimethylaminopyridine, DMF is dimethylformamide, EDC is 1-(3-dimethylaminopropyl)-3-ethylcarbodiimide hydrochloride, PTSA is para-toluene sulphonic acid, PyAOP is 7-azabenzotriazol-1-yloxytris(pyrrolidino)-phosphonium-hexafluorophosphate, TFA is trifluoroacetic acid, TMSCN is trimethylsilyl cyanide, p-TsOH is p-toluenesulphonic acid.

Example 1

(6S,8R)- N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[4-methoxyphenyl]methyl]amino]-pyrrolo[1,2-a[pyrazine-6-carboxamide.

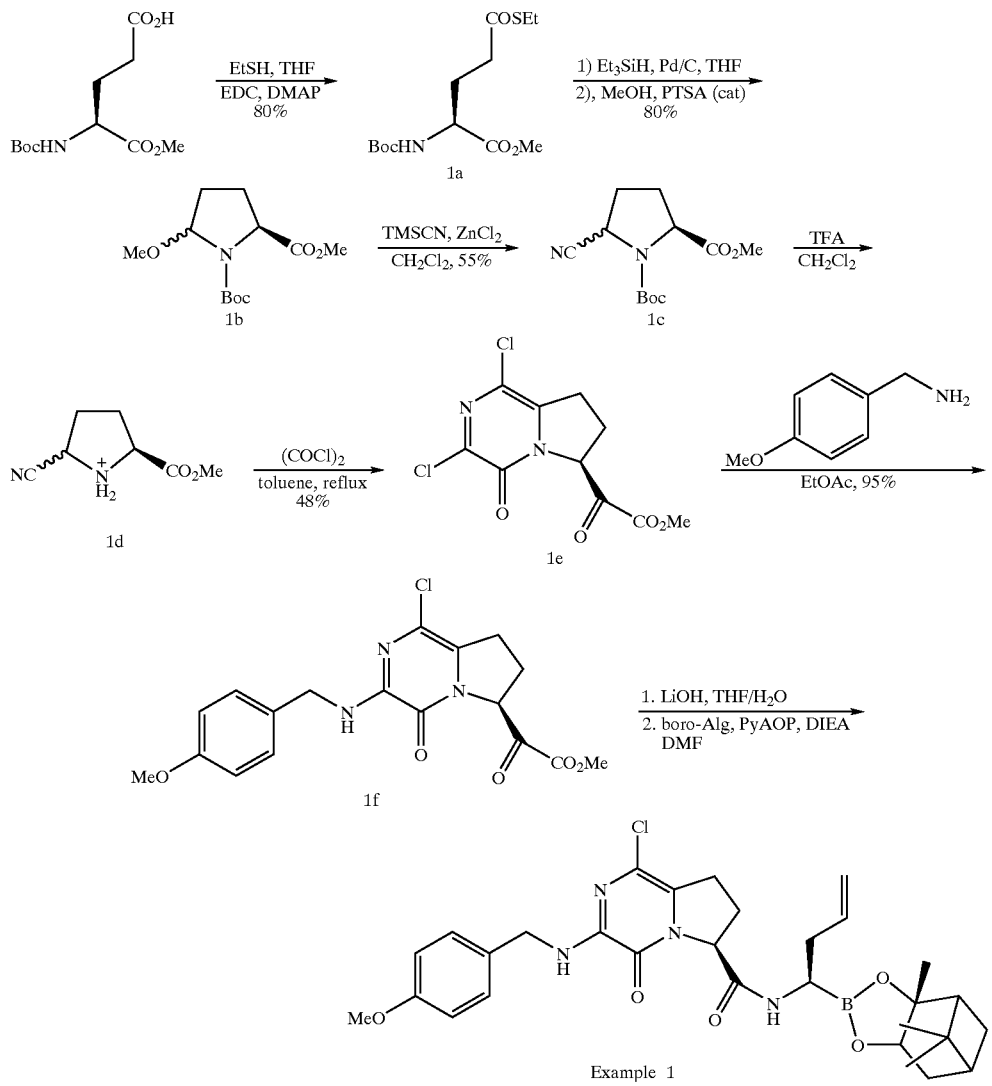

Example 1

Step 1. Synthesis of thioester intermediate 1a:

To a mixture of Boc-Glu-OMe (12.5 g, 47.8 mmol) and ethyl mercaptan (9.30 mL, 143 mmol) in THF (200 mL) was added EDC (9.17 g, 47.8 mmol) and DMAP (0.47 g, 3.82 mmol). The solution was stirred overnight at rt before THF was removed under reduced pressure. The residue was extracted with ethyl acetate. The combined organic phases were washed with 1.0 N HCl, 5% NaHCO$_3$, brine, dried over MgSO$_4$. Filtration and evaporation of solvent gave practically pure product 1a (11.1 g) as a colorless viscous oil. $^1$H NMR (300 MHz, CDCl$_3$) δ5.04 (b, 1 H), 4.38 (m, 1 H), 4.14 (q, J=7.3 Hz, 2 H), 2.90 (q, J=7.3 Hz, 2H), 2.64 (m, 2 H), 2.20 (m, 1 H), 1.98 (m, 1 H), 1.44 (s, 9 H), 1.24 (t, 3 H).

Step 2. Synthesis of pyrrolidine intermediate 1b:

To a solution of thioester 1a (9.5 g, 31.1 mmol) and Pd/C (10%, 2.4 g) in THF (30 mL) at 0° C. was added triethyl silane (9.94 mL, 62 mmol) slowly. The mixture was stirred from 0° C. to rt for 2.0 h before methanol (100 mL), PTSA (0.296 g, 1.55 mmol) was added. The mixture was stirred at rt for 1.0 h, filtered through a pad of celite. Removal of solvent and flash column chromatography (hexane/ethyl acetate, 2:1) gave product 1b (6.5 g) as a colorless viscous oil. $^1$H NMR (300 MHz, CDCl$_3$) indicated a mixture of two isomers and complicated by the presence of two rotomers. CIMS m/e 228 (M–OMe).

Step 3. Synthesis of pyrrolidine intermediate 1c:

To a solution of methoxyl-1-tert-butoxycarbonyl-pyroglutamate (4.10 g, 15.81 mmol) in CH$_2$Cl$_2$ (40 mL) at −30° C. was added trimethylsilyl cyanide (6.3 mL, 47.4 mmol) and ZnCl$_2$ (1.0 M in Et2O, 5.53 mL, 5.53 mmol). The mixture was stirred from −30° C. to rt overnight before it was quenched with sat. NaHCO$_3$. Organic layer was separated and the aqueous was extracted with CH$_2$Cl$_2$. The combined organic layers were washed with brine, dried over MgSO4. Filtration, evaporation of solvent and flash column chromatography (hexane/ethyl acetate, 3:1) gave a separated cis and tran isomers of product 1c (2.20 g). $^1$H NMR (300 MHz, CDCl$_3$) δ isomer 1: 4.68 (dd, J=4.0, 2.0 Hz) and 4.55 (t, J=5.4 Hz) for 1 H, 4.40 (t, J=7.7 Hz) and 4.26 (t, J=6.9 Hz) for 1 H, 3.79 (s, 3 H), 2.42–1.98 (m, 4 H), 1.52 (s) and 1.44 (s) for 9 H; isomer 2: 4.78 (dd, J=8.8, 1.5 Hz) and 4.67 (d, J=8.0 Hz) for 1 H, 4.45 (d, J=8.8 Hz) and 4.34 (d, J=8.0 Hz) for 1 H, 3.75 (s) and 3.73 (s) for 3 H, 2.56–2.12 (m, 4 H), 1.52 (s) and 1.43 (s) for 9 H; CIMS 255 (M+H).

Step 4. Synthesis of pyrrolopyrazinone intermediate 1e:

To a solution of pyrrolidine intermediate 1c (2.20 g) in $CH_2Cl_2$ (10 mL) was added trifluoroacetic acid (11.0 mL). The mixture was stirred at rt for 1.0 h before the solvent was removed under reduced pressure. The residue, containing 1d, was further chased with toluene to remove residue trifluoroacetic acid. The TFA salt obtained was suspended in toluene (15 mL) and oxalyl chloride (3.02 mL, 34.0 mmol). The mixture was heated at 85° C. overnight in a pressure vessel. Toluene and oxaly chloride was removed under reduced pressure. The residue was purified by a flash column chromatography (hexane/ethyl acetate, 1:1) to give 1.10 g of the product, 1e, as a viscous, brownish oil. $^1$H NMR (300 MHz, $CDCl_3$) δ5.17 (dd, J=9.5, 2.9 Hz, 1 H), 3.83 (s, 3 H), 3.20 (m, 2 H), 2.62 (m, 1 H), 2.41 (m, 1 H).

Step 5. Synthesis of pyrrolopyrazinone intermediate 1f:

A mixture of pyrrolopyrazinone intermediate 1e (27 mg, 0.1 mmol) and p-methoxybenzyl amine (0.067 mL, 0.5 mmol) in ethyl acetate (0.5 mL) was heated at 75°°C. for 3.0 h. The mixture was directly loaded on a column and eluted with hexane/ethyl acetate (1:1) to give 21 mg of the product, 1f, as a white solid. $^1$H NMR (300 MHz, $CDCl_3$) δ7.29 (d, J=8.8 Hz, 2 H), 6.88 (d, J=8.8 Hz, 2 H), 6.34 (br, t, J=5.5 Hz, 1 H), 5.07 (dd, J=9.5, 3,3 Hz, 1 H), 4.51 (d, J=5.5 Hz, 2 H), 3.80 (s, 3 H), 3.05 (m, 2 H), 2.51 (m, 1 H), 2.34 (m, 1 H). ESMS m/e cald for $C_{17}H_{19}N_3O_4$ 364.1037, obsd 364.1064.

Step 6. Final step in the synthesis of Example 1:

To a solution of the pyrrolopyrazinone intermediate 1f (21 mg, 0.061mmol) in THF (0.4 mL) at 0°°C. was added LiOH (1.0 M in $H_2O$, 0.15 mL, 0.15 mmol). The mixture was stirred at 0° C. for 3 h before 5% citric acid was added till pH 5-6. The mixture was extracted with ethyl acetate. The organic layer was washed with brine, dried over $MgSO_4$. Filtration, evaporation of solvent gave the free acid, which was used directly for the next step.

To a mixture of the free acid (20 mg, 0.061 mmol), Alg-boro-$C_{10}H_{16}O_2$ (17.4 mg, 0.061 mmol), PyAOP (39.8 mmol, 0.076 mmol) in DMF (0.6 mL) was added DIEA (0.043 mL, 0.24 mmol). The mixture was stirred at rt for 1 h. It was diluted with ethyl acetate and 5% $NaHCO_3$. The organic layer was separated and condensed. The residue was purified by HPLC(C18) to give the product, Example 1 (5.0 mg) as a white solid.7.26 (d, J=8.6 Hz, 2 H), 6.89 (d, J=8.6 Hz, 2 H), 6.21 (br, t, J=5.4 Hz, 1 H), 5.71 (m, 1 H), 5.01 (d, J=8.0 Hz, 1 H), 4.95 (m, 2 H), 4.51 (d, J=5.4 Hz, 2 H), 4.52 (m, 1 H), 3.18 (m, 2 H), 2.95 (m, 1 H), 2.8–1.79 (m, 9 H), 1.42–1.20 (m), 0.94 (s, 3 H0, 0.84 (s, 3 H); ESMS m/e calcd for $C_{30}H_{39}BClN_4O_5$ 581.2719, obsd 581.2717.

Example 2

(6S,8R) —N—[[(1R)—1—[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)phenyl]methyl]amino]-pyrrolo[1,2-a]pyrazine-6-carboxamide.

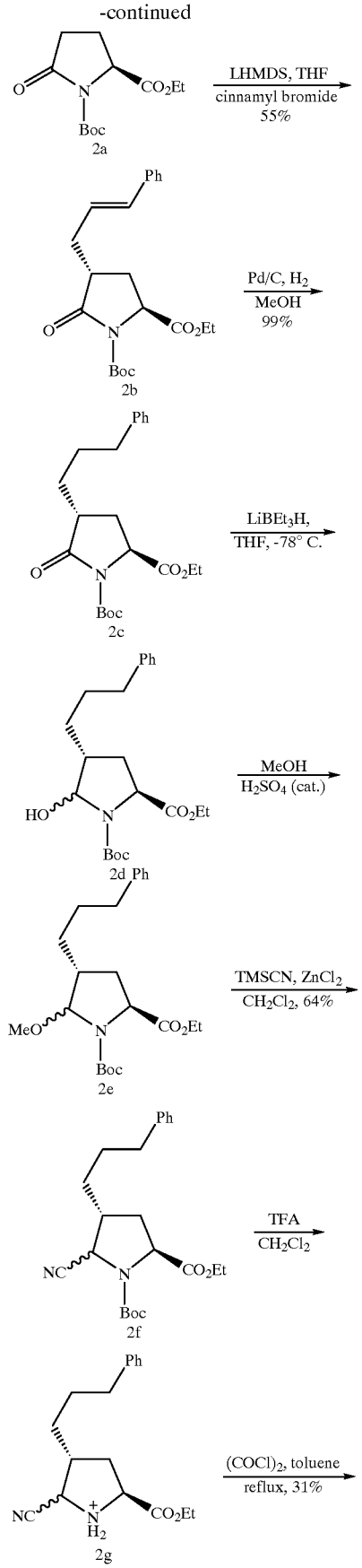

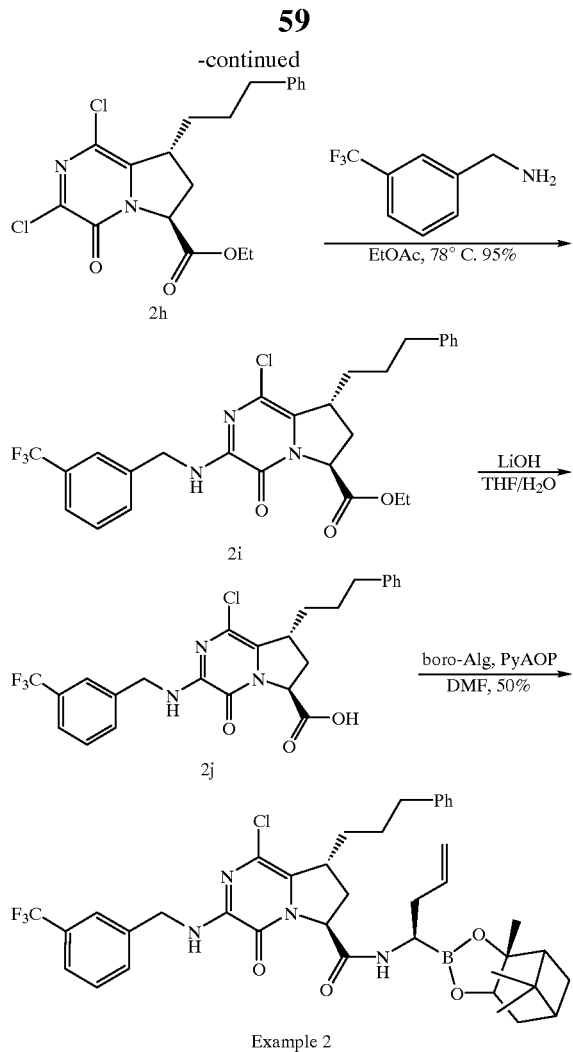

Example 2

Step 1. Synthesis of pyrrolidine intermediate 2a:

To a solution of the (S)-ethyl pyroglutamate (2.0 g, 12.7 mmol) in THF (40 mL) at −78° C. was added lithium bis(trimethylsily)amide (1.0 M in THF, 13.3 mL, 13.3 mmol). The mixture was stirred for 30 min. at −78° C., followed by addition of di-tert-butyl dicarbonate (3.60 g, 16.5 mmol) in THF (10 mL). The reaction was stirred at −78° C. for 20 min. before it was quenched with 5% citric acid. THF was removed and the residue was extracted with ethyl acetate. The organic phase was washed with sat. NaHCO$_3$, brine and dried over MgSO$_4$. Filtration, evaporation of the solvent and flash column chromatography (hexanes/ethyl acetate, 1:1) gave 3.40 g of the product, 2a, as a solid. $^1$H NMR (300 MHz, CDCl$_3$) δ4.59 (dd, J=9.2, 2.6 Hz, 1 H), 4.23 (q, J=7.30 Hz, 2 H), 2.67–2.30 (m, 3 H), 2.06 (m, 1 H), 1.50 (s, 9 H), 1.28 (t, J=7.30 Hz, 3 H).

Step 2. Synthesis of pyrrolidine intermediate 2b:

To a solution of pyrrolidine intermediate 2a (8.80 g, 34.2 mmol) in THF (200 mL) at −78° C. was slowly added lithium bis(trimethylsily)amide (1.0 M in THF, 41 mL, 41.0 mmol). After the mixture was stirred for 1.0 h at −78° C., cinnamyl bromide (7.6 mL, 51 mmol) was added, and stirring was continued at −78° C. for 2.0 h. The reaction was quenched at −78° C. with 5% citric acid, extracted with ethyl acetate. The combined organic phases were washed with 5% NaHCO$_3$, brine, and dried over MgSO$_4$. Evaporation of the solvent and flash column chromatography (hexanes/EtOAc, 5:1) gave intermidate 2b(6.0 g) as viscous oil. $^1$H NMR (300 MHz, CDCl$_3$) δ7.35–7.20 (m, 5 H), 6.46 (d, J=16.0 Hz, 1 H), 6.15 (dt, J=16.0, 7.3 Hz, 1 H), 4.50 (d, J=9.5 Hz, 1 H), 4.20 (q, J=7.3 Hz, 2 H), 2.80 (m, 2 H), 2.40 (m, 1 H), 2.20–2.00 (m, 2 H), 1.50 (s, 9 H), 1.27 (t, J=7.3 Hz, 3 H). ESMS m/e 512 (M+Na).

Step 3. Synthesis of pyrrolidine intermediate 2c:

A solution of pyrrolidine intermediate 2b (6.0 g) and Pd/C (10%, 620 mg) in methanol (150 mL) was hydrogenated at 40 psi in a par-shaker for 3.0 h. Pd/C was removed by filtration through a pad of celite. Removal of solvent under reduced pressure gave practically pure intermediate 2c as a viscous oil. $^1$H NMR (300 MHz, CDCl$_3$) δ7.29–7.14 (m, 5 H), 4.53 (d, J=9.5 Hz, 1 H), 4.22 (q, J=7.0 Hz, 2 H), 2.60 (m, 3 H), 2.20 (m, 1 H), 1.98 (m, 2 H), 1.64 (m, 2H), 1.50 (s, 9 H), 1.28 (t, J=7.0 Hz, 3 H).

Step 4. Synthesis of pyrrolidine intermediate 2d:

To a solution of pyrrolidine intermediate 2c (220 mg, 0.586 mmol) in THF (5.0 mL) at −78° C. was added LiBEt$_3$H (1.0 M in THF, 0.7 mL, 0.7 mmol). The reaction was stirred at −78° C. for 30 min before it was quenched with sat. NaHCO$_3$. The mixture was extracted with ethyl acetate. The combined organic phases were washed with brine and dried over K$_2$CO$_3$. Filtration and evaporation of the solvent gave colorless viscous oil as product 2d. ESMS m/e 400.2 (M+Na). $^1$H NMR indicated the product was a mixture of two diastereomers in a ratio of 2:1. The crude product 2d was sufficiently pure, and it was used directly for the next step without further purification.

Step 5. Synthesis of pyrrolidine intermediate 2e:

To a solution of pyrrolidine intermediate 2d (1.25 g, 3.31 mmol) in methanol (25 mL) was added conc. H$_2$SO$_4$ (0.060 mL). The mixture was stirred at rt for 30 min before it was quenched with sat. NaHCO$_3$. Methanol was removed under reduced pressure. The residue was extracted with ethyl acetate. The combined organic phases were washed with brine and dried over Na$_2$SO$_4$. Evaporation of solvent and flash column chromatography (hexane/ethyl acetate, 6:1) gave 990 mg of the product, 2e, as a viscous oil. $^1$H NMR indicated a partial epimerization at C-4. $^1$H NMR (300 MHz, CDCl$_3$) δ7.30–7.15 (m, 5 H), 5.17–4.99 (m, 1 H), 4.20 (m, 3 H), 3.45, 3.43, 3.39 (s, 3 H), 2.61 (m, 2 H), 2.22–1.60 (m, 9 H), 1.56, 1.48, 1.43, 1.40 (s, 9 H), 1.28 (m, 3 H), ESMS m/e 414.2 (M+Na)

Step 6. Synthesis of pyrrolidine intermediate 2f:

To a solution of pyrrolidine intermediate 2e (237 mg, 0.61 mmol) in CH$_2$Cl$_2$ (3.0 mL) at −30° C. was added trimethylsilyl cyanide (0.234 mL, 1.83 mmol) and ZnCl$_2$ (1.0 M in Et$_2$O, 0.40 mL, 0.4 mmol). The reaction was stirred from −30° C. to rt overnight before it was quenched with sat. NaHCO$_3$. The mixture was extracted with ethyl acetate. The combined organic phases were washed with brine and dried over Na$_2$SO$_4$. Evaporation of solvent and flash column chromatography (hexane/ethyl acetate, 6:1) gave product 2f (150 mg) as a viscous oil. ESMS m/e 450.3 (M+Na+ CH$_3$CN).

Step 7. Synthesis of pyrrolidinium intermediate 2g:

To a solution of pyrrolidine intermediate 2f (170 mg, 0.44 mmol) in CH$_2$Cl$_2$ (0.35 mL) was added TFA (0.35 mL, 4.4 mmol). The mixture was stirred at rt for 1.0 h before solvent and TFA were removed under reduced pressure. The residue was further chased with toluene. Product 2g was directly used for the next step without further purification. ESMS m/e 287.3 (M+H).

Step 8. Synthesis of pyrrolopyrazinone intermediate 2h:

A mixture of pyrrolidinium intermediate 2g (1.36 g, 3.40 mmol) and oxalyl chloride (1.18 mL, 13.6 mmol) in toluene (10 mL) was heated at 86° C. overnight in a sealed reaction vessel. Solvent was removed and the residue was purified by flash chromatography (hexane/ethyl acetate, 3:1) to give 410 mg of the product 2h as a brownish solid. $^1$H NMR (300 MHz, CDCl$_3$) δ7.33–7.15 (m, 5 H), 4.98 (dd, J=8.8, 6.5 Hz, 1 H), 4.22 (m, 2 H), 3.51 (m, 1 H), 2.64 (m, 2 H), 2.40 (m, 2 H), 2.04 (m, 1 H), 1.45 (m, 3 H), 1.30 (t, J=6.9 Hz, 3 H).

Step 9. Synthesis of pyrrolopyrazinone intermediate 2i:

A mixture of pyrrolopyrazinone intermediate 2h (35 mg, 0.09 mmol) and m-(trifluoromethyl)benzyl amine (0.051 mL, 0.36 mmol) in ethyl acetate (0.8 mL) was heated at 75° C. for 5.0 h before it was quenched with 5% citric acid at rt. The mixture was extracted with ethyl acetate. The organic layer was dried over MgSO$_4$. Filtration, evaporation of the solvent and column chromatography gave product 2i (45 mg) as a solid. $^1$H NMR(300 MHz, CD$_3$OD) δ7.62–7.40 (m, 4 H), 7.20 (m, 5 H), 4.96 (t, J=7.6 Hz, 1 H), 4.60 (s, 2 H), 4.20 (q, J=7.40 Hz, 2 H), 3.38 (m, 1 H), 2.62 (m, 2 H), 2.33 (t, J=7.00 Hz, 2 H), 1.98 (m, 1 H), 1.60 (m, 3 H), 1.22 (t, J=7.40 Hz, 3 H), $^{13}$C NMR (75 MHz, CD$_3$OD) δ172.03, 152.03, 151.22, 144.29, 142.68, 133.58, 131.13, 130.45, 129.85, 127.85, 126.59, 125.80, 123.51, 64.11, 63.38, 46.09, 43.24, 37.61, 34.50, 33.61, 30.49, 15.33; $^{19}$F NMR (282.2 MHz, CD$_3$OD) δ62.01 (s).

Step 10. Synthesis of pyrrolopyrazinone intermediate 2j:

To a solution of pyrrolopyrazinone intermediate 2i (45 mg, 0.084 mmol) in methanol (0.6 mL) at 0° C. was added a LiOH solution (1.0 M in H$_2$O, 0.3 mL, 0.3 mmol). The mixture was stirred at 0° C. for 1.0 h and then at rt for 2.0 h before it was acidified with 5% citric acid to pH 5-6. The mixture was extracted with ethyl acetate. The organic layer was washed with brine and dried over MgSO$_4$. Filtration and evaporation of the solvent gave product 2j (39 mg) as a white solid. It was sufficiently pure and used without further purification. $^1$H NMR (300 MHz, CD$_3$OD) δ7.66–7.42 (m, 4 H), 7.19 (m, 6 H), 4.92 (m, 1 H), 4.60 (s, 2 H), 3.38 (m, 1 H), 2.62 (m, 2 H), 2.37 (m, 2 H), 2.03 (m, 1 H), 1.60 (m, 3 H); $^{19}$F NMR (282 MHz, CD$_3$OD) δ−64.5 (s); ESMS m/e 504.2 (M—H)

Step 11. Synthesis of Final Product; Example 2:

To a mixture of the pyrrolopyrazinone intermediate 2j (33 mg, 0.065 mmol), PyAOP (43 mg, 0.082 mmol), Alg-boro-C$_{10}$H$_{16}$O$_2$ (22 mg, 0.070 mmol) in DMF (0.6 mL) was added DIEA (0,045 mL, 0.26 mmol). The mixture was stirred at rt for 1.0 h. It was then diluted with ethyl acetate and 5% NaHCO$_3$. The organic layer was separated and condensed. Preparative HPLC (C$_{18}$) gave final product, Example 2, (20 mg) as a white solid. ESMS m/e cald for C$_{39}$H$_{46}$BClF$_3$N$_4$O$_4$ 737.3234, obsd 737.3236.

Example 3

(6S,8R)-N-[[(1R)-1-[(3aS,4S,6S,7aR)-hexahydro-3a, 5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2,5-difluorophenyl]methyl] amino]-pyrrolo[1,2-a]pyrazine-6-carboxamide.

The title compound was prepared in a procedure similar to that of Example 2. ESMS m/e cald for C$_{38}$H$_{45}$BClF$_2$N$_4$O$_4$ 705.3191, obsd 705.3200.

Example 4

(6S,8R)-N-[[(1R)-1-[(3aS,4S,6S,7aR)-hexahydro-3a, 5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[3-methylphenyl]methyl] amino]-pyrrolo[1,2-a]pyrazine-6-carboxamide.

The title compound was prepared in a procedure similar to that of Example 2. ESMS m/e cald for C$_{39}$H$_{49}$BClN$_4$O$_4$ 683.3535, obsd 683.3544.

Example 5

(6S,8R)-N-[[(1R)-1-[(3aS,4S,6S,7aR)-hexahydro-3a, 5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)thiophenyl] methyl]-amino]-pyrrolo[1,2-a]pyrazine-6-carboxamide.

The title compound was prepared in a procedure similar to that of Example 2. ESMS m/e cald for C$_{38}$H$_{46}$BClF$_3$N$_4$O$_4$S 769.2973, obsd 769.2972.

Example 6

(6S,8R)-N-[[(1R)-1-[(3aS,4S,6S,7aR)-hexahydro-3a, 5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3,4-difluorophenyl]methyl] amino]-pyrrolo[1,2-a]pyrazine-6-carboxamide.

The title compound was prepared in a procedure similar to that of Example 2. ESMS m/e cald for C$_{38}$H$_{45}$BClF$_2$N$_4$O$_4$ 705.3191, obsd 705.3217.

Example 7

(6S, 8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3,5-bis (trifluoromethyl)phenyl]methyl]-amino]- pyrrolo[1, 2-a]pyrazine-6-carboxamide.

The title compound was prepared in a procedure similar to that of Example 2. ESMS m/e cald for C$_{40}$H$_{45}$BClF$_6$N$_4$O$_4$ 805.3127, obsd 805.3143.

Example 8

(6S,8R)-N-[[(1R)-1-[(3aS,4S,6S,7aR)-hexahydro-3a, 5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[1,3-benzodioxolo-5-methyl] amino]-pyrrolo[1,2-a]pyrazine-6-carboxamide.

The title compound was prepared in a procedure similar to that of Example 2. ESMS m/e cald for C$_{39}$H$_{47}$BClN$_4$O$_6$ 713.3278, obsd 713.3282.

Example 9

(6S, 8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-phenylpropyl)-3-[[[3-trifluoromethylphenyl]methyl]amino]-pyrrolo [1,2-a]pyrazine-6-carboxamide.

The title compound was prepared in a procedure similar to that of Example 2 but using difluoroethyl boronic ester as a serine trap. ESMS m/e cald for C$_{38}$H$_{44}$BClF$_5$N$_4$O$_4$ 761.3065, obsd 761.3090.

Example 10

(6S,8R)-N-[[(1R)-1-[(3aS,4S,6S,7aR)-hexahydro-3a, 5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-biphenyl]methyl]amino]-pyrrolo[1,2-a]pyrazine-6-carboxamide.

The title compound was prepared in a procedure similar to that of Example 2. ESMS m/e 745.4 (M+H),

Example 11

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-nitro-phenyl]methyl]
amino]-pyrrolo[1,2-a]pyrazine-6-carboxamide.

The title compound was prepared in a procedure similar to that of Example 2. ESMS m/e 714.3 (M+H).

Example 12

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[2-furanyllmethyl]amino]-
pyrrolo[1,2-a]pyrazine-6-carboxamide.

The title compound was prepared in a procedure similar to that of Example 2. ESMS m/e 681.4 (M+Na).

Example 13

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[1-hexyl]amino]- pyrrolo[1,2-a]
pyrazine-6-carboxamide.

The title compound was prepared in a procedure similar to that of Example 2. ESMS m/e 663.4 (M+H).

Example 14

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[(methyl)amino]- pyrrolo[1,2-a]
pyrazine-6-carboxamide.

The title compound was prepared in a procedure similar to that of Example 2. ESMS m/e 593.3 (M+H).

Example 15

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[phenylmethyl]amino]- pyrrolo
[1,2-a]pyrazine-6-carboxamide.

The title compound was prepared in a procedure similar to that of Example 2. ESMS m/e 691.3 (M+Na).

Example 16

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-fluoro-phenyl]methyl]
amino]-pyrrolo[1,2-a]pyrazine-6-carboxamide.

The title compound was prepared in a procedure similar to that of Example 2. ESMS m/e 709.3 (M+Na).

Example 17

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-chloro-phenyl]methyl]
amino]-pyrrolo[1,2-a]pyrazine-6-carboxamide.

The title compound was prepared in a procedure similar to that of Example 2. ESMS m/e 725.3 (M+Na).

Example 18

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-methoxy-phenyl]methyl]
amino]-pyrrolo[1,2-a]pyrazine-6-carboxamide.

The title compound was prepared in a procedure similar to that of Example 2. ESMS m/e 721.3 (M+Na).

Example 19

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[4-methoxy-phenyl]methyl]
amino]-pyrrolo[1,2-a]pyrazine-6-carboxamide.

The title compound was prepared in a procedure similar to that of Example 2. ESMS m/e 721.4 (M+Na).

Example 20

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-cyano-phenyl]methyl]
amino]-pyrrolo1,2-a]pyrazine-6-carboxamide.

The title compound was prepared in a procedure similar to that of Example 2. ESMS m/e 716.2 (M+Na).

Example 21

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
benzyl-3-[[[3-trifluoromethyl-phenyl]methyl]amino]-
pyrrolo[1,2-a]pyrazine-6-carboxamide.

The title compound was prepared in a procedure similar to that of Example 2. ESMS m/e 731.3 (M+Na), cald for $C_{37}H_{42}BClF_3N_4O_4$ 709.2930, obsd 709.2935.

Example 22

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-naphthylmethyl)-3-[[[3-trifluromethyl-phenyl]
methyl]amino]-pyrrolo[1,2-a]pyrazine-6-
carboxamide.

The title compound was prepared in a procedure similar to that of Example 2. ESMS m/e 781.3 (M+Na), cald for $C_{41}H_{44}BClF_3N_4O_4$ 759.3073, obsd 759.3085.

Example 23

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(4-dimethylethylbenzyl)-3-[[[3-trifluromethyl-
phenyl]methyl]amino]-pyrrolo[1,2-a]pyrazine-6-
carboxamide.

The title compound was prepared in a procedure similar to that of Example 2. ESMS m/e 787.4 (M+Na), cald for $C_{41}H_{50}BClF_3N_4O_4$ 765.3603, obsd 765.3584.

Example 24

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(4-methylbenzyl)-3-[[[3-trifluromethyl-phenyl]
methyl]amino]-pyrrolo[1,2-a]pyrazine-6-
carboxamide.

The title compound was prepared in a procedure similar to that of Example 2. ESMS m/e 745.3 (M+Na), cald for $C_{38}H_{44}BClF_3N_4O_4$ 723.3143, obsd 723.3120.

Example 25

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-trifluoromethylbenzyl)-3-[[[3-trifluromethyl-phenyl]methyl]amino]-pyrrolo[1,2-a]pyrazine-6-carboxamide.

The title compound was prepared in a procedure similar to that of Example 2. ESMS m/e 799.3 (M+Na), cald for $C_{38}H_{41}BClF_6N_4O_4$ 777.2821, obsd 777.2817.

Example 26

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-benzyl-3-[[[3-cyano-phenyl]methyl]amino]-pyrrolo[1,2-a]pyrazine-6-carboxamide.

The title compound was prepared in a procedure similar to that of Example 2. ESMS m/e 702.2 (M+Na), cald for $C_{38}H_{44}BClN_5O_4$ 680.3231, obsd 680.3203.

Example 27

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-methylbenzyl)-3-[[[3-trifluromethyl-phenyl]methyl]amino]-pyrrolo[1,2-a]pyrazine-6-carboxamide.

The title compound was prepared in a procedure similar to that of Example 2. ESMS m/e 745.2 (M+Na), cald for $C_{38}H_{44}BClF_3N_4O_4$ 723.3096, obsd 723.3094.

Example 28

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3,5-dimethylbenzyl)-3-[[[3-trifluromethyl-phenyl]methyl]amino]-pyrrolo[1,2-a]pyrazine-6-carboxamide.

The title compound was prepared in a procedure similar to that of Example 2. ESMS m/e 759.2 (M+Na), cald for $C_{39}H_{46}BClF_3N_4O_4$ 737.3300, obsd 737.3276.

Example 29

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-methoxybenzyl)-3-[[[3-trifluromethyl-phenyl]methyl]amino]-pyrrolo[1,2-alpyrazine-6-carboxamide.

The title compound was prepared in a procedure similar to that of Example 2. ESMS m/e 761.2 (M+Na), cald for $C_{38}H_{44}BClF_3N_4O_5$ 739.3093, obsd 739.3069.

Example 30

(6S)-1-Chloro-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8,8-dimethyl-4-oxo-3-[[[3-(trifluoromethyl)phenyl]methyl]amino]pyrrolo[1,2-a]pyrazine-6-carboxamide.

The title compound was prepared in a procedure similar to that of Example 2. ESMS m/e 669.3 (M+Na), cald for $C_{32}H_{40}BClF_3N_4O_4$ 647.2795, obsd 647.2789.

Example 31

(6S,8R)-1-Chloro-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide.

The title compound was prepared in a procedure similar to that of Example 2. ESMS m/e 773.2 (M+Na), cald for $C_{40}H_{48}BClF_3N_4O_4$ 751.3393, obsd 751.3381.

Example 32

(6S,8S)-1-Chloro-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide.

The title compound was prepared in a procedure similar to that of Example 2. ESMS m/e 773.2 (M+Na), cald for $C_{40}H_{48}BClF_3N_4O_4$ 751.3393, obsd 751.3428.

Example 33

(6S)-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8,8-dimethyl-4-oxo-3-[[[3-(trifluoromethyl)phenyl]methyl]amino]pyrrolo[1,2-a]pyrazine-6-carboxamide.

The title compound was prepared in a procedure similar to that of Example 2. ESMS m/e 613.3 (M+H), cald for $C_{32}H_{41}BF_3N_4O_4$ 613.3180, obsd 613.3183.

Example 34

(6S,8R)-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide.

The title compound was prepared in a procedure similar to that of Example 2. ESMS m/e 717.3 (M+H), cald for $C_{40}H_{49}BF_3N_4O_4$ 717.3787, obsd 717.3793.

Example 35

(6S,8S)-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide.

The title compound was prepared in a procedure similar to that of Example 2. ESMS m/e 717.3 (M+H), cald for $C_{40}H49BF3N_4O_4$ 717.3787, obsd 717.3814.

Example 36

(6S)-1-Chloro-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-4-oxo-8,8-di(3-phenylpropyl)- 3-[[[3-(trifluoromethyl)phenyl]methyl]amino]pyrrolo[1,2-a]pyrazine-6-carboxamide.

The title compound was prepared in a procedure similar to that of Example 2. ESMS m/e 855.3 (M+H).

Example 37

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-naphthylmethoxy)-3-[[[3-trifluromethyl-phenyl]
methyl]amino]-pyrrolo[1,2-a]pyrazine-6-
carboxamide.

The title compound was prepared in a procedure similar to that of Example 2. ESMS m/e 797.3 (M+Na), cald for $C_{41}H_{44}BClF_3N_4O_5$ 775.3030, obsd 775.3038.

Example 38

(6S,8R)-N-[[(1R)-1-[(3aS,4S,6S,7aR)-hexahydro-3a,
5,5-trimethyl-4,6-methano-1,3,2-benzodioxaborol-2-
yl]-3-(4-trifluoromethylphenylethyl)]-1-chloro-4,6,7,
8-tetrahydro-4-oxo-8-(3-methoxybenzyl)-3-[[3-
trifluromethyl-phenyl]methyl]amino]-pyrrolo[1,2-a]
pyrazine-6-carboxamide.

The title compound was prepared in a procedure similar to that of Example 2. ESMS m/e 907.2 (M+H).

Example 39

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-(2-naphthyl)propyl)-3-[[[3-trifluromethylphenyl]
methyl]amino]-pyrrolo[1,2-a]pyrazine-6-
carboxamide.

The title compound was prepared in a procedure similar to that of Example 2. ESMS m/e 809.2 (M+Na), cald for $C_{43}H_{48}BClF_3N_4O_4$ 787.3395, obsd 787.3402.

Example 40

(6S,8R)-N-[[(1R)-1-[(3aS,4S,6S,7aR)-hexahydro-3a,
5,5-trimethyl-4,6-methano-1,3,2-benzodioxaborol-2-
yl]-3-ethyl]-1-chloro-4,6,7,8-tetrahydro-4-oxo-8-(3-
(2-naphthyl)propyl)-3-[[[3-trifluromethylphenyl]
methyl]amino]-pyrrolo[1,2-a]pyrazine-6-
carboxamide.

The title compound was prepared in a procedure similar to that of Example 2. ESMS m/e 797.2 (M+Na), cald for $C_{42}H_{48}BClF_3N_4O_4$ 775.3407, obsd 775.3388.

Example 41

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-(2-naphthyl)propyl)-3-[[[3-
trifluromethylthiophenyl]methyl]amino]-pyrrolo[1,
2-a]pyrazine-6-carboxamide.

The title compound was prepared in a procedure similar to that of Example 2. ESMS m/e 841.1 (M+Na).

Example 42

(6S,8R)-N-[[(1R)-1-[(3aS,4S,6S,7aR)-hexahydro-3a,
5,5-trimethyl-4,6-methano-1,3,2-benzodioxaborol-2-
yl]-3-ethyl]-1-chloro-4,6,7,8-tetrahydro-4-oxo-8-(3-
(2-naphthyl)propyl)-3-[[[3-trifluromethylthiophenyl]
methyl]amino]-pyrrolo[1,2-a]pyrazine-6-
carboxamide.

The title compound was prepared in a procedure similar to that of Example 2. ESMS m/e 829.1 (M+Na).

Example 43

(6S,8R)-N-[[(1R)-1-[(3aS,4S,6S,7aR)-hexahydro-3a,
5,5-trimethyl-4,6-methano-1,3,2-benzodioxaborol-2-
yl]-3-[2,2-difluoroethyl]]-1-chloro-4,6,7,8-
tetrahydro-4-oxo-8-(3-(2-naphthyl)propyl)-3-[[[3-
trifluoromethylphenyl]methyl]amino]-pyrrolo[1,2-a]
pyrazine-6-carboxamide.

The title compound was prepared in a procedure similar to that of Example 2 but using difluoroethyl boronic ester as a serine trap. ESMS m/e 811.2 (M+H).

Example 44

(6S,8R)-N-[[(1R)-1-[(3aS,4S,6S,7aR)-hexahydro-3a,
5,5-trimethyl-4,6-methano-1,3,2-benzodioxaborol-2-
yl]-3-[2,2-difluoroethyl]]-1-chloro-4,6,7,8-
tetrahydro-4-oxo-8-(3-(2-naphthyl)propyl)-3-[[[3-
trifluoromethylthiophenyl]methyl]amino]-pyrrolo[1,
2-a]pyrazine-6-carboxamide.

The title compound was prepared in a procedure similar to that of Example 2 but using difluoroethyl boronic ester as a serine trap. ESMS m/e 843.1 (M+H).

Example 45

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[2-propyl]amino]-pyrrolo[1,2-a]
pyrazine-6-carboxamide.

The title compound was prepared in a procedure similar to that of Example 2. ESMS m/e 643.3 (M+H), cald for $C_{34}H_{47}BClN_4O_4$ 621.3341, obsd 621.3351.

Example 46

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-(2-methylpropyl)amino]-pyrrolo
[1,2-a]pyrazine-6-carboxamide.

The title compound was prepared in a procedure similar to that of Example 2. ESMS m/e 657.3 (M+H), cald for $C_{35}H_{49}BClN_4O_4$ 635.3583, obsd 635.3559.

Example 47

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-(cyclohexylmethyl)amino]-
pyrrolo[1,2-a]pyrazine-6-carboxamide.

The title compound was prepared in a procedure similar to that of Example 2. ESMS m/e 697.3 (M+H), cald for $C_{38}H_{53}BClF_3N_4O_4$ 675.3815, obsd 675.3832.

Example 48

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-trifluoromethoxyphenyl]
methyl]amino]-pyrrolo[1,2-a]pyrazine-6-
carboxamide.

The title compound was prepared in a procedure similar to that of Example 2. ESMS m/e 775.3 (M+Na), cald for $C_{39}H_{46}BClN_4O_5$ 753.3223, obsd 753.3221.

Example 49

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3- [[2-difluoromethoxyphenyl]
methyl]amino]-pyrrolo[1,2-a]pyrazine-6-
carboxamide.

The title compound was prepared in a procedure similar to that of Example 2. ESMS m/e 757.3 (M+Na), cald for $C_{39}H_{47}BClF_2N_4O_5$ 735.3314, obsd 735.3314.

Example 50

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[2-pyridinyl]methylamino]-
pyrrolo[1,2-a]pyrazine-6-carboxamide.

The title compound was prepared in a procedure similar to that of Example 2. ESMS m/e 670.4 (M+H), cald for $C_{37}H_{46}BClN_5O_4$ 670.3334, obsd 670.3333.

Example 51

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[4-pyridinyl]methyl]amino]-
pyrrolo[1,2-a]pyrazine-6-carboxamide.

The title compound was prepared in a procedure similar to that of Example 2. ESMS m/e 670.3 (M+H), cald for $C_{37}H_{46}BClN_5O_4$ 670.3334, obsd 670.3361.

Example 52

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-8-
(3-phenylpropyl)-3-[[[3-pyridinyl]methyl]amino]-
pyrrolo[1,2-a]pyrazine-6-carboxamide.

The title compound was prepared in a procedure similar to that of Example 2. ESMS m/e 670.3 (M+H), cald for $C_{37}H_{46}BClN_5O_4$ 670.3334, obsd 670.3355.

Example 53

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-3-
[[[3-trifluoromethylphenyl]methyl]amino]-pyrrolo[1,
2-a]pyrazine-6-carboxamide.

The title compound was prepared in a procedure similar to that of Example 2. ESMS m/e 641.2 (M+Na), cald for $C_{30}H_{36}BClF_3N_4O_4$ 619.2530, obsd 619.2500.

Example 54

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-3-
[[[5-methyl-2-pyrazinyl]methyl]amino]-pyrrolo
[1,2-a]pyrazine-6-carboxamide.

The title compound was prepared in a procedure similar to that of Example 2. ESMS m/e 707.3 (M+Na), cald for $C_{37}H_{47}BClN_6O_4$ 685.3429, obsd 685.3435.

Example 55

(6S,8R)-N-[[(1R)-1-[(3aS,4S,6S,7aR)-hexahydro-
3a,,S5-trimethyl-4,6-methano-1,3,2-
benzodioxaborol-2-yl]-3-butenyl]-4,6,7,8-
tetrahydro-4-oxo-3-[[[3-trifluoromethylphenyl]
methyl]amino]-pyrrolo[1,2-a]pyrazine-6-
carboxamide.

The title compound was prepared in a procedure similar to that of Example 2. ESMS m/e 725.5 (M+Na), cald for $C_{39}H_{47}BF_3N_4O_4$ 703.3632, obsd 703.3633.

Example 56

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7,8-tetrahydro-4-oxo-3-
[[[tert-butoxylcarbonyl]methyl]amino]-pyrrolo
[1,2-a]pyrazine-6-carboxamide.

The title compound was prepared in a procedure similar to that of Example 2. ESMS m/e 715.4 (M+Na), cald for $C_{37}H_{51}BClN_4O_6$ 693.3603, obsd 693.3602.

Example 57

(6S,8R)-N-[[(1R)-1-[(3aS,4S,6S,7aR)-hexahydro-3a,
5,5-trimethyl-4,6-methano-1,3,2-benzodioxaborol-2-
yl]-3-butenyl]-1-chloro-4,6,7, 8-tetrahydro-4-oxo-3-
[[(2-tert-butoxylcarbonyl)ethyl]amino]-pyrrolo
[1,2-a]pyrazine-6-carboxamide.

The title compound was prepared in a procedure similar to that of Example 2. ESMS m/e 729.3 (M+Na), cald for $C_{38}H_{53}BClN_4O_6$ 707.3711, obsd 707.3720.

Example 58

[(1R) -1-[[[(6S, 8R) -1-chloro-4,6,7,8-tetrahydro-4-
oxo-8-(3-phenylpropyl)-3-[[[3-(trifluoromethyl)
phenyl]methyl]-amino]pyrrolo[1,2-a]pyrazin-6-yl]
carbonyl]amino]-3-butenyl]-boronic acid.

Example 2 (25 mg, 0.034 mmmol), phenyl boronic acid (21 mg, 0.17 mmol) in a mixture of $CH_2Cl_2$ (0.6 mL), $Et_2O$ (0.3 mL) and water (0.3 mL) was vigorously stirred for 24 h. The mixture was then extracted with $CH_2Cl_2$, dried over $Na_2SO_4$, and the title compound was purified by a prep. TLC plate to give 8 mg of white solid. ESMS m/e 625.1 (M+Na)

Example 59

[(1R)-1-[[[(6S,8R)-1-chloro-4,6,7,8-tetrahydro-4-
oxo-8-[3-(2-naphthyl)propyl]-3-[[[3-
(trifluoromethyl)phenyl]methyl]-amino]pyrrolo [2-a]
pyrazin-6-yl]carbonyl]amino]-3-butenyl]-boronic
acid.

The title compound was prepared in a procedure similar to that of Example 58. ESMS m/e 675.1 (M+Na).

Example 60

[(1R)-1-[[[(6S,8R)-1-chloro-4,6,7,8-tetrahydro-4-
oxo-8-[3-(2-naphthyl)propyl]-3-[[[3-
(trifluoromethyl)phenyl]methyl]-amino]pyrrolo
[1,2-a]pyrazin-6-yl]carbonyl]amino]-3-ethyl]-
boronic acid.

The title compound was prepared in a procedure similar to that of Example 58. ESMS m/e 663.1 (M+Na).

TABLE 1

| Ex# | A3 | R6 | R3 | R1 | (M + 1) + |
|---|---|---|---|---|---|
| 1 | (4-MeO-phenyl)CH₂— | Cl | —H | —CH₂CH=CH₂ | 581.3 |
| 2 | (3-CF₃-phenyl)CH₂— | Cl | —CH₂CH₂CH₂Ph | —CH₂CH=CH₂ | 737.3 |
| 3 | (2,5-F₂-phenyl)CH₂— | Cl | —CH₂CH₂CH₂Ph | —CH₂CH=CH₂ | 705.3 |
| 4 | (3-CH₃-phenyl)CH₂— | Cl | —CH₂CH₂CH₂Ph | —CH₂CH=CH₂ | 683.4 |
| 5 | (3-CF₃S-phenyl)CH₂— | Cl | —CH₂CH₂CH₂Ph | —CH₂CH=CH₂ | 769.3 |
| 6 | (3,4-F₂-phenyl)CH₂— | Cl | —CH₂CH₂CH₂Ph | —CH₂CH=CH₂ | 705.3 |
| 7 | (3,5-(CF₃)₂-phenyl)CH₂— | Cl | —CH₂CH₂CH₂Ph | —CH₂CH=CH₂ | 805.3 |
| 8 | (1,3-benzodiaxolo-5-yl)CH₂— | Cl | —CH₂CH₂CH₂Ph | —CH₂CH=CH₂ | 713.3 |
| 9 | (3-CF₃-phenyl)CH₂— | Cl | —CH₂CH₂CH₂Ph | —CH₂CHF₂ | 761.3 |
| 10 | (3-biphenyl)CH₂— | Cl | —CH₂CH₂CH₂Ph | —CH₂CH=CH₂ | 745.4 |
| 11 | (3-NO₂-phenyl)CH₂— | Cl | —CH₂CH₂CH₂Ph | —CH₂CH=CH₂ | 714.3 |
| 12 | (2-furanyl)CH₂— | Cl | —CH₂CH₂CH₂Ph | —CH₂CH=CH₂ | 659.3 |
| 13 | n-hexyl- | Cl | —CH₂CH₂CH₂Ph | —CH₂CH=CH₂ | 663.4 |
| 14 | methyl- | Cl | —CH₂CH₂CH₂Ph | —CH₂CH=CH₂ | 593.3 |
| 15 | (phenyl)CH₂— | Cl | —CH₂CH₂CH₂Ph | —CH₂CH=CH₂ | 669.3 |
| 16 | (3-F-phenyl)CH₂— | Cl | —CH₂CH₂CH₂Ph | —CH₂CH=CH₂ | 687.3 |
| 17 | (3-Cl-phenyl)CH₂— | Cl | —CH₂CH₂CH₂Ph | —CH₂CH=CH₂ | 703.3 |
| 18 | (3-MeO-phenyl)CH₂— | Cl | —CH₂CH₂CH₂Ph | —CH₂CH=CH₂ | 699.3 |
| 19 | (4-MeO-phenyl)CH₂— | Cl | —CH₂CH₂CH₂Ph | —CH₂CH=CH₂ | 699.4 |
| 20 | (3-CN-phenyl)CH₂— | Cl | —CH₂CH₂CH₂Ph | —CH₂CH=CH₂ | 694.2 |
| 21 | (3-CF₃-phenyl)CH₂— | Cl | —CH₂Ph | —CH₂CH=CH₂ | 709.3 |
| 22 | (3-CF₃-phenyl)CH₂— | Cl | —CH₂(2-naphthiene) | —CH₂CH=CH₂ | 759.3 |
| 23 | (3-CF₃-phenyl)CH₂— | Cl | —CH₂(4-tert-butylbenezene) | —CH₂CH=CH₂ | 765.4 |
| 24 | (3-CF₃-phenyl)CH₂— | Cl | —CH₂Ph-4-Me | —CH₂CH=CH₂ | 723.4 |
| 25 | (3-CF₃-phenyl)CH₂— | Cl | —CH₂Ph-4-CF3 | —CH₂CH=CH₂ | 777.3 |
| 26 | (3-CN-phenyl)CH₂— | Cl | —CH₂Ph-4-Me | —CH₂CH=CH₂ | 680.3 |
| 27 | (3-CF₃-phenyl)CH₂— | Cl | —CH₂Ph-3-Me | —CH₂CH=CH₂ | 723.3 |
| 28 | (3-CF₃-phenyl)CH₂— | Cl | —CH₂(3,5-Me₂)-phenyl | —CH₂CH=CH₂ | 737.3 |
| 29 | (3-CF₃-phenyl)CH₂— | Cl | —CH₂Ph-3-OMe | —CH₂CH=CH₂ | 739.2 |
| 37 | (3-CF₃-phenyl)CH₂— | Cl | —OCH₂(2-naphthene) | —CH₂CH=CH₂ | 775.3 |
| 38 | (3-CF₃-phenyl)CH₂— | Cl | —OCH₂(2-naphthene) | —CH₂CH₂CH₂—Ph-4-CF₃ | 907.2 |
| 39 | (3-CF₃-phenyl)CH₂— | Cl | —CH₂CH₂CH₂(1-naphthlene) | —CH₂CH=CH₂ | 787.2 |
| 40 | (3-CF₃-phenyl)CH₂— | Cl | —CH₂CH₂CH₂(1-naphthlene) | —CH₂CH₃ | 775.3 |
| 41 | (3-CF₃S-phenyl)CH₂— | Cl | —CH₂CH₂CH₂(1-naphthlene) | —CH₂CH=CH₂ | 819.2 |
| 42 | (3-CF₃S-phenyl)CH₂— | Cl | —CH₂CH₂CH₂(1-naphthlene) | —CH₂CH₃ | 807.2 |
| 43 | (3-CF₃-phenyl)CH₂— | Cl | —CH₂CH₂CH₂(1-naphthlene) | —CH₂CHF₂ | 811.2 |
| 44 | (3-CF₃S-phenyl)CH₂— | Cl | —CH₂CH₂CH₂(1-naphthlene) | —CH₂CHF₂ | 843.1 |
| 45 | 2-propyl- | Cl | —CH₂CH₂CH₂Ph | —CH₂CH=CH₂ | 621.3 |
| 46 | 2-Me-propyl- | Cl | —CH₂CH₂CH₂Ph | —CH₂CH=CH₂ | 635.4 |
| 47 | (Cyclohexyl)CH₂— | Cl | —CH₂CH₂CH₂Ph | —CH₂CH=CH₂ | 675.4 |
| 48 | (3-CF₃O-phenyl)CH₂— | Cl | —CH₂CH₂CH₂Ph | —CH₂CH=CH₂ | 753.3 |
| 49 | (3-CHF₂O-phenyl)CH₂— | Cl | —CH₂CH₂CH₂Ph | —CH₂CH=CH₂ | 735.3 |
| 50 | (2-Pyridinyl)CH₂— | Cl | —CH₂CH₂CH₂Ph | —CH₂CH=CH₂ | 670.4 |
| 51 | (4-Pyridinyl)CH₂— | Cl | —CH₂CH₂CH₂Ph | —CH₂CH=CH₂ | 670.3 |
| 52 | (3-Pyridinyl)CH₂— | Cl | —CH₂CH₂CH₂Ph | —CH₂CH=CH₂ | 670.3 |
| 53 | (3-CF₃-phenyl)CH₂— | Cl | H | —CH₂CH=CH₂ | 619.3 |
| 54 | (5-Me-pyrazinyl)CH₂— | Cl | —CH₂CH₂CH₂Ph | —CH₂CH=CH₂ | 685.4 |
| 55 | (3-CF₃-phenyl)CH₂— | H | —CH₂CH₂CH₂Ph | —CH₂CH=CH₂ | 703.5 |

TABLE 1-continued

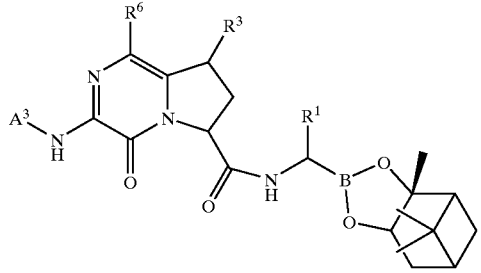

| Ex# | A3 | R6 | R3 | R1 | (M + 1) + |
|---|---|---|---|---|---|
| 56 | (t-BuO)C(=O)CH$_2$— | Cl | —CH$_2$CH$_2$CH$_2$Ph | —CH$_2$CH=CH$_2$ | 693.4 |
| 57 | (t-BuO)C(=O)CH$_2$CH$_2$— | Cl | —CH$_2$CH$_2$CH$_2$Ph | —CH$_2$CH=CH$_2$ | 707.3 |

TABLE 2

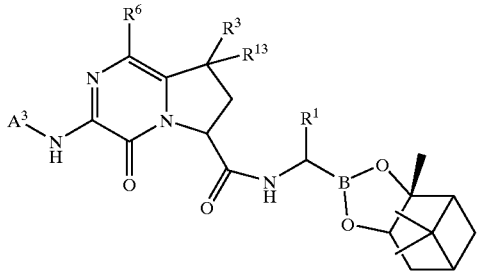

| Ex# | A3 | R6 | R3, R13 | R1 | (M + 1) + |
|---|---|---|---|---|---|
| 30 | (3-CF$_3$-phenyl)CH$_2$— | Cl | R$^3$ = —CH$_3$, R$^{13}$ = —CH$_3$ | —CH$_2$CH=CH$_2$ | 647.3 |
| 31 | (3-CF$_3$-phenyl)CH$_2$— | Cl | R$^3$ = —CH$_3$, R$^{13}$ = —CH$_2$CH$_2$CH$_2$Ph | —CH$_2$CH=CH$_2$ | 751.3 |
| 32 | (3-CF$_3$-phenyl)CH$_2$— | Cl | R$^3$ = —CH$_2$CH$_2$CH$_2$Ph, R$^{13}$ = —CH$_3$ | —CH$_2$CH=CH$_2$ | 751.2 |
| 33 | (3-CF$_3$-phenyl)CH$_2$— | H | R$^3$ = —CH$_3$, R$^{13}$ = —CH$_3$ | —CH$_2$CH=CH$_2$ | 613.3 |
| 34 | (3-CF$_3$-phenyl)CH$_2$— | H | R$^3$ = —CH$_3$, R$^{13}$ = —CH$_2$CH$_2$CH$_2$Ph | —CH$_2$CH=CH$_2$ | 717.3 |
| 35 | (3-CF$_3$-phenyl)CH$_2$— | H | R$^3$ = —CH$_2$CH$_2$CH$_2$Ph, R$^{13}$ = —CH$_3$ | —CH$_2$CH=CH$_2$ | 717.3 |
| 36 | (3-CF$_3$-phenyl)CH$_2$— | Cl | R$^3$ = —CH$_2$CH$_2$CH$_2$Ph, R$^{13}$ = —CH$_2$CH$_2$CH$_2$Ph | —CH$_2$CH=CH$_2$ | 855.3 |

TABLE 3

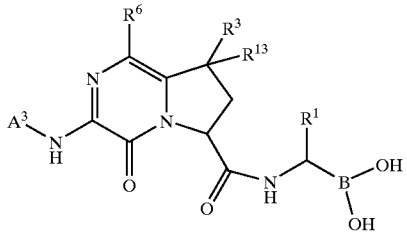

| Ex# | A3 | R6 | R3 | R1 | (M + 1) + |
|---|---|---|---|---|---|
| 58 | (3-CF$_3$-phenyl)CH$_2$— | Cl | —CH$_2$CH$_2$CH$_2$Ph | —CH$_2$CH=CH$_2$ | 603.4 |
| 59 | (3-CF$_3$-phenyl)CH$_2$— | Cl | —CH$_2$CH$_2$CH$_2$(1-naphthlene) | —CH$_2$CH=CH$_2$ | 653.3 |
| 60 | (3-CF$_3$-phenyl)CH$_2$— | Cl | —CH$_2$CH$_2$CH$_2$(1-naphthlene) | —CH$_2$CH3 | 641.3 |

The following Table 4 contains representative examples envisioned by the present invention. At the start of each table is one formula followed by substituents 1a through 1bw demonstrating the intended substitution of $R^1$; substituents 3a through 3an demonstrating the intended substitution of $R^3$; and substituents 9a through 9bn demonstrating the intended substitution of $R^9$. Each entry in each list is intended to be paired with each formulae at the start of Table 4. For example, Example 1100 in Table 4 is intended to be paired with each of formulae 1a, 1b, 1c, 1d, through 1bw of Table 4, as well as each of formulae 3a, 3b, 3c, 3d, . . . through 3an of Table 4, as well as each of formulae 9a, 9b, 9c, 9d, . . . through 9bn of Table 4; thereby representing Example 1100-9a-3a-1a, 1100-9a-3a-1b, 1100-9a-3a-1c, . . . through 1104-9bn-3an-1bw.

As an illustration, Example 1101-9az-31-1k is N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)phenyl]methyl]amino]-pyrrolo[1,2-a]pyrazine-6-carboxamide.

TABLE 4

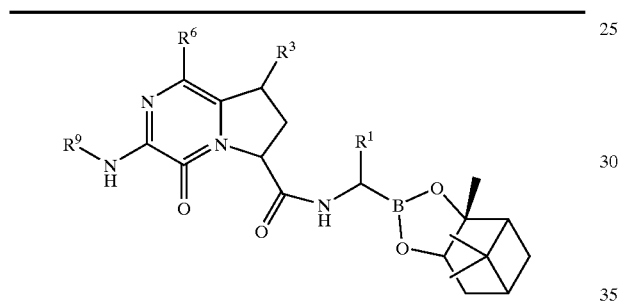

R$^1$ is selected from:

1a: —CH$_2$CH$_3$
1b: —CH$_2$CH$_2$CH$_3$
1c: —CH(CH$_3$)$_2$
1d: —CH$_2$CH$_2$CH$_2$CH$_3$
1e: —CH$_2$CH(CH$_3$)$_2$
1f: —CH$_2$C(CH$_3$)$_3$
1g: —CH$_2$CH$_2$C(CH$_3$)$_3$
1h: —CH$_2$CF$_3$
1i: —CH$_2$CH$_2$CF$_3$
1j: —CH$_2$CH$_2$CH$_2$CF$_3$
1k: —CH$_2$CHCH$_2$
1l: cis-CH$_2$CH=CH(CH$_3$)
1m: —CH$_2$CH$_2$CH=CH
1n: —CH$_2$CH$_2$CH=C(CH$_3$)$_2$
1o: benzyl
1p: phenpropyl
1q: —CH$_2$CO$_2$H
1r: —CH$_2$CO$_2$C(CH$_3$)$_3$
1s: —CH$_2$CH$_2$CH$_2$CH$_2$NH$_2$
1t: (cyclobutyl)methyl-
1u: (cyclobutyl)propyl-
1v: cyclobutyl
1w: cyclohexyl
1x: (2-methylphenyl)ethyl-
1y: (3-methylphenyl)ethyl-
1z: (4-methylphenyl)ethyl-
1aa: (2-fluorophenyl)ethyl-
1ab: (3-fluorophenyl)ethyl-
1ac: (4-fluorophenyl)ethyl-
1ad: (2-bromophenyl)ethyl-
1ae: (4-bromophenyl)ethyl-
1af: (4-phenyl-phenyl)ethyl-
1ag: (2,4-dimethylphenyl)ethyl-
1ah: —CH$_2$CH$_2$CH$_2$C(CH$_3$)$_3$
1ai: —CH$_2$CH$_2$CH$_2$CH(CH$_3$)$_2$
1aj: —CH$_2$CH$_2$CH$_2$CH(CH$_2$CH$_3$)$_2$ TABLE 4-continued

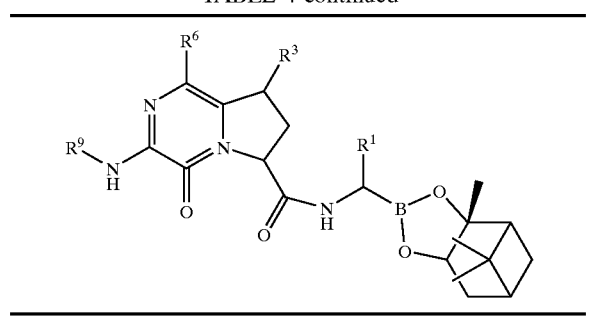

1ak: —CH$_2$CH$_2$CH$_2$CH$_2$CH$_3$
1al: —CH$_2$CH$_2$CHC(CH$_3$)$_2$
1am: —CH$_2$CH$_2$CH$_2$CH$_2$CH$_2$CH$_3$
1an: —CH$_2$CHF$_2$
1ao: —CH$_2$CH$_2$CHF$_2$
1ap: —CH$_2$CH$_2$CH$_2$CHF$_2$
1aq: —CH=CH$_2$
1ar: —CH=CHCH$_3$
1as: trans-CH$_2$CH=CH(CH$_3$)
1at: —CH$_2$CH=C(CH$_3$)$_2$
1au: phenyl
1av: phenethyl
1aw: phenbutyl
1ax: —CH$_2$CH$_2$CO$_2$H
1ay: —CH$_2$CH$_2$CO$_2$C (CH$_3$)$_3$
1az: (naphth-2-yl)ethyl-
1ba: (cyclobutyl)ethyl-
1bb: cyclapropyl
1bc: cyclopentyl
1bd: (4-ethylphenyl)ethyl-
1be: (4-i-propylphenyl)ethyl-
1bf: (4-t-butylphenyl)ethyl-
1bg: (4-hydroxyphenyl)ethyl-
1bh: (2-chlorophenyl)ethyl-
1bi: (3-chlorophenyl)ethyl-
1bj: (4-chlorophenyl)ethyl-
1bk: (3-bromophenyl)ethyl-
1bm: (4-phenoxy-phenyl)ethyl-
1bn: (2,5-dimethylphenyl)ethyl-
1bo: (2,6-difluorophenyl)ethyl-
1bp: (4-cyclohexyl-phenyl)ethyl-
1bq: (4-cyclopentyl-phenyl)ethyl-
1br: (4-cyclobutyl-phenyl)ethyl-
1bs: (4-cyclopropyl-phenyl)ethyl-
1bt: (2-trifluoromethylphenyl)ethyl-
1bu: (3-trifluoromethylphenyl)ethyl-
1bv: (4-trifluoromethylphenyl)ethyl-
1bw: (2,3,4,5,6-pentafluorophenyl)ethyl- R$^3$ is selected from:

3a: —H
3b: —CH$_3$
3c: —CH$_2$CH$_3$
3d: —CH$_2$CH$_2$CH$_3$
3e: —CH(CH$_3$)$_2$
3f: —CH$_2$CH$_2$CH$_2$CH$_3$
3g: —CH$_2$CH(CH$_3$)$_2$
3h: —CH$_2$C(CH$_3$)$_3$
3i: —CH$_2$CH$_2$C(CH$_3$)$_3$
3j: —CH$_2$Ph
3k: —CH$_2$CH$_2$Ph
3l: —CH$_2$CH$_2$CH$_2$Ph
3m: —CH$_2$(1-naphthyl)
3n: —CH$_2$CH$_2$(1-naphthyl)
3o: —CH$_2$CH$_2$CH$_2$(1-naphthyl)
3p: —CH$_2$(2-naphthyl)
3q: —CH$_2$CH$_2$(2-naphthyl)
3r: —CH$_2$CH$_2$CH$_2$(2-naphthyl)
3s: —CH$_2$(cyclopropyl)
3t: —CH$_2$CH$_2$(cyclopropyl)
3u: —CH$_2$CH$_2$CH$_2$(cyclopropyl)
3v: —CH$_2$(cyclopentyl)
3w: —CH$_2$CH$_2$(cyclopentyl)
3x: —CH$_2$CH$_2$CH$_2$(cyclopentyl)

TABLE 4-continued

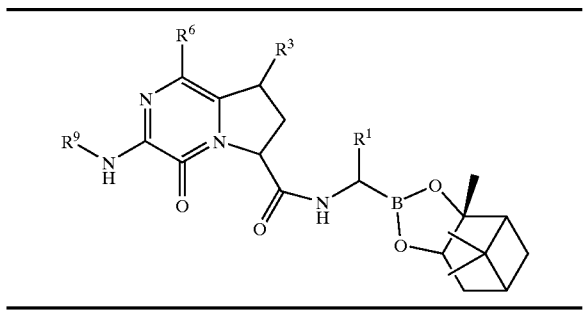

3y: —CH₂(cyclobutyl)
3z: —CH₂CH₂(cyclobutyl)
3aa: —CH₂CH₂CH₂(cyclobutyl)
3ab: —CH₂(cyclohexyl)
3ac: —CH₂CH₂(cyclohexyl)
3ad: —CH₂CH₂CH₂(cyclohexyl)
3ae: —CH₂(Ph-4-t-Bu)
3af: —CH₂(Ph-4-Me)
3ag: —CH₂(Ph-4-MeO)
3ah: —CH₂(Ph-4-CF₃)
3ai: —CH₂(Ph-3-t-Bu)
3aj: —CH₂(Ph-3-Me)
3ak: —CH₂(Ph-3-MeO)
3al: —CH₂(Ph-3-CF₃)
3am: —CH₂(Ph-3,5-diMe)
3an: —CH₂(Ph-3,5-diMeO)
3ao:
3ap:
3aq:
3ar:
3as:
3at:
3au:
3av:
3aw:
3ax:
3ay:
3az:

R⁹ is selected from:

9a: methyl
9b: propyl
9c: pentyl
9d: trifluoromethyl
9e: phenylethyl
9f: (3-phenyl-phenyl)methyl-
9g: (2-methylphenyl)methyl-
9h: (4-methylphenyl)methyl-
9i: (3-fluorophenyl)methyl-
9j: (2-chlorophenyl)methyl
9k: (4-chlorophenyl)methyl
9l: (3-bromophenyl)methyl
9m: (2-cyanophenyl)methyl-
9n: (4-cyanophenyl)methyl-
9o: (3-nitrophenyl)methyl-
9p: (2-aminophenyl)methyl-
9q: (4-aminophenyl)methyl-
9r: (3-CF₃SO₂-phenyl)methyl-
9s: (2-CF₃-phenyl)methyl-
9t: (4-CF₃-phenyl)methyl-
9u: (3-methoxyphenyl)methyl-
9v: (2-CF₃O-phenyl)methyl-
9w: (4-CF₃O-phenyl)methyl-
9x: (3-CF₃S-phenyl)methyl-
9y: (3,5-diCF₃-phenyl)methyl-
9z: (3,5-diCl-phenyl)methyl-
9aa: (3,4-diCl-phenyl)methyl-
9ab: (2,5-diF-phenyl)methyl-
9ac: (2-furanyl)methyl-
9ad: (2-pyridyl)methyl-
9ae: (4-pyridyl)methyl-
9af: (cyclopropyl)methyl-
9ag: (cyclopentyl)methyl-
9ah: ethyl TABLE 4-continued

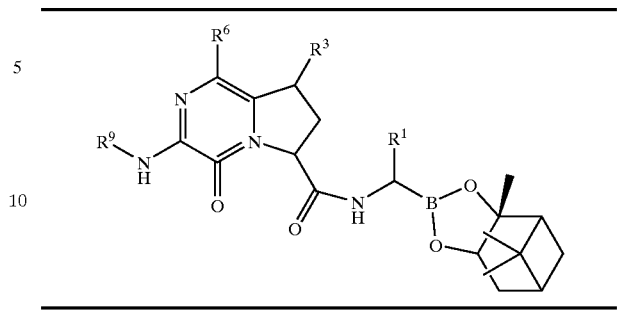

9ai: butyl
9aj: hexyl
9ak: phenylmethyl
9al: phenylpropyl
9am: (4-phenyl-phenyl)methyl-
9an: (3-methylphenyl)methyl-
9ao: (2-fluorophenyl)methyl-
9ap: (4-fluorophenyl)methyl-
9aq: (3-chlorophenyl)methyl-
9ar: (2-bromophenyl)methyl-
9as: (4-bromophenyl)methyl-
9at: (3-cyanophenyl)methyl-
9au: (2-nitrophenyl)methyl-
9av: (4-nitrophenyl)methyl-
9aw: (3-aminophenyl)methyl-
9ax: (2-CF₃SO₂-phenyl)methyl-
9ay: (4-CF₃SO₂-phenyl)methyl-
9az: (3-CF₃-phenyl)methyl-
9ba: (2-methoxyphenyl)methyl-
9bb: (4-methoxyphenyl)methyl-
9bc: (3-CF₃O-phenyl)methyl-
9bd: (2-CF₃S-phenyl)methyl-
9be: (4-CF₃S-phenyl)methyl-
9bf: (3,4-diCF₃-phenyl)methyl-
9bg: (2,5-diCl-phenyl)methyl-
9bh: (3,5-diF-phenyl)methyl-
9bi: (3,4-diF-phenyl)methyl-
9bj: (3-furanyl)methyl-
9bk: (3-pyridyl)methyl-
9bl: (1,3-benzodioxolo-5-yl)methyl-
9bm: (cyclobutyl)methyl-
9bn: (cyclohexyl)methyl-

| Ex# | R⁹ | R⁶ | R³ | R¹ |
|---|---|---|---|---|
| 1100 | 9a–9bn | H | 3a–3am | 1a–1bw |
| 1101 | 9a–9bn | Cl | 3a–3am | 1a–1bw |
| 1102 | 9a–9bn | methyl | 3a–3am | 1a–1bw |
| 1103 | 9a–9bn | ethyl | 3a–3am | 1a–1bw |
| 1104 | 9a–9bn | cyclopropyl | 3a–3am | 1a–1bw |

UTILITY

The compounds of Formula (I) are expected to inhibit the activity of Hepatitis C Virus NS3 protease and, therefore, to possess utility in the cure and prevention of HCV infections. The NS3 protease inhibition is demonstrated using assays for NS3 protease activity, for example, using the assay described below for assaying inhibitors of NS3 protease. The compounds of Formula (I) are expected to show activity against NS3 protease in cells, as demonstrated by the cellular assay described below. A compound is considered to be active if it has an $IC_{50}$ value of less than about 100 $\mu$M in this assay. It is more preferred if it has an $IC_{50}$ value of less than about 60 $\mu$M. It is even more preferred if it has an $IC_{50}$ value of less than about 1 $\mu$M.

It is most preferred if it has an $IC_{50}$ value of less than about 0.1 $\mu$M. Compounds of the present invention have been shown to have an $IC_{50}$ value of less than about 100uM in this assay.

Expression and Purification of NS3 Protease

The plasmid cf1SODp600, containing the complete coding region of HCV NS3 protease, genotype 1a, was obtained from ATCC (database accession: DNA Seq. Acc. M62321, originally deposited by Chiron Corporation). PCR primers were designed that allow amplification of the DNA fragment encoding the NS3 protease catalytic domain (amino acids 1 to 192) as well as its two N-terminal fusions, a 5 amino acid leader sequence MGAQH (serving as a expression tag) and a 15 amino acid His tag MRGSHHHHHHMGAQH. The NS3 protease constructs were cloned in the bacterial expression vector under the control of the T7 promoter and transformed in E. coli BL 21 (DE3) cells. Expression of the NS3 protease was obtained by addition of 1 mM IPTG and cells were growing for additional 3h at 25° C. The NS3 protease constructs have several fold difference in expression level, but exhibit the same level of solubility and enzyme specific activity. A typical 10 L fermentation yielded approximately 200 g of wet cell paste. The cell paste was stored at −80° C. The NS3 protease was purified based on published procedures (Steinkuhler C. et al. *Journal of Virology* 70, 6694–6700, 1996 and Steinkuhler C. et al. *Journal of Biological Chemistry* 271, 6367–6373, 1996.) with some modifications. Briefly, the cells were resuspended in lysis buffer (10 mL/g) containing PBS buffer (20 mM sodium phosphate, pH 7.4, 140 mM NaCl), 50% glycerol, 10 mM DTT, 2% CHAPS and 1 mM PMSF. Cell lysis was performed with use of microfluidizer. After homogenizing, DNase was added to a final concentration 70 U/mL and cell lysate was incubated at 4° C. for 20 min. After centrifugation at 18,000 rpm for 30 min at 4° C. supernatant was applied on SP Sepharose column (Pharmacia), previously equilibrated at a flow rate 3 mL/min in buffer A (PBS buffer, 10% glycerol, 3 mM DTT). The column was extensively washed with buffer A and the protease was eluted by applying 25 column volumes of a linear 0.14–1.0 M NaCl gradient. NS3 containing fractions were pooled and concentrated on an Amicon stirred ultrafiltration cell using a YM-10 membrane. The enzyme was further purified on 26/60 Superdex 75 column (Pharmacia), equilibrated in buffer A. The sample was loaded at a flow rate 1 mL/min, the column was then washed with a buffer A at a flow rate 2 mL/min. Finally, the NS3 protease containing fractions were applied on Mono S 10/10 column (Pharmacia) equilibrated in 50 mM Tris.HCl buffer, pH 7.5, 10% glycerol and 1 mM DTT and operating at flow rate 2 mL/min. Enzyme was eluted by applying 20 column volumes of a linear 0.1–0.5 M NaCl gradient. Based on SDS-PAGE analysis as well as HPLC analysis and active site titration, the purity of the HCV NS3 1a protease was greater than 95%. The enzyme was stored at −70° C. and diluted just prior to use.

Enzyme Assays

Concentrations of protease were determined in the absence of NS4a by using the peptide ester substrate Ac-DED(Edans)EEAbuψ[COO]ASK(Dabcyl)-NH$_2$ (Taliani et al. *Anal. Biochem.* 240, 60–67, 1996.) and the inhibitor, H-Asp-Glu-Val-Val-Pro-boroAlg-OH (administered as Example Q9701 which hydrolyzes to the boronic acid), and by using tight binding reaction conditions (Bieth, *Methods Enzymol.* 248, 59–85, 1995). Best data was obtained for an enzyme level of 50 nM. Alternately, protease (63 μg/mL) was allowed to react with 3 μM NS4a, 0.10 mM Ac-Glu-Glu-Ala-Cys-pNA, and varying level of Q9701 (0–6 μM). Concentrations of protease were determined from linear plots of Activity vs.[Q9701]. Molar concentrations of proteases were determined from the x-intercept.

$K_m$ values were determined measuring the rate of hydrolysis of the ester substrate over a range of concentrations from 5.0 to 100 μM in the presence of 3 μM KKNS4a (KKGSVVIVGRIVLSGKPAIIPKK). Assay were run at 25° C., by incubating ~1 nM enzyme with NS4a for 5 min in 148 μl of buffer (50 mM Tri buffer, pH 7.0, 50% glycerol, 2% Chaps, and 5.0 mM DTT. Substrate (2.0 μl) in buffer was added and the reaction was allowed to proceed for 15 min. Reactions were quenched by adding 3.0 μL of 10% TFA, and the levels of hydrolysis were determined by HPLC. Aliquots (50 μL) were injected on the HPLC and linear gradients from 90% water, 10% acetonitrile and 0.10 % TFA to 10% water, 90% acetonitrile and 0.10% TFA were run at a flow rate of 1.0 mL/min over a period of 30 min. HPLCs were run on a HP1090 using a Rainin 4.6×250 mm C18 column (cat # 83-201-C) fluorescent detection using 350 and 500 nm as excitation and emission wavelengths, respectively. Levels of hydrolysis were determined by measuring the area of the fluorescent peak at 5.3 min. 100% hydrolysis of a 5.0 μM sample gave an area of 7.95±0.38 fluorescence units.). Kinetic constants were determined from the iterative fit of the Michaelis equation to the data. Results are consistent with data from Liveweaver Burk fits and data collected for the 12.8 min peak measured at 520 nm.

Enzyme activity was also measured by measuring the increase in fluorescence with time by exciting at 355 nm and measuring emission at 495 nm using a Perkin Elmer LS 50 spectrometer. A substrate level of 5.0 μM was used for all fluorogenic assays run on the spectrometer.

Inhibitor Evaluation In vitro

Inhibitor effectiveness was determined by measuring enzyme activity both in the presence and absence of inhibitor. Velocities were fit to the equation for competitive inhibition for individual reactions of inhibitors with the enzyme using $$v_i V_o = [Khd\ m\ (1+I/K_i)+S]/[K_m+S].$$

The ratio $v_i/v_o$ is equal to the ratio of the Michaelis equations for velocities measured in the presence ($v_i$) and absence ($v_o$) of inhibitor. Values of $v_i/v_o$ were measured over a range of inhibitor concentrations with the aid of an Excel™ Spreadsheet. Reported $K_i$ values are the average of 3–5 separate determinations. Under the conditions of this assay, the IC$_{50}$ and $K_i$s are comparable measures of inhibitor effectiveness.

Using the methodology described above, a number of compounds of the present invention were found to exhibit a $K_i$ of ≦60 μM, thereby confirming the utility of the compounds of the present invention as effective NS3 protease inhibitors.

Inhibitor Evaluation in Cell Assay.

The following method was devised to assess inhibitory action of test compounds on the HCV NS3 protease in cultured cells. Because it is not possible to efficiently infect cells with hepatitis C virus, an assay was developed based on co-expression in transfected cell lines of two plasmids, one is able to direct synthesis of the NS3 protease and the other to provide a polypeptide analogous to a part of the HCV non-structural protein containing a single known peptide sequence highly susceptible to cleavage by the protease.

When installed in cultured cells by one of a variety of standard methods, the substrate plasmid produces a stable polypeptide of approximately 50 KD, but when the plasmid coding for the viral protease is co-expressed, the enzymatic action of the protease hydrolyzes the substrate at a unique sequence between a cysteine and a serine pair, yielding products which can be detected by antibody-based technology, eg, a western blot. Quantitation of the amounts of precursor and products can be done by scanning film auto-radiograms of the blots or direct luminescense-based emissions from the blots in a commercial scanning device. The general organization of the two plasmids is provided in Scheme 6. The coding sequences for the NS3 protease and the substrate were taken from genotype 1a of HCV, but other genotypes, eg 2a, may be substituted with similar results.

The DNA plasmids are introduced into cultured cells using electroporation, liposomes or other means. Synthesis of the protease and the substrate begin shortly after introduction and may be detected within a few hours by immunological means. Therefore, test compounds are added at desired concentrations to the cells within a few minutes after introducing the plasmids. The cells are then placed in a standard $CO_2$ incubator at 37° C., in tissue culture medium eg Dulbecco-modified MEM containing 10% bovine serum. After 6–48 hours, the cells are collected by physically scraping them from plastic dishes in which they have been growing, centrifuging them and then lysing about $10^6$ of the concentrated cells in a minimal volume of buffered detergent, eg 20 μl of 1% sodium dodecyl sulfate in 0.10 M Tris-HCl, pH 6.5, containing 1% mercaptaethanol and 7% glycerol. The samples are then loaded onto a standard SDS polyacrylamide gel, the polypeptides separated by electrophoresis, and the gel contents then electroblotted onto nitrocellulose or other suitable paper support, and the substrate and products detected by decoration with specific antibodies.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

Example 09701

Preparation of H-Asp-Glu-Val-Val-Pro-boroAlg pinanediol ester·trifluoroacetate.

Preparation of Boc-Asp(OtBu)-Glu(OtBu)-Val-Val-Pro-OH.

Boc-Val-Pro-OBzl was prepared by dissolving H-Pro-OBzl (20 g, 83 mmol) in 50 mL of chloroform and adding Boc-Val-OH (18.0 g, 83 mmol), HOBt (23.0g, 165 mmol), NMM (9.0 mL, 83 mmol) and DCC (17.0 g, 83 mmol). The reaction mixture was stirred overnight at room temperature. The mixture was filtered and solvent was evaporated. Ethyl acetate was added and insoluble material was removed by filtration. The filtrate was washed with 0.2N HCl, 5% $NaHCO_3$, and saturated aqueous NaCl. It was dried over $Na_2SO_4$, filtered and evaporate to give a white solid (30 g, 75 mmol, 90%). ESI/MS calculated for $C_{22}H_{32}N_2O_5$ +H: 405.2. Found 405.6.

Boc-Val-Val-Pro-OBzl was prepared by dissolving Boc-Val-Pro-OBzl (14.0 g, 35.0 mmol) in 4N HCl in dioxane (20 mL) and allowing the reaction to stir for 2h under an inert atmosphere at room temperature. The reaction mixture was concentrated by evaporation in vacuo and ether was added to yield a precipitate. It was collected by filtration under nitrogen. After drying in vacuo with $P_2O_5$, H-Val-Pro-OBzl was obtained as a white solid (22.6 g, 30.3 mmol, 89%). (ESI/MS calculated for $C_{17}H_{24}N_2O_3$ +H: 305.2. Found: 305.2.) H-Val-Pro-OBzl (9.2 g, 27 mmol) was dissolved in 50 mL of $CH_2Cl_2$ and Boc-Val-OH (7.3 g, 27 mmol), HOBt (7.3 g, 54 mmol), NMM (3.0 mL, 27 mmol) and DCC (5.6 g, 27 mmol) were added. The reaction mixture stirred overnight at room temperature. The mixture was filtered and the filtrate was evaporated. The residue was dissolved in ethyl acetate and the solution was re-filtered. The filtrate was washed with 0.2N HCl, 5% $NaHCO_3$, and saturated aqueous NaCl. It was dried over $Na_2SO_4$, filtered and evaporated to give a yellow oil (10.6 g, 21.1 mmol, 78%). ESI/MS calculated for $C_{27}H_{41}N_3O_6$ +Na: 526.3 Found: 526.4.

Z-Glu(OtBu)-Val-Val-Pro-OBzl was also prepared by DCC coupling. H-Val-Val-Pro-OBzl·hydrochloride was obtained in a 100% yield by treating the corresponding Boc compound with anhydrous HCl using the procedure described for H-Val-Pro-OBzl (ESI/MS calculated for $C_{22}H_{33}N_3O_4$ +H: 404.2. Found 404.3.). The amine hydrochloride (7.40 g, 16.8 mmol) was dissolved in 185 mL DMF and 25 mL THF. Z-Glu(O$^t$Bu)-OH (5.60 g, 16.8 mmol), HOBt (4.60 g, 33.6 mmol), NMM (1.85 mL, 16.8 mmol) and DCC (3.5 g, 16.8 mmol) were added. The reaction was run and the product was isolated by the procedure described for Boc-Val-Val-Pro-OBzl. The tetrapeptide was obtained as a white foam (12.0 g, 16.1 mmol, 96%). ESI/MS calculated for $C_{39}H_{54}N_4O_9$ +Na: 745.4. Found: 745.4.

H-Glu(OtBu)-Val-Val-Pro-OH was prepared by dissolving Z-Glu(O$^t$Bu)-Val-Val-Pro-OBzl (2.90 g, 3.89 mmol) in 100 mL methanol containing 1% acetic acid. Pearlman's catalyst, Pd(OH)$_2$, (l00mg) was added and the flask was placed on the Parr hydrogenation apparatus with an initial $H_2$ pressure of 34 psi. After three hours, the catalyst was removed by filtration through a celite pad and the filtrate was evaporated in vacuo to yield a yellow oil (1.30 g, 2.61 mmol, 67%). ESI/MS calculated for $C_{24}H_{42}N_4O_7$ +H: 499.3 Found: 499.4.

Boc-Asp(OtBu)-Glu(OtBu)-Val-Val-Pro-OH was prepared by active ester coupling. Boc-Asp(OtBu)-N-hydroxysuccinimide ester was prepared by coupling Boc-Asp(OtBu)-OH (3.00 g, 10.4 mmol) to N-hydroxysuccinimide (1.19 g, 10.4 mmol) in 50 mL of ethylene glycol dimethyl ether. The reaction flask was placed in an ice bath at 0° C. and DCC was added. The reaction mixture was slowly allowed to warm to room temperature and to stir overnight. The mixture was filtered and the filtrate was evaporated in vacuo. The residue was dissolved in ethyl acetate and re-filtered. The filtrate was evaporated give a white solid. Recrystallized from ethyl acetate: hexane gave the activated ester (3.38 g, 8.80 mmol, 84%). (ESI/MS calculated for $C_{17}H_{26}N_2O_8$ +H: 387.2. Found: 387.4.) H-Glu(O$^t$Bu)-Val-Val-Pro-OH (5.40 g, 10.8 mmol) was dissolved in 100 mL of water. Sodium bicarbonate (0.92 g, 11.0 mmol) was added followed by triethylamine (2.30 mL, 16.5 mmol). The N-hydroxysuccinimide ester (3.84 g, 10.0 mmol) was dissolved in 100 mL dioxane and was added to the H-Glu(O$^t$Bu)-Val-Val-Pro-OH solution. The mixture stirred overnight at room temperature. Dioxane was removed in vacuo and 1.0 M HCl was added to give pH ~1. The product was extracted into ethyl acetate. The ethyl acetate solution was washed with 0.2 N HCl, dried over sodium sulfate, filtered, and evaporated to yield a yellow oil (7.7 g, 10.0 mmol, 100%). ESI/MS calculated for $C_{37}H_{63}N_5O_{12}$ +Na: 792.4. Found: 792.4.

Boc-Asp(OtBu)-Glu(OtBu)-Val-Val-Pro-boroAlg-pinanediol was prepared by coupling the protected pentapeptide to H-boroAlg-pinanediol. Boc-Asp(O$^t$Bu)-Glu(OtBu)-Val-Val-Pro-OH (1.8 g, 2.3 mmol) was dissolved 10 mL THF and was cooled to –20° C. Isobutyl chloroformate (0.30 mL, 2.3 mmol) and NMM (0.25 mL, 2.3 mmol) were added. After 5 minutes, this mixture was added to H-boroAlg-pinanediol (0.67 g, 2.3 mmol) dissolved in THF (8 mL) at –20° C. Cold THF (~5 mL) was used to aid in the transfer. Triethylamine (0.32 mL, 2.3 mmol) was added and the reaction mixture was allowed to come to room temperature and to stir overnight. The mixture was filtered and solvent was removed by evaporation. The residue was dissolved in ethyl acetate, washed with 0.2 N HCl, 5% NaHCO$_3$, and saturated NaCl. The organic phase was dried with Na$_2$SO$_4$, filtered, and evaporated to yield a yellow oil. Half of the crude product (1.5 g) was purified in 250 mg lots by HPLC using a 4 cm×30 cm Rainin C-18 reverse phase column. A gradient from 60: 40 acetonitrile: water to 100% acetonitrile was run over a period of 28 minutes at a flow rate of 40 mL/min. The fractions containing the desired product were pooled and lyophilized to yield a white solid (46 mg). $^1$H-NMR (CD$_3$OD) δ0.9–1.0 (m, 15H), 1.28 (s, 3H), 1.3 (s,3H), 1.44 (3s, 27H), 1.6–2.8 (20H), 3.7(m,1H), 3.9(m, 1H), 4.1–4.7 (7H), 5.05(m, 2H), 5.9(m, 1H). High res (ESI/MS) calculated for C$_{51}$H$_{86}$N$_6$O$_{13}$B$_1$ +H: 1001.635. Found 1001.633.

Preparation of Q9701: The hexapeptide analog, Boc-Asp(O$^t$Bu)-Glu(O$^t$Bu)-Val-Val-Pro-boroAlg-pinanediol, (22.5 mg, 0.023 mmol) was treated with 2 mL of TFA: CH$_2$Cl$_2$ (1: 1) for 2 h. The material was concentrated in vacuo and purified by HPLC using C-18 Vydac reverse phase (2.2×25 cm) column with a gradient starting at 60:40 acetonitrile/water with 0.1%TFA going to 95:5 over 25 minutes with a flow rate of 8 mL/min. The product eluted at 80% acetonitrile. The fractions were evaporated and dried under high vacuum to give 8.9 mg (49%) of the desired product as white amorphous solid. $^1$H-NMR (CD$_3$OD) δ 5.82 (m, 1H), 5.02 (m, 2H), 4.58(m, 1H), 4.42 (m, 3H), 4.18 (m, 4H), 3.90 (m, 1H), 3.62 (m, 1H), 3.01 (dd, 1H), 2.78 (m, 1H), 2.62 (m, 1H), 2.41–1.78 (m, 17H), 1.31 (s, 3H), 1.28 (s, 3H), 1.10–0.82 (m, 15H). ESI/MS calculated for C$_{38}$H$_{62}$N$_6$O$_{11}$B +H: 789.2. Found: 789.2.

What is claimed is:

1. A compound of Formula (I):

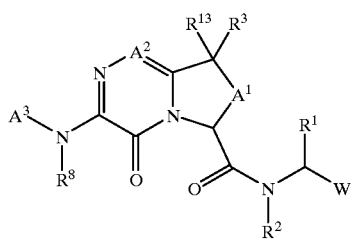

(I)

or a stereoisomer or pharmaceutically acceptable salt form thereof, wherein:

A$^1$ is —CH$_2$—, —CH$_2$CH$_2$—, or —CH$_2$CH$_2$CH$_2$—;
A$^2$ is —CR$^6$=;
A$^3$ is selected from —R$^9$, —A$^4$—R$^9$, —A$^4$—A$^5$—R$^9$, and —A$^4$—A$^5$—A$^6$—R$^9$;
W is selected from the group
—B(OR$^{26}$) (OR$^{27}$)
—C(=O)C(=O)—Q,
—C(=O)C(=O)NH—Q,
—C(=O)C(=O)—O—Q,
—C(=O)CF$_2$C(=O)NH—Q,
—C(=O)CF$_3$,
—C(=O)CF$_2$CF$_3$,
—C(=O)H,
an amino acid residue,
—A$^7$—A$^8$, and
—A$^7$—A$^8$—A$^9$;
Q is selected from —(CR$^{10}$R$^{10c}$)$_t$—Q$^1$, —(CR$^{10}$R$^{10c}$)$_t$—Q$^2$,
C$_1$–C$_4$ alkyl substituted with Q$^1$,
C$_2$–C$_4$ alkenyl substituted with Q$^1$,
C$_2$–C$_4$ alkynyl substituted with Q$^1$,
an amino acid residue,
—A$^7$—A$^8$, and
—A$^7$—A$^8$—A$^9$;
Q$^1$ is selected from
—CO$_2$R$^{11}$, —SO$_2$R$^{11}$, —SO$_3$R$^{11}$, —P(O)$_2$R$^{11}$, —P(O)$_3$R$^{11}$,
aryl substituted with 0–4 Q$^{1a}$,
5–6 membered heterocyclic group consisting of carbon atoms and 1–4 heteroatoms selected from the group: O, S, and N, said heterocyclic group substituted with 0–4 Q$^{1a}$;
Q$^{1a}$ is H, F, Cl, Br, I, —NO$_2$, —CN, —NCS, —CF$_3$, —OCF$_3$, —CH$_3$, —OCH$_3$, —CO$_2$R$^{19}$, —C(=O)NR$^{19}$R$^{19}$, —NHC(=O)R$^{19}$, —SO$_2$R$^{19}$, —SO$_2$NR$^{19}$R$^{19}$, —NR$^{19}$R$^{19}$, —OR$^{19}$, —SR$^{19}$,
C$_1$–C$_4$ alkyl, C$_1$–C$_4$ alkoxy, C$_1$–C$_4$ haloalkyl, C$_1$–C$_4$ haloalkoxy
alternatively, NR$^{19}$R$^{19}$ may form a 5–6 membered heterocyclic group consisting of carbon atoms, a nitrogen atom, and optionally a second heteroatom selected from the group: O, S, and N;
Q$^2$ is —X—NR$^{12}$—Z, —NR$^{12}$—Y—Z, or —X—NR$^{12}$—Y—Z;
X is selected from the group: —C(=O)—, —S—, —S(=O)—, —S(=O)$_2$—, —P(O)—, —P(O)$_2$—, and —P(O)$_3$—;
Y is selected from the group: —C(=O)—, —S—, —S(=O)—, —S(=O)$_2$—, —P(O)—, —P(O)$_2$—, and —P(O)$_3$—;
Z is C$_1$–C$_4$ haloalkyl,
C$_1$–C$_4$ alkyl substituted with 0–3 Z$^a$,
C$_2$–C$_4$ alkenyl substituted with 0–3 Z$^a$,
C$_2$–C$_4$ alkynyl substituted with 0–3 Z$^a$,
C$_3$–C$_{10}$ cycloalkyl substituted with 0–5 Z$^b$,
C$_3$–C$_{10}$ carbocycle substituted with 0–5 Z$^b$,
aryl substituted with 0–5 Z$^b$,
5–10 membered heterocyclic group consisting of carbon atoms and 1–4 heteroatoms selected from the group: O, S, and N, said heterocyclic group substituted with 0–4 Z$^b$;
an amino acid residue,
—A$^7$—A$^8$, or
—A$^7$—A$^8$—A$^9$;
Z$^a$ is H, F, Cl, Br, I, —NO$_2$, —CN, —NCS, —CF$_3$, —OCF$_3$, —CH$_3$, —OCH$_3$, —CO$_2$R$^{20}$, —C(=O)NR$^{20}$R$^{20}$, —NHC(=O)R$^{20}$, —NR$^{20}$R$^{20}$, —OR$^{20}$, —SR$^{20}$, —S(=O)R$^{20}$, —SO$_2$R$^{20}$, —SO$_2$NR$^{20}$R$^{20}$,
C$_1$–C$_4$ alkyl, C$_1$–C$_4$ alkoxy, C$_1$–C$_4$ haloalkyl, C$_1$–C$_4$ haloalkoxy,
C$_3$–C$_{10}$ cycloalkyl substituted with 0–5 Z$^b$,
C$_3$–C$_{10}$ carbocycle substituted with 0–5 Z$^b$,
aryl substituted with 0–5 Z$^b$, or
5–10 membered heterocyclic group consisting of carbon atoms and 1–4 heteroatoms selected from the group: O, S, and N, said heterocyclic group substituted with 0–4 Z$^b$;
Z$^b$ is H, F, Cl, Br, I, —NO$_2$, —CN, —NCS, —CF$_3$, —OCF$_3$, —CH$_3$, —OCH$_3$, —CO$_2$R$^{20}$, —C(=O)NR$^{20}$R$^{20}$, —NHC(=O)R$^{20}$, —NR$^{20}$R$^{20}$, —OR$^{20}$, —SR$^{20}$, —S(=O)R$^{20}$, —SO$_2$R$^{20}$, —SO$_2$NR$^{20}$R$^{20}$,
C$_1$–C$_4$ alkyl, C$_1$–C$_4$ alkoxy, C$_1$–C$_4$ haloalkyl, C$_1$–C$_4$ haloalkoxy, $C_3$–$C_{10}$ cycloalkyl substituted with 0–5 $Z^c$,
$C_3$–$C_{10}$ carbocycle substituted with 0–5 $Z^c$,
aryl substituted with 0–5 $Z^c$, or
5–10 membered heterocyclic group consisting of carbon atoms and 1–4 heteroatoms selected from the group: O, S, and N, said heterocyclic group substituted with 0–4 $Z^c$;

$Z^c$ is H, F, Cl, Br, I, —$NO_2$, —CN, —NCS, —$CF_3$, —$OCF_3$, —$CH_3$, —$OCH_3$, —$CO_2R^{20}$, —C(=O)$NR^{20}R^{20}$, —NHC(=O)$R^{20}$, —$NR^{20}R^{20}$, —$OR^{20}$, —$SR^{20}$, —S(=O)$R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl, $C_1$–$C_4$ haloalkoxy;

alternatively, $NR^{20}R^{20}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:
a) —OH,
b) —F,
c) —$NR^{28}R^{29}$,
d) $C_1$–$C_8$ alkoxy, or
when taken together, $OR^{26}$ and $OR^{27}$ form:
e) a cyclic boron ester where said chain or ring contains from 2 to 20 carbon atoms, and, optionally, 1, 2, or 3 heteroatoms which can be N, S, or O,
f) a cyclic boron amide where said chain or ring contains from 2 to 20 carbon atoms and, optionally, 1, 2, or 3 heteroatoms which can be N, S, or O,
g) a cyclic boron amide-ester where said chain or ring contains from 2 to 20 carbon atoms and, optionally, 1, 2, or 3 heteroatoms which can be N, S, or O;

$R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$,
aryl substituted with 0–5 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH, —$CO_2R^{1b}$, —$SO_2R^{1b}$, —$SO_3R^{1b}$, —P(O)$_2R^{1b}$, —P(O)$_3R^{1b}$, —C(=O)$NHR^{1b}$, —NHC(=O)$R^{1b}$, —$SO_2NHR^{1b}$, —$OR^{1b}$, —$SR^{1b}$,
$C_1$–$C_3$ alkyl, $C_3$–$C_6$ cycloalkyl, $C_1$–$C_6$ alkoxy, —S—($C_1$–$C_6$ alkyl),
aryl substituted with 0–5 $R^{1c}$,
—O—$(CH_2)_q$-aryl substituted with 0–5 $R^{1c}$,
—S—$(CH_2)_q$-aryl substituted with 0–5 $R^{1c}$,
5–10 membered heterocyclic group consisting of carbon atoms and 1–4 heteroatoms selected from the group: O, S, and N, and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocycle substituted with 0–5 $R^{1c}$,
aryl substituted with 0–5 $R^{1c}$,
5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:
$C_1$–$C_4$ alkyl, Cl, F, Br, I, OH, $C_1$–$C_4$ alkoxy, —CN, —$NO_2$, —$OR^{1d}$, —C(=O)$OR^{1d}$, —$NR^{1d}R^{1d}$, —$CF_3$, —$OCF_3$, and aryl substituted by 0–3 $R^{1e}$;

$R^{1d}$ is H, $C_1$–$C_4$ alkyl, phenyl or benzyl;
$R^{1e}$ is selected at each occurrence from the methyl, ethyl, Cl, F, Br, I, OH, methoxy, ethoxy, —CN, —$NO_2$, —C(=O)$OR^{1d}$, $NR^{1d}R^{1d}$, $CF_3$, and $OCF_3$;

$R^2$ is H, $C_1$–$C_4$ alkyl, $C_2$–$C_4$ alkenyl, $C_2$–$C_4$ alkynyl, or $C_3$–$C_4$ cycloalkyl;

$R^3$ is —$R^4$, —$NR^4R^5$, —$OR^4$, or —$SR^4$;

$R^4$ is selected from the group: H,
$C_1$–$C_8$ alkyl substituted with 0–3 $R^{4a}$,
$C_2$–$C_8$ alkenyl substituted with 0–3 $R^{4a}$,
$C_2$–$C_8$ alkynyl substituted with 0–3 $R^{4a}$,
$C_3$–$C_{10}$ cycloalkyl substituted with 0–4 $R^{4b}$,
aryl substituted with 0–5 $R^{4b}$,
5–10 membered heterocyclic group consisting: of carbon atoms and 1–4 heteroatoms selected from the group: O, S, and N, and said heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_3$–$C_{10}$ cycloalkyl substituted with 0–4 $R^{4b}$,
aryl substituted with 0–5 $R^{4b}$, and
5–10 membered heterocyclic group consisting of carbon atoms and 1–4 heteroatoms selected from the group: O, S, and N, and said heterocyclic group is substituted with 0–3 $R^{4b}$;

$R^{4b}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_1$–$C_6$ alkyl substituted with 0–3 $R^{4c}$,
$C_2$–$C_6$ alkenyl substituted with 0–3 $R^{4c}$,
$C_2$–$C_6$ alkynyl substituted with 0–3 $R^{4c}$,
$C_3$–$C_6$ cycloalkyl substituted with 0–4 $R^{4d}$,
aryl substituted with 0–5 $R^{4d}$, and
5–10 membered heterocyclic group consisting of carbon atoms and 1–4 heteroatoms selected from the group: O, S, and N, and said heterocyclic group is substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_3$–$C_6$ cycloalkyl substituted with 0–4 $R^{4d}$,
aryl substituted with 0–5 $R^{4d}$,
5–10 membered heterocyclic group consisting of carbon atoms and 1–4 heteroatoms selected from the group: O, S, and N, and said heterocyclic group is substituted with 0–3 $R^{4d}$;

$R^{4d}$ is, at each occurrence, independently selected from:
H, F, Cl, Br, I, —NO$_2$, —CN, —NCS, —CF$_3$, —OCF$_3$, —CH$_3$,
—OCH$_3$, =O, OH, —CO$_2$H, phenyl, —NH$_2$, —NH(CH$_3$), —N(CH$_3$)$_2$,
—CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11}$,
C$_1$–C$_4$ alkyl, C$_1$–C$_4$ alkoxy, C$_1$–C$_4$ haloalkyl, and C$_1$–C$_4$ haloalkoxy;

$R^5$ is selected from the group: H, C$_1$–C$_6$ alkyl, phenyl, phenylmethyl-, phenylethyl-, C$_3$–C$_6$ cycloalkyl, C$_3$–C$_6$ cycloalkylmethyl-, and C$_3$–C$_6$ cycloalkylethyl-;

$R^6$ is selected from the group: H, F, Cl, Br, I,
C$_1$–C$_6$ alkyl substituted with 0–3 $R^{6a}$,
C$_2$–C$_6$ alkenyl substituted with 0–3 $R^{6a}$,
C$_2$–C$_6$ alkynyl substituted with 0–3 $R^{6a}$,
C$_3$–C$_6$ cycloalkyl substituted with 0–4 $R^{6b}$,
aryl substituted with 0–5 $R^{6b}$,
5–6 membered heterocyclic group consisting of carbon atoms and 1–4 heteroatoms selected from the group: O, S, and N, and said heterocyclic group is substituted with 0–3 $R^{6b}$;

$R^{6a}$ is selected from the group: H, F, Cl, Br, I, —CO$_2$R$^{11}$, —NR$^{11}$R$^{11}$, —OR$^{11}$, —SR$^{11}$, —C(=NH)NH$_2$,
C$_3$–C$_6$ cycloalkyl substituted with 0–4 $R^{6b}$,
aryl substituted with 0–5 $R^{6b}$,
5–6 membered heterocyclic group consisting of carbon atoms and 1–4 heteroatoms selected from the group: O, S, and N, and said heterocyclic group is substituted with 0–3 $R^{6b}$;

$R^{6b}$ is selected from the group: H, F, Cl, Br, I, —CO$_2$R$^{11}$, —NR$^{11}$R$^{11}$, —OR$^{11}$, —SR$^{11}$, —C(=NH)NH$_2$;
C$_1$–C$_6$ alkyl substituted with 0–3 $R^{6c}$,
C$_2$–C$_6$ alkenyl substituted with 0–3 $R^{6c}$,
C$_2$–C$_6$ alkynyl substituted with 0–3 $R^{6c}$,
C$_3$–C$_6$ cycloalkyl substituted with 0–4 $R^{6d}$,
aryl substituted with 0–5 $R^{6d}$,
5–6 membered heterocyclic group consisting of carbon atoms and 1–4 heteroatoms selected from the group: O, S, and N, and said heterocyclic group is substituted with 0–3 $R^{6d}$;

$R^{6c}$ is selected from the group: H, F, Cl, Br, I, —CO$_2$R$^{11}$, —NR$^{11}$R$^{11}$, —OR$^{11}$, —SR$^{11}$, —C(=NH)NH$_2$,
C$_3$–C$_6$ cycloalkyl substituted with 0–4 $R^{6d}$,
aryl substituted with 0–5 $R^{6d}$,
5–6 membered heterocyclic group consisting of carbon atoms and 1–4 heteroatoms selected from the group: O, S, and N, and said heterocyclic group is substituted with 0–3 $R^{6d}$;

$R^{6d}$ is selected from the group: H, F, Cl, Br, I, —CO$_2$R$^{11}$, —NR$^{11}$R$^{11}$, —OR$^{11}$, —SR$^{11}$, —C(=NH)NH$_2$;

$R^8$ is H, C$_1$–C$_4$ alkyl, C$_2$–C$_4$ alkenyl, C$_2$–C$_4$ alkynyl, or C$_3$–C$_4$ cycloalkyl;

$R^9$ is selected from the group: —S(=O)R$^{9a}$, —S(=O)$_2$R$^{9a}$, —C(=O)R$^{9a}$, —C(=O)OR$^{9a}$, —C(=O)NHR$^{9a}$, C$_1$–C$_3$ alkyl-R$^{9a}$, C$_2$–C$_6$ alkenyl-R$^{9a}$, and C$_2$–C$_6$ alkynyl-R$^{9a}$;

$R^{9a}$ is selected from the group: H
C$_1$–C$_6$ alkyl substituted with 0–3 $R^{9b}$,
C$_3$–C$_6$ cycloalkyl substituted with 0–3 $R^{9c}$ and
aryl substituted with 0–3 $R^{9c}$ and
5–14 membered heterocyclic group consisting of carbon atoms and 1–4 heteroatoms selected from the group: O, S, and N; and said heterocyclic group is substituted with 0–3 $R^{9c}$;

$R^{9b}$ is selected from the group:
phenyl substituted with 0–3 $R^{9c}$,
naphthyl substituted with 0–3 $R^{9c}$,
benzyl substituted with 0–3 $R^{9c}$, and
5–10 membered heterocyclic group consisting of carbon atoms and 1–4 heteroatoms selected from the group: O, S, and N; and said heterocyclic group is substituted with 0–3 $R^{9c}$;

$R^{9c}$ is selected at each occurrence from the group:
H, F, Cl, Br, I, —NO$_2$, —CN, —NCS, —CF$_3$, —OCF$_3$, —CH$_3$,
—OCH$_3$, =O, OH, —CO$_2$H, phenyl, —NH$_2$, —NH(CH$_3$), —N(CH$_3$)$_2$,
—CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11}$,
C$_1$–C$_4$ haloalkyl, C$_1$–C$_4$ haloalkoxy,
C$_1$–C$_4$ alkyl substituted with 0–3 $R^{9d}$,
C$_1$–C$_4$ alkoxy substituted with 0–3 $R^{9d}$,
C$_3$–C$_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
H, F, Cl, Br, I, —NO$_2$, —CN, —NCS, —CF$_3$, —OCF$_3$, —CH$_3$,
—OCH$_3$, =O, OH, —CO$_2$H, phenyl, —NH$_2$, —NH(CH$_3$), —N(CH$_3$)$_2$,
—CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11}$,
C$_1$–C$_4$ alkyl, C$_1$–C$_4$ alkoxy, C$_1$–C$_4$ haloalkyl, and C$_1$–C$_4$ haloalkoxy;

$R^{10}$ is selected from the group: —CO$_2$R$^{11}$, —NR$^{11}$R$^{11}$, and C$_1$–C$_6$ alkyl substituted with 0–1 $R^{10a}$;

$R^{10a}$ is selected from the group: halo, —NO$_2$, —CN, —CF$_3$, —CO$_2$R$^{11}$, —NR$^{11}$R$^{11}$, —OR$^{11}$, —SR$^{11}$, —C(=NH)NH$_2$, and aryl substituted with 0–1 R$_{10b}$;

$R^{10b}$ is selected from the group: —CO$_2$H, —NH$_2$, —OH, —SH, and —C(=NH)NH$_2$;

$R^{10c}$ is H or C$_1$–C$_4$ alkyl;

alternatively, $R^{10}$ and $R^{10c}$ can be combined to form a C$_3$–C$_6$ cycloalkyl group substituted with 0–1 $R^{10a}$;

$R^{11}$ is, at each occurrence, independently H or C$_1$–C$_4$ alkyl;

$R^{11a}$ is, at each occurrence, independently H, C$_1$–C$_4$ alkyl, aryl, or C$_1$–C$_4$ haloalkyl;

$R^{12}$ is H or C$_1$–C$_4$ alkyl;

$R^{13}$ is H or C$_1$–C$_4$ alkyl;

$R^{19}$ is C$_1$–C$_4$ alkyl, C$_1$–C$_4$ haloalkyl, aryl, aryl(C$_1$–C$_4$ alkyl), C$_3$–C$_6$ cycloalkyl, or C$_3$–C$_6$ cycloalkyl(C$_1$–C$_4$ alkyl);

$R^{20}$ is H, C$_1$–C$_4$ alkyl, C$_1$–C$_4$ haloalkyl, aryl, aryl(C$_1$–C$_4$ alkyl)-, C$_3$–C$_6$ cycloalkyl, or C$_3$–C$_6$ cycloalkyl(C$_1$–C$_4$ alkyl)-;

$R^{28}$ and $R^{29}$, are independently selected from: H, C$_1$–C$_4$ alkyl, aryl(C$_1$–C$_4$ alkyl)-, and C$_3$–C$_7$ cycloalkyl;

$A^4$, $A^5$, $A^6$, $A^7$, $A^8$, and $A^9$ are independently selected from an amino acid residue;

an amino acid residue, at each occurence, independently comprises a natural amino acid, a modified amino acid or an unnatural amino acid wherein said natural, modified or unnatural amino acid is of either D or L configuration;

t is 1, 2, 3, or 4; and q is 0, 1 or 2.

2. A compound according to claim 1 of Formula (Ia):

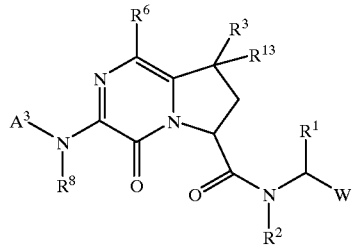

(Ia)

or a stereoisomer or pharmaceutically acceptable salt form thereof, wherein:

$A^3$ is selected from $-R^9$, $-A^4-R^9$, and $-A^4-A^5-R^9$;

W is selected from the group
- $-B(OR^{26})(OR^{27})$
- $-C(=O)C(=O)-Q$,
- $-C(=O)C(=O)NH-Q$,
- $-C(=O)C(=O)-O-Q$,
- $-C(=O)CF_2C(=O)NH-Q$,
- $-C(=O)CF_3$,
- $-C(=O)CF_2CF_3$,
- $-C(=O)H$,
- an amino acid residue,
- $-A^7-A^8$, and
- $-A^7-A^8-A^9$;

Q is selected from $-(CR^{10}R^{10c})_t-Q^1$, $-(CR^{10}R^{10c})_t-Q^2$,
- $C_1-C_4$ alkyl substituted with $Q^1$,
- $C_2-C_4$ alkenyl substituted with $Q^1$,
- $C_2-C_4$ alkynyl substituted with $Q^1$,
- an amino acid residue,
- $-A^7-A^8$, and
- $-A^7-A^8-A^9$;

$Q^1$ is selected from
- $-CO_2R^{11}$, $-SO_2R^{11}$, $-SO_3R^{11}$, $-P(O)_2R^{11}$, $-P(O)_3R^{11}$,
- aryl substituted with 0–4 $Q^{1a}$,
- 5–6 membered heterocyclic group consisting of carbon atoms and 1–4 heteroatoms selected from the group: O, S, and N, said heterocyclic group substituted with 0–4 $Q^{1a}$;

$Q^{1a}$ is H, F, Cl, Br, I, $-NO_2$, $-CN$, $-NCS$, $-CF_3$, $-OCF_3$, $-CH_3$, $-OCH_3$, $-CO_2R^{19}$, $-C(=O)NR^{19}R^{19}$, $-NHC(=O)R^{19}$, $-SO_2R^{19}$, $-SO_2NR^{19}R^{19}$, $-NR^{19}R^{19}$, $-OR^{19}$, $-SR^{19}$,
- $C_1-C_4$ alkyl, $C_1-C_4$ alkoxy, $C_1-C_4$ haloalkyl, $C_1-C_4$ haloalkoxy alternatively, $NR^{19}R^{19}$ may form a 5–6 membered heterocyclic group consisting of carbon atoms, a nitrogen atom, and optionally a second heteroatom selected from the group: O, S, and N;

$Q^2$ is $-X-NR^{12}-Z$, $-NR^{12}-Y-Z$, or $-X-NR^{12}-Y-Z$;

X is selected from the group: $-C(=O)-$, $-S-$, $-S(=O)-$, $-S(=O)_2-$, $-P(O)-$, $-P(O)_2-$, and $-P(O)_3-$;

Y is selected from the group: $-C(=O)-$, $-S-$, $-S(=O)-$, $-S(=O)_2-$, $-P(O)-$, $-P(O)_2-$, and $-P(O)_3-$;

Z is $C_1-C_4$ haloalkyl,
- $C_1-C_4$ alkyl substituted with 0–3 $Z^a$,
- $C_2-C_4$ alkenyl substituted with 0–3 $Z^a$,
- $C_2-C_4$ alkynyl substituted with 0–3 $Z^a$,
- $C_3-C_{10}$ cycloalkyl substituted with 0–5 $Z^b$,
- $C_3-C_{10}$ carbocycle substituted with 0–5 $Z^b$,
- aryl substituted with 0–5 $Z^b$,
- 5–10 membered heterocyclic group consisting of carbon atoms and 1–4 heteroatoms selected from the group: O, S, and N, said heterocyclic group substituted with 0–4 $Z^b$;
- an amino acid residue,
- $-A^7-A^8$, or
- $-A^7-A^8-A^9$;

$Z^a$ is H, F, Cl, Br, I, $-NO_2$, $-CN$, $-NCS$, $-CF_3$, $-OCF_3$, $-CH_3$, $-OCH_3$, $-CO_2R^{20}$, $-C(=O)NR^{20}R^{20}$, $-NHC(=O)R^{20}$, $-NR^{20}R^{20}$, $-OR^{20}$, $-SR^{20}$, $-S(=O)R^{20}$, $-SO_2R^{20}$, $-SO_2NR^{20}R^{20}$,
- $C_1-C_4$ alkyl, $C_1-C_4$ alkoxy, $C_1-C_4$ haloalkyl, $C_1-C_4$ haloalkoxy,
- $C_3-C_{10}$ cycloalkyl substituted with 0–5 $Z^b$,
- $C_3-C_{10}$ carbocycle substituted with 0–5 $Z^b$,
- aryl substituted with 0–5 $Z^b$, or
- 5–10 membered heterocyclic group consisting of carbon atoms and 1–4 heteroatoms selected from the group: O, S, and N, said heterocyclic group substituted with 0–4 $Z^b$;

$Z^b$ is H, F, Cl, Br, I, $-NO_2$, $-CN$, $-NCS$, $-CF_3$, $-OCF_3$, $-CH_3$, $-OCH_3$, $-CO_2R^{20}$, $-C(=O)NR^{20}R^{20}$, $-NHC(=)R^{20}$, $-NR^{20}R^{20}$, $-OR^{20}$, $-SR^{20}$, $-S(=O)R^{20}$, $-SO_2R^{20}$, $-SO_2NR^{20}R^{20}$,
- $C_1-C_4$ alkyl, $C_1-C_4$ alkoxy, $C_1-C_4$ haloalkyl, $C_1-C_4$ haloalkoxy,
- $C_3-C_{10}$ cycloalkyl substituted with 0–5 $Z^c$,
- $C_3-C_{10}$ carbocycle substituted with 0–5 $Z^c$,
- aryl substituted with 0–5 $Z^c$, or
- 5–10 membered heterocyclic group consisting of carbon atoms and 1–4 heteroatoms selected from the group: O, S, and N, said heterocyclic group substituted with 0–4 $Z^c$;

$Z^c$ is H, F, Cl, Br, I, $-NO_2$, $-CN$, $-NCS$, $-CF_3$, $-OCF_3$, $-CH_3$, $-OCH_3$, $-CO_2R^{20}$, $-C(=O)NR^{20}R^{20}$, $-NHC(=O)R^{20}$, $-NR^{20}R^{20}$, $-OR^{20}$, $-SR^{20}$, $-S(=O)R^{20}$, $-SO_2R^{20}$, $-SO_2NR^{20}R^{20}$,
- $C_1-C_4$ alkyl, $C_1-C_4$ alkoxy, $C_1-C_4$ haloalkyl, $C_1-C_4$ haloalkoxy;

alternatively, $NR^{20}R^{20}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:
a) $-OH$,
b) $-F$,
c) $-NR^{28}R^{29}$,
d) $C_1-C_8$ alkoxy, or
when taken together, $OR^{26}$ and $OR^{27}$ form:
e) a cyclic boron ester where said chain or ring contains from 2 to 20 carbon atoms, and, optionally, 1, 2, or 3 heteroatoms which can be N, S, or O,
f) a cyclic boron amide where said chain or ring contains from 2 to 20 carbon atoms and, optionally, 1, 2, or 3 heteroatoms which can be N, S, or O, g) a cyclic boron amide-ester where said chain or ring contains from 2 to 20 carbon atoms and, optionally, 1, 2, or 3 heteroatoms which can be N, S, or O;

$R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$,
aryl substituted with 0–5 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH, —$CO_2R^{1b}$, —$SO_2R^{1b}$, —$SO_3R^{1b}$, —$P(O)_2R^{1b}$, —$P(O)_3R^{1b}$, —C(=O)NHR$^{1b}$, —NHC(=O)R$^{1b}$, —$SO_2$NHR$^{1b}$, —OR$^{1b}$, —SR$^{1b}$,
$C_1$–$C_3$ alkyl, $C_3$–$C_6$ cycloalkyl, $C_1$–$C_6$ alkoxy, —S—($C_1$–$C_6$ alkyl),
aryl substituted with 0–5 $R^{1c}$,
—O—$(CH_2)_q$-aryl substituted with 0–5 $R^{1c}$,
—S—$(CH_2)_q$-aryl substituted with 0–5 $R^{1c}$,
5–10 membered heterocyclic group consisting of carbon atoms and 1–4 heteroatoms selected from the group: O, S, and N, and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocycle substituted with 0–5 $R^{1c}$,
aryl substituted with 0–5 $R^{1c}$,
5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:
$C_1$–$C_4$ alkyl, Cl, F, Br, I, OH, $C_1$–$C_4$ alkoxy, —CN, —$NO_2$, —OR$^{1d}$, —C(=O)OR$^{1d}$, NR$^{1d}$R$^{1d}$, $CF_3$, $OCF_3$, and aryl substituted by 0–3 $R^{1e}$;

$R^{1d}$ is H, methyl, ethyl, propyl, butyl, phenyl, or benzyl;

$R^{1e}$ is selected at each occurrence from the methyl, ethyl, Cl, F, Br, I, OH, methoxy, ethoxy, —CN, —$NO_2$, —C(=O)OR$^{1d}$, NR$^{1d}$R$^{1d}$, $CF_3$, and $OCF_3$;

$R^2$ is H, methyl, ethyl, propyl, butyl, or cyclopropyl;

$R^3$ is —$R^4$, —NR$^4$R$^5$, —OR$^4$, or —SR$^4$;

$R^4$ is selected from the group: H,
$C_1$–$C_8$ alkyl substituted with 0–3 $R^{4a}$,
$C_2$–$C_8$ alkenyl substituted with 0–3 $R^{4a}$,
$C_2$–$C_8$ alkynyl substituted with 0–3 $R^{4a}$,
$C_3$–$C_{10}$ cycloalkyl substituted with 0–4 $R^{4b}$,
aryl substituted with 0–5 $R^{4b}$,
5–10 membered heterocyclic group consisting of carbon atoms and 1–4 heteroatoms selected from the group: O, S, and N, and said heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)NR$^{11}$R$^{11}$, —NHC(=O)R$^{11}$, —NR$^{11}$R$^{11}$, OR$^{11a}$, —SR$^{11a}$, —C(=O)R$^{11a}$, —S(=O)R$^{11a}$, —$SO_2R^{11}$, —$SO_2NR^{11}R^{11}$,
$C_1$–$C_4$ haloalkyl, $C_1$–$C_4$ haloalkoxy,
$C_3$–$C_{10}$ cycloalkyl substituted with 0–4 $R^{4b}$,
aryl substituted with 0–5 $R^{4b}$, and
5–10 membered heterocyclic group consisting of carbon atoms and 1–4 heteroatoms selected from the group: O, S, and N, and said heterocyclic group is substituted with 0–3 $R^{4b}$;

$R^{4b}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)NR$^{11}$R$^{11}$, —NHC(=O)R$^{11}$, —NR$^{11}$R$^{11}$, OR$^{11a}$, —SR$^{11a}$, —C(=O)R$^{11a}$, —S(=O)R$^{11a}$, —$SO_2R^{11}$, —$SO_2NR^{11}R^{11}$,
$C_1$–$C_4$ haloalkyl, $C_1$–$C_4$ haloalkoxy,
$C_1$–$C_6$ alkyl substituted with 0–3 $R^{4c}$,
$C_2$–$C_6$ alkenyl substituted with 0–3 $R^{4c}$,
$C_2$–$C_6$ alkynyl substituted with 0–3 $R^{4c}$,
$C_3$–$C_6$ cycloalkyl substituted with 0–4 $R^{4d}$,
aryl substituted with 0–5 $R^{4d}$, and
5–10 membered heterocyclic group consisting of carbon atoms and 1–4 heteroatoms selected from the group: O, S, and N, and said heterocyclic group is substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)NR$^{11}$R$^{11}$, —NHC(=O)R$^{11}$, —NR$^{11}$R$^{11}$, —OR$^{11a}$, —SR$^{11a}$, C(=O)R$^{11a}$, —S(=O)R$^{11a}$, —$SO_2R^{11}$, —$SO_2NR^{11}R^{11}$,
$C_1$–$C_4$ haloalkyl, $C_1$–$C_4$ haloalkoxy,
$C_3$–$C_6$ cycloalkyl substituted with 0–4 $R^{4d}$,
aryl substituted with 0–5 $R^{4d}$,
5–10 membered heterocyclic group consisting of carbon atoms and 1–4 heteroatoms selected from the group: O, S, and N, and said heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —N($CH_3$)$_2$,
—$CO_2R^{11}$, —C(=O)NR$^{11}$R$^{11}$, —NHC(=O)R$^{11}$, —NR$^{11}$R$^{11}$, OR$^{11a}$, —SR$^{11a}$, —C(=O)R$^{11a}$, —S(=O)R$^{11a}$, —$SO_2R^{11}$, —$SO_2NR^{11}R^{11}$,
$C_1$–$C_4$ alkyl, $C_1$–$C_4$ alkoxy, $C_1$–$C_4$ haloalkyl, and $C_1$–$C_4$ haloalkoxy;

$R^5$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^6$ is H, Cl, Br, methyl, ethyl, or cyclopropyl;

$R^8$ is H, methyl, ethyl, propyl, butyl, or cyclopropyl;

$R^9$ is selected from the group: —S(=O)R$^{9a}$, —S(=O)$_2$R$^{9a}$, —C(=O)R$^{9a}$, —C(=O)OR$^{9a}$, —C(=O)NHR$^{9a}$, $C_1$–$C_3$ alkyl-R$^{9a}$, $C_2$–$C_6$ alkenyl-R$^{9a}$, and $C_2$–$C_6$ alkynyl-R$^{9a}$;

$R^{9a}$ is selected from the group: H
$C_1$–$C_6$ alkyl substituted with 0–3 $R^{9b}$,
$C_3$–$C_6$ cycloalkyl substituted with 0–3 $R^{9c}$ and
aryl substituted with 0–3 $R^{9c}$ and
5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group:
phenyl substituted with 0–3 $R^{9c}$,
naphthyl substituted with 0–3 $R^{9c}$,
benzyl substituted with 0–3 $R^{9c}$, and 5–10 membered heterocyclic group consisting of carbon atoms and 1–4 heteroatoms selected from the group: O, S, and N; and said heterocyclic group is substituted with 0–3 $R^{9c}$;

$R^{9c}$ is selected at each occurrence from the group:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, $OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_1$–$C_4$ alkyl substituted with 0–3 $R^{9d}$,
$C_1$–$C_4$ alkoxy substituted with 0–3 $R^{9d}$,
$C_3$–$C_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, $OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ alkyl, $C_1$–$C_4$ alkoxy, $C_1$–$C_4$ haloalkyl, and $C_1$–$C_4$ haloalkoxy;

$R^{10}$ is selected from the group: —$CO_2R^{11}$, —$NR^{11}R^{11}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, —$NR^{11}R^{11}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ is, at each occurrence, independently H or $C_1$–$C_4$ alkyl;

$R^{11a}$ is, at each occurrence, independently H, $C_1$–$C_4$ alkyl, aryl, or $C_1$–$C_4$ haloalkyl;

$R^{12}$ is H or $C_1$–$C_4$ alkyl;

$R^{13}$ is H, methyl, ethyl, propyl, or butyl;

$A^4, A^5, A^7, A^8$, and $A^9$ are independently selected from an amino acid residue;

an amino acid residue, at each occurence, independently comprises a natural amino acid, a modified amino acid or an unnatural amino acid wherein said natural, modified or unnatural amino acid is of either D or L configuration;

$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl);

$R^{20}$ is H, $C_1$–$C_4$ alkyl, $C_1$–$C_4$ haloalkyl, aryl, aryl($C_1$–$C_4$ alkyl)-, $C_3$–$C_6$ cycloalkyl, or $C_3$–$C_6$ cycloalkyl($C_1$–$C_4$ alkyl)-;

$R^{28}$ and $R^{29}$, are independently selected from: H, $C_1$–$C_4$ alkyl, aryl($C_1$–$C_4$ alkyl)-, and $C_3$–$C_7$ cycloalkyl;

t is 1, 2, or 3; and q is 0, 1 or 2.

3. A compound according to claim 2 of Formula (Ia):
$A^3$ is selected from —$R^9$, —$A^4$—$R^9$, and —$A^4$—$A^5$—$R^9$; and W is —B($OR^{26}$)($OR^{27}$), —C(=O)C(=O)NH—Q, —C(=O)$CF_2$C(=O)NH—Q, —C(=O)$CF_3$, —C(=O)H, or an amino acid residue.

4. A compound according to claim 3 of Formula (II):

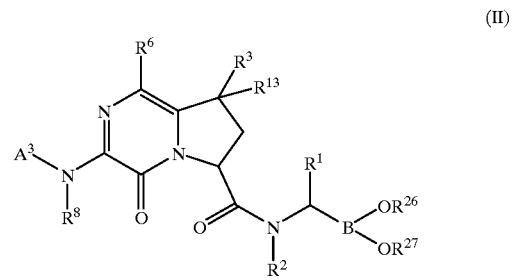

(II)

or a stereoisomer or pharmaceutically acceptable salt form thereof, wherein:

$A^3$ is selected from —$R^9$, —$A^4$—$R^9$, and —$A^4$—$A^5$—$R^9$;

$OR^{26}$ and $OR^{27}$ are independently selected from:
a) —OH,
b) —F,
c) —$NR^{28}R^{29}$,
d) $C_1$–$C_8$ alkoxy, or
when taken together, $OR^{26}$ and $OR^{27}$ form:
e) a cyclic boron ester where said chain or ring contains from 2 to 20 carbon atoms, and, optionally, 1, 2, or 3 heteroatoms which can be N, S, or O,
f) a cyclic boron amide where said chain or ring contains from 2 to 20 carbon atoms and, optionally, 1, 2, or 3 heteroatoms which can be N, S, or O,
g) a cyclic boron amide-ester where said chain or ring contains from 2 to 20 carbon atoms and, optionally, 1, 2, or 3 heteroatoms which can be N, S, or O;

$R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$,
aryl substituted with 0–5 $R^{1a}$, and
$C_3$–$C_6$ cycloalkyl substituted with 0–3 $R^{1a}$,;

$R^{1a}$ is selected at each occurrence from the group:
Cl, F, Br, I, $CF_3$, $CHF_2$, OH, =O, SH,
—$CO_2R^{1b}$, —$SO_2R^{1b}$, —$SO_3R^{1b}$, —P(O)$_2R^{1b}$, —P(O)$_3R^{1b}$, —C(=O)$NHR^{1b}$, —NHC(=O)$R^{1b}$, —$SO_2NHR^{1b}$, —$OR^{1b}$, —$SR^{1b}$,
$C_1$–$C_3$ alkyl, $C_3$–$C_6$ cycloalkyl, $C_1$–$C_6$ alkoxy,
—S—($C_1$–$C_6$ alkyl),
aryl substituted with 0–5 $R^{1c}$,
—O—($CH_2$)$_q$-aryl substituted with 0–5 $R^{1c}$,
—S—($CH_2$)$_q$-aryl substituted with 0–5 $R^{1c}$,
5–10 membered heterocyclic group consisting of carbon atoms and 1–4 heteroatoms selected from the group: O, S, and N, and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocycle substituted with 0–5 $R^{1c}$,
aryl substituted with 0–5 $R^{1c}$,
5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:
   $C_1$–$C_4$ alkyl, Cl, F, Br, I, OH, $C_1$–$C_4$ alkoxy, —CN, —NO$_2$, —OR$^{1d}$, —C(=O)OR$^{1d}$, NR$^{1d}$R$^{1d}$, CF$_3$, OCF$_3$, and aryl substituted by 0–3 R$^{1e}$;

$R^{1d}$ is H, methyl, ethyl, propyl, butyl, phenyl, or benzyl;

$R^{1e}$ is selected at each occurrence from the methyl, ethyl, Cl, F, Br, I, OH, methoxy, ethoxy, —CN, —NO$_2$, —C(=O)OR$^{1d}$, NR$^{1d}$R$^{1d}$, CF$_3$, and OCF$_3$;

$R^2$ is H, methyl, ethyl, propyl, butyl, or cyclopropyl;

$R^3$ is —R$^4$, —NR$^4$R$^5$, —OR$^4$, or —SR$^4$;

$R^4$ is selected from the group: H,
   $C_1$–$C_8$ alkyl substituted with 0–3 R$^{4a}$,
   $C_2$–$C_8$ alkenyl substituted with 0–3 R$^{4a}$,
   $C_2$–$C_8$ alkynyl substituted with 0–3 R$^{4a}$,
   $C_3$–$C_{10}$ cycloalkyl substituted with 0–4 R$^{4b}$,
   aryl substituted with 0–5 R$^{4b}$,
   5–10 membered heterocyclic group consisting of carbon atoms and 1–4 heteroatoms selected from the group: O, S, and N, and said heterocyclic group is substituted with 0–3 R$^{4b}$;

$R^{4a}$ is, at each occurrence, independently selected from:
   H, F, Cl, Br, I, —NO$_2$, —CN, —NCS, —CF$_3$, —OCF$_3$, —CH$_3$,
   —OCH$_3$, =O, OH, —CO$_2$H, phenyl, —C(=NH)NH$_2$, —NH$_2$, —NH(CH$_3$), —N(CH$_3$)$_2$,
   —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$,
   —S(=O)R$^{11a}$, —SO$_2$R$^{11}$, —SO$_2$NR$^{11}$R$^{11}$,
   $C_1$–$C_4$ haloalkyl, $C_1$–$C_4$ haloalkoxy,
   $C_3$–$C_{10}$ cycloalkyl substituted with 0–4 R$^{4b}$,
   aryl substituted with 0–5 R$^{4b}$, and
   5–10 membered heterocyclic group consisting of carbon atoms and 1–4 heteroatoms selected from the group: O, S, and N, and said heterocyclic group is substituted with 0–3 R$^{4b}$;

$R^{4b}$ is, at each occurrence, independently selected from:
   H, F, Cl, Br, I, —NO$_2$, —CN, —NCS, —CF$_3$, —OCF$_3$, —CH$_3$,
   —OCH$_3$, =O, OH, —CO$_2$H, phenyl, —C(=NH)NH$_2$, —NH$_2$, —NH(CH$_3$), —N(CH$_3$)$_2$,
   —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$,
   —S(=O)R$^{11a}$, —SO$_2$R$^{11}$, —SO$_2$NR$^{11}$R$^{11}$,
   $C_1$–$C_4$ haloalkyl, $C_1$–$C_4$ haloalkoxy,
   $C_1$–$C_6$ alkyl substituted with 0–3 R$^{4c}$,
   $C_2$–$C_6$ alkenyl substituted with 0–3 R$^{4c}$,
   $C_2$–$C_6$ alkynyl substituted with 0–3 R$^{4c}$,
   $C_3$–$C_6$ cycloalkyl substituted with 0–4 R$^{4d}$,
   aryl substituted with 0–5 R$^{4d}$, and
   5–10 membered heterocyclic group consisting of carbon atoms and 1–4 heteroatoms selected from the group: O, S, and N, and said heterocyclic group is substituted with 0–3 R$^{4d}$;

$R^{4c}$ is, at each occurrence, independently selected from:
   H, F, Cl, Br, I, —NO$_2$, —CN, —NCS, —CF$_3$, —OCF$_3$, —CH$_3$,
   —OCH$_3$, =O, OH, —CO$_2$H, phenyl, —C(=NH)NH$_2$, —NH$_2$, —NH(CH$_3$), —N(CH$_3$)$_2$,
   —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$,
   —S(=O)R$^{11a}$, —SO$_2$R$^{11}$, —SO$_2$NR$^{11}$R$^{11}$,
   $C_1$–$C_4$ haloalkyl, $C_1$–$C_4$ haloalkoxy,
   $C_3$–$C_6$ cycloalkyl substituted with 0–4 R$^{4d}$,
   aryl substituted with 0–5 R$^{4d}$,
   5–10 membered heterocyclic group consisting of carbon atoms and 1–4 heteroatoms selected from the group: O, S, and N, and said heterocyclic group is substituted with 0–3 R$^{4d}$;

$R^{4d}$ is, at each occurrence, independently selected from:
   H, F, Cl, Br, I, —NO$_2$, —CN, —NCS, —CF$_3$, —OCF$_3$, —CH$_3$,
   —OCH$_3$, =O, OH, —CO$_2$H, phenyl, —NH$_2$, —NH(CH$_3$), —N(CH$_3$)$_2$,
   —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$,
   —S(=O)R$^{11a}$, —SO$_2$R$^{11}$, —SO$_2$NR$^{11}$R$^{11}$,
   $C_1$–$C_4$ alkyl, $C_1$–$C_4$ alkoxy, $C_1$–$C_4$ haloalkyl, and $C_1$–$C_4$ haloalkoxy;

$R^5$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^6$ is H, Cl, Br, methyl, ethyl, or cyclopropyl;

$R^8$ is H, methyl, ethyl, propyl, butyl, or cyclopropyl;

$R^9$ is selected from the group: —S(=O)R$^{9a}$, —S(=O)$_2$R$^{9a}$, —C(=O)R$^{9a}$, —C(=O)OR$^{9a}$, —C(=O)NHR$^{9a}$, $C_1$–$C_3$ alkyl-R$^{9a}$, $C_2$–$C_6$ alkenyl-R$^{9a}$, and $C_2$–$C_6$ alkynyl-R$^{9a}$;

$R^{9a}$ is selected from the group: H
   $C_1$–$C_6$ alkyl substituted with 0–3 R$^{9b}$,
   $C_3$–$C_6$ cycloalkyl substituted with 0–3 R$^{9c}$ and
   aryl substituted with 0–3 R$^{9c}$ and
   5–14 membered heterocyclic group consisting of carbon atoms and 1–4 heteroatoms selected from the group: O, S, and N, and said heterocyclic group is substituted with 0–3 R$^{9c}$;

$R^{9b}$ is selected from the group:
   phenyl substituted with 0–3 R$^{9c}$,
   naphthyl substituted with 0–3 R$^{9c}$,
   benzyl substituted with 0–3 R$^{9c}$, and
   5–10 membered heterocyclic group consisting of carbon atoms and 1–4 heteroatoms selected from the group: O, S, and N; and said heterocyclic group is substituted with 0–3 R$^{9c}$;

$R^{9c}$ is selected at each occurrence from the group:
   H, F, Cl, Br, I, —NO$_2$, —CN, —NCS, —CF$_3$, —OCF$_3$, —CH$_3$,
   —OCH$_3$, =O, OH, —CO$_2$H, phenyl, —NH$_2$, —NH(CH$_3$), —N(CH$_3$)$_2$,
   —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$,
   —S(=O)R$^{11a}$, —SO$_2$R$^{11}$, —SO$_2$NR$^{11}$R$^{11}$,
   $C_1$–$C_4$ haloalkyl, $C_1$–$C_4$ haloalkoxy,
   $C_1$–$C_4$ alkyl substituted with 0–3 R$^{9d}$,
   $C_1$–$C_4$ alkoxy substituted with 0–3 R$^{9d}$,
   $C_3$–$C_6$ cycloalkyl substituted with 0–3 R$^{9d}$,
   aryl substituted with 0–5 R$^{9d}$, and
   5–6 membered heterocyclic group consisting of carbon atoms and 1–4 heteroatoms selected from the group: O, S, and N, and said heterocyclic group is substituted with 0–4 R$^{9d}$;

$R^{9d}$ is selected at each occurrence from the group:
   H, F, Cl, Br, I, —NO$_2$, —CN, —NCS, —CF$_3$, —OCF$_3$, —CH$_3$,
   —OCH$_3$, =O, OH, —CO$_2$H, phenyl, —NH$_2$, —NH(CH$_3$), —N(CH$_3$)$_2$,
   —CO$_2$R$^{11}$, —C(=O)NR$^{11}$R$^{11}$, —NHC(=O)R$^{11}$, —NR$^{11}$R$^{11}$, —OR$^{11a}$, —SR$^{11a}$, —C(=O)R$^{11a}$,
   —S(=O)R$^{11a}$, —SO$_2$R$^{11}$, —SO$_2$NR$^{11}$R$^{11}$,
   $C_1$–$C_4$ alkyl, $C_1$–$C_4$ alkoxy, $C_1$–$C_4$ haloalkyl, and $C_1$–$C_4$ haloalkoxy;

$R^{11}$ is, at each occurrence, independently H or $C_1$–$C_4$ alkyl;

$R^{11a}$ is, at each occurrence, independently H, $C_1$–$C_4$ alkyl, aryl, or $C_1$–$C_4$ haloalkyl;

$R^{13}$ is H, methyl, ethyl, propyl, or butyl;

$A^4$ and $A^5$ are independently selected from an amino acid residue;

an amino acid residue, at each occurence, independently comprises Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

$R^{28}$ and $R^{29}$ are independently selected from:
H, methyl, ethyl, propyl, butyl, phenylmethyl-, phenylethyl-, phenylpropyl-, cyclopropyl, cyclobutyl, cyclopentyl, and cyclohexyl;

q is 0, 1 or 2.

5. A compound according to claim 4 of Formula (II):

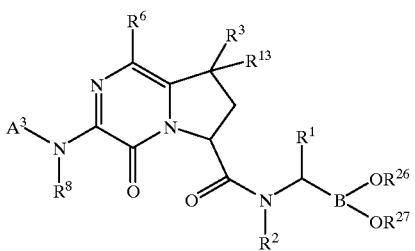

(II)

or a stereoisomer or pharmaceutically acceptable salt form thereof, wherein:

$A^3$ is —$R^9$ or —$A^4$—$R^9$;

$OR^{26}$ and $OR^{27}$ are independently selected from:
a) —OH,
b) —F,
c) $C_1$–$C_6$ alkoxy, or
when taken together, $OR^{26}$ and $OR^{27}$ form:
d) a cyclic boron ester where said chain or ring contains from 2 to 16 carbon atoms, and, optionally, 1, 2, or 3 heteroatoms which can be N, S, or O, $R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH,
—$CO_2R^{1b}$, —$SO_2R^{1b}$, —$SO_3R^{1b}$, —$P(O)_2R^{1b}$, —$P(O)_3R^{1b}$, —C(=O)NHR$^{1b}$, —NHC(=O)R$^{1b}$, —$SO_2NHR^{1b}$, —$OR^{1b}$, —$SR^{1b}$,
$C_1$–$C_3$ alkyl, $C_3$–$C_6$ cycloalkyl, $C_1$–$C_6$ alkoxy,
—S—($C_1$–$C_6$ alkyl),
aryl substituted with 0–5 $R^{1c}$,
—O—$(CH_2)_q$-aryl substituted with 0–5 $R^{1c}$,
—S—$(CH_2)_q$-aryl substituted with 0–5 $R^{1c}$,
5–10 membered heterocyclic group consisting of carbon atoms and 1–4 heteroatoms selected from the group: O, S, and N, and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocycle substituted with 0–5 $R^{1c}$,
aryl substituted with 0–5 $R^{1c}$,
5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from the group:
$C_1$–$C_4$ alkyl, Cl, F, Br, I, OH, $C_1$–$C_4$ alkoxy, —CN, —$NO_2$, —$OR^{1d}$, —C(=O)$OR^{1d}$, $NR^{1d}R^{1d}$, $CF_3$, $OCF_3$, and phenyl substituted with 0–3 $R^{1e}$;

$R^{1d}$ is H, methyl, ethyl, propyl, butyl, phenyl, or benzyl;

$R^{1e}$ is selected at each occurrence from the methyl, ethyl, Cl, F, Br, I, OH, methoxy, ethoxy, —CN, —$NO_2$, —C(=O)$OR^{1d}$, $NR^{1d}R^{1d}$, $CF_3$, and $OCF_3$;

$R^2$ is H, methyl, ethyl, propyl, butyl, or cyclopropyl;

$R^3$ is —$R^4$, —$NR^4R^5$, —$OR^4$, or —$SR^4$;

$R^4$ is selected from the group: H,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{10}$ cycloalkyl substituted with 0–4 $R^{4b}$,
aryl substituted with 0–5 $R^{4b}$,
5–10 membered heterocyclic group consisting of carbon atoms and 1–4 heteroatoms selected from the group: O, S, and N, and said heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_3$–$C_{10}$ cycloalkyl substituted with 0–4 $R^{4b}$,
aryl substituted with 0–5 $R^{4b}$, and
5–10 membered heterocyclic group consisting of carbon atoms and 1–4 heteroatoms selected from the group: O, S, and N, and said heterocyclic group is substituted with 0–3 $R^{4b}$;

$R^{4b}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_1$–$C_6$ alkyl substituted with 0–3 $R^{4c}$,
$C_2$–$C_6$ alkenyl substituted with 0–3 $R^{4c}$,
$C_2$–$C_6$ alkynyl substituted with 0–3 $R^{4c}$,
$C_3$–$C_6$ cycloalkyl substituted with 0–4 $R^{4d}$,
aryl substituted with 0–5 $R^{4d}$, and
5–6 membered heterocyclic group consisting of carbon atoms and 1–4 heteroatoms selected from the group: O, S, and N, and said heterocyclic group is substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_3$–$C_6$ cycloalkyl substituted with 0–4 $R^{4d}$,
aryl substituted with 0–5 $R^{4d}$,
5–6 membered heterocyclic group consisting of carbon atoms and 1–4 heteroatoms selected from the group:

O, S, and N, and said heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —$N(CH_3)_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ alkyl, $C_1$–$C_4$ alkoxy, $C_1$–$C_4$ haloalkyl, and $C_1$–$C_4$ haloalkoxy;

$R^5$ is selected from the group:
H, methyl, ethyl, propyl, butyl, phenyl, phenylmethyl-, phenylethyl-, cyclopropyl, cyclobutyl, cyclopentyl, cyclohexyl, cyclopropylmethyl-, cyclobutylmethyl-, cyclopentylmethyl-, cyclohexylmethyl-, cyclopropylethyl-, cyclobutylethyl-, cyclopentylethyl-, and cyclohexylethyl-;

$R^6$ is H, Cl, Br, or methyl;

$R^8$ is H, methyl, ethyl, or cyclopropyl;

$R^9$ is selected from the group: —S(=O)$R^{9a}$, —S(=O)$_2R^{9a}$, —C(=O)$R^{9a}$, —C(=O)O$R^{9a}$, —C(=O)NHR$^{9a}$, $C_1$–$C_3$ alkyl-$R^{9a}$, $C_2$–$C_6$ alkenyl-$R^{9a}$, and $C_2$–$C_6$ alkynyl-$R^{9a}$;

$R^{9a}$ is selected from the group: H
$C_1$–$C_6$ alkyl substituted with 0–3 $R^{9b}$,
$C_3$–$C_6$ cycloalkyl substituted with 0–3 $R^{9c}$ and
aryl substituted with 0–3 $R^{9c}$ and
5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group:
phenyl substituted with 0–3 $R^{9c}$,
naphthyl substituted with 0–3 $R^{9c}$,
benzyl substituted with 0–3 $R^{9c}$, and
5–10 membered heterocyclic group consisting of carbon atoms and 1–4 heteroatoms selected from the group: O, S, and N; and said heterocyclic group is substituted with 0–3 $R^{9c}$;

$R^{9c}$ is selected at each occurrence from the group:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —$N(CH_3)_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_1$–$C_4$ alkyl substituted with 0–3 $R^{9d}$,
$C_1$–$C_4$ alkoxy substituted with 0–3 $R^{9d}$,
$C_3$–$C_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —$N(CH_3)_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ alkyl, $C_1$–$C_4$ alkoxy, $C_1$–$C_4$ haloalkyl, and $C_1$–$C_4$ haloalkoxy;

$R^{11}$ is, at each occurrence, independently H or $C_1$–$C_4$ alkyl;

$R^{11a}$ is, at each occurrence, independently H, $C_1$–$C_4$ alkyl, aryl, or $C_1$–$C_4$ haloalkyl;

$R^{13}$ is H, methyl, ethyl, propyl, or butyl;

$A^4$ is selected from Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val; and q is 0, 1 or 2.

6. A compound according to claim 5 of Formula (II):

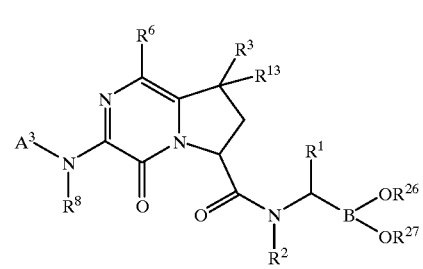

(II)

or a stereoisomer or pharmaceutically acceptable salt form thereof, wherein:

$A^3$ is —$R^9$;

$OR^{26}$ and $OR^{27}$ are independently selected from:
a) —OH,
b) —F,
c) methyloxy, ethyloxy, propyloxy, butyloxy, pentyloxy, or hexyloxy,
when taken together, $OR^{26}$ and $OR^{27}$ form:
d) a cyclic boron ester where said chain or ring contains from 2 to 12 carbon atoms, and, optionally, a heteroatom which can be N, S, or O;

$R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH,
—$CO_2R^{1b}$, —$SO_2R^{1b}$, —$SO_3R^{1b}$, —$P(O)_2R^{1b}$, —$P(O)_3R^{1b}$, —C(=O)NHR$^{1b}$, —NHC(=O)$R^{1b}$, —$SO_2NHR^{1b}$, —$OR^{1b}$, —$SR^{1b}$,
$C_1$–$C_3$ alkyl, $C_3$–$C_6$ cycloalkyl, $C_1$–$C_6$ alkoxy,
aryl substituted with 0–5 $R^{1c}$,
5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocycle substituted with 0–5 $R^{1c}$, aryl substituted with 0–5 $R^{1c}$, 5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{1c}$;

$R^{1c}$ is selected at each occurrence from the group:
$C_1$–$C_4$ alkyl, Cl, F, Br, I, OH, $C_1$–$C_4$ alkoxy, —CN, —$NO_2$, —$OR^{1d}$, —C(=O)$OR^{1d}$, $NR^{1d}R^{1d}$, $CF_3$, $OCF_3$, and phenyl substituted with 0–3 $R^{1e}$;

$R^{1d}$ is H, methyl, ethyl, propyl, butyl or phenyl;

$R^{1e}$ is selected at each occurrence from the group:
methyl, ethyl, Cl, F, Br, I, OH, methoxy, ethoxy, —CN, —$NO_2$, —C(=O)$OR^{1d}$, $NR^{1d}R^{1d}$, $CF_3$, and $OCF_3$;

$R^2$ is H;

$R^3$ is —$R^4$ or —$OR^4$;

$R^4$ is selected from the group: H,
$C_1$–$C_4$ alkyl substituted with 0–3 $R^{4a}$,
$C_2$–$C_4$ alkenyl substituted with 0–3 $R^{4a}$,
$C_2$–$C_4$ alkynyl substituted with 0–3 $R^{4a}$,
$C_3$–$C_6$ cycloalkyl substituted with 0–4 $R^{4b}$,
aryl substituted with 0–5 $R^{4b}$, 5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_3$–$C_6$ cycloalkyl substituted with 0–4 $R^{4b}$,
aryl substituted with 0–5 $R^{4b}$, and 5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4b}$;

$R^{4b}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_1$–$C_4$ alkyl substituted with 0–3 $R^{4c}$,
$C_2$–$C_4$ alkenyl substituted with 0–3 $R^{4c}$,
$C_2$–$C_4$ alkynyl substituted with 0–3 $R^{4c}$,
$C_3$–$C_6$ cycloalkyl substituted with 0–4 $R^{4d}$,
aryl substituted with 0–5 $R^{4d}$, and 5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —C(=NH)$NH_2$, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ haloalkyl, $C_1$–$C_4$ haloalkoxy,
$C_3$–$C_6$ cycloalkyl substituted with 0–4 $R^{4d}$,
aryl substituted with 0–5 $R^{4d}$, and 5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, —$CH_3$,
—$OCH_3$, =O, OH, —$CO_2H$, phenyl, —$NH_2$, —NH($CH_3$), —N($CH_3$)$_2$,
—$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
$C_1$–$C_4$ alkyl, $C_1$–$C_4$ alkoxy, $C_1$–$C_4$ haloalkyl, and $C_1$–$C_4$ haloalkoxy;

$R^6$ is H, Cl or Br;

$R^8$ is H;

$R^9$ is —S(=O)$_2R^{9a}$, —C(=O)$R^{9a}$, —C(=O)$NHR^{9a}$, —$CH_2$—$R^{9a}$, —$CH_2CH_2$—$R^{9a}$, or —$CH_2CH_2CH_2$—$R^{9a}$;

$R^{9a}$ is selected from the group: H
$C_1$–$C_6$ alkyl substituted with 0–3 $R^{9b}$,
$C_3$–$C_6$ cycloalkyl substituted with 0–3 $R^{9c}$ and
aryl substituted with 0–3 $R^{9c}$ and 5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 $R^{9c}$;

$R^{9b}$ is selected from the group:
  phenyl substituted with 0–3 $R^{9c}$,
  naphthyl substituted with 0–3 $R^{9c}$,
  benzyl substituted with 0–3 $R^{9c}$, and
  5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 $R^{9c}$;

$R^{9c}$ is selected at each occurrence from the group:
  H, F, Cl, Br, I, —$NO_2$, —CN, —NCS, —$CF_3$, —$OCF_3$, —$CH_3$,
  —$OCH_3$, =O, OH, —$CO_2H$, phenyl, —$NH_2$, —NH($CH_3$), —N($CH_3$)$_2$,
  —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
  $C_1$–$C_4$ haloalkyl, $C_1$–$C_4$ haloalkoxy,
  $C_1$–$C_4$ alkyl substituted with 0–3 $R^{9d}$,
  $C_1$–$C_4$ alkoxy substituted with 0–3 $R^{9d}$,
  $C_3$–$C_6$ cycloalkyl substituted with 0–3 $R^{9d}$,
  aryl substituted with 0–5 $R^{9d}$, and
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{9d}$;

$R^{9d}$ is selected at each occurrence from the group:
  H, F, Cl, Br, I, —$NO_2$, —CN, —NCS, —$CF_3$, —$OCF_3$, —$CH_3$,
  —$OCH_3$, =O, OH, —$CO_2H$, phenyl, —$NH_2$, —NH($CH_3$), —N($CH_3$)$_2$,
  —$CO_2R^{11}$, —C(=O)$NR^{11}R^{11}$, —NHC(=O)$R^{11}$, —$NR^{11}R^{11}$, —$OR^{11a}$, —$SR^{11a}$, —C(=O)$R^{11a}$, —S(=O)$R^{11a}$, —$SO_2R^{11}$, —$SO_2NR^{11}R^{11}$,
  $C_1$–$C_4$ alkyl, $C_1$–$C_4$ alkoxy, $C_1$–$C_4$ haloalkyl, and $C_1$–$C_4$ haloalkoxy;

$R^{11}$ is, at each occurrence, independently H, methyl, ethyl propyl, or butyl;

$R^{11a}$ is, at each occurrence, independently H, methyl, ethyl propyl, butyl, phenyl, naphthyl, or trifluoromethyl;

$R^{13}$ is H, methyl, ethyl, propyl, or butyl; and q is 0, 1 or 2.

7. A compound according to claim 6 of Formula (IIa):

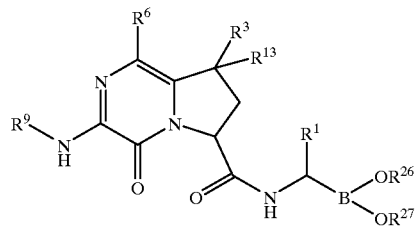

(IIa)

or a stereoisomer or pharmaceutically acceptable salt form thereof, wherein:

$OR^{26}$ and $OR^{27}$ are independently selected from:
  a) —OH,
  b) —F,
  c) methyloxy, ethyloxy, propyloxy, butyloxy, pentyloxy, or hexyloxy, and
  when taken together, $OR^{26}$ and $OR^{27}$ form:
  d) pinandiol, pinacol, 1,2-ethanediol, 1,2-propanediol, 1,3-propanediol, 2,3-butanediol, 1,2-diisopropylethanediol, 5,6-decanediol, or 1,2-dicyclohexylethanediol;

$R^1$ is selected from the group:
  —$CH_2CH_3$, —$CH_2CH_2CH_3$, —$CH(CH_3)_2$, —$CH_2CH_2CH_2CH_3$, —$CH_2CH(CH_3)_2$, —$CH_2C(CH_3)_3$, —$CH_2CH_2C(CH_3)_3$, —$CH_2CH_2CH_2C(CH_3)_3$, —$CH_2CH_2CH_2CH(CH_3)_2$, —$CH_2CH_2CH_2CH(CH_2CH_3)_2$, —$CH_2CH_2CH_2CH_2CH_3$, —$CH_2CH_2CH(CH_3)_2$, —$CH_2CH_2CH_2CH_2CH_2CH_3$, —$CH_2CF_3$, —$CH_2CH_2CF_3$, —$CH_2CH_2CH_2CF_3$, —$CH_2CHF_2$, —$CH_2CH_2CHF_2$, —$CH_2CH_2CH_2CHF_2$, —CH=$CH_2$, —$CH_2$CH=$CH_2$, —CH=CH$CH_3$, cis-$CH_2$CH=CH($CH_3$), trans-$CH_2$CH=CH($CH_3$), —$CH_2CH_2$CH=CH, —$CH_2$CH=C($CH_3$)$_2$, —$CH_2CH_2$CH=C($CH_3$)$_2$, —$CH_2CO_2H$, —$CH_2CH_2CO_2H$, —$CH_2CO_2C(CH_3)_3$, —$CH_2CH_2CO_2C(CH_3)_3$, —$CH_2CH_2CH_2CH_2NH_2$,
  phenyl, benzyl, phenethyl, phenpropyl, phenbutyl, (2-methylphenyl)ethyl-, (3-methylphenyl)ethyl-, (4-methylphenyl)ethyl-, (4-ethylphenyl)ethyl-, (4-i-propylphenyl)ethyl-, (4-t-butylphenyl)ethyl-, (4-hydroxyphenyl)ethyl-, (4-phenyl-phenyl)ethyl-, (4-phenoxy-phenyl)ethyl-, (4-cyclohexyl-phenyl)ethyl-, (4-cyclopropyl-phenyl)ethyl-, (2,5-dimethylphenyl)ethyl-, (2,4-dimethylphenyl)ethyl-, (2,6-difluorophenyl)ethyl-, (4-cyclopentyl-phenyl)ethyl-, (4-cyclobutyl-phenyl)ethyl-, (2-trifluoromethylphenyl)ethyl-, (3-trifluoromethylphenyl)ethyl-, (4-trifluoromethylphenyl)ethyl-, (2-fluorophenyl)ethyl-, (3-fluorophenyl)ethyl-, (4-fluorophenyl)ethyl-, (2-chlorophenyl)ethyl-, (3-chlorophenyl)ethyl-, (4-chlorophenyl)ethyl-, (2-bromophenyl)ethyl-, (3-bromophenyl)ethyl-, (4-bromophenyl)ethyl-, (2,3,4,5,6-pentafluorophenyl)ethyl- (naphth-2-yl)ethyl, (cyclobutyl)methyl, (cyclobutyl)ethyl, (cyclobutyl)propyl, cyclopropyl, cyclobutyl, cyclopentyl, and cyclohexyl;

$R^3$ is selected from the group:
  methyl, ethyl, propyl, butyl, pentyl, hexyl, phenylmethyl, phenylethyl, phenylpropyl, (cyclopropyl)methyl, (cyclopropyl)ethyl, (cyclopropyl)propyl, (cyclohexyl)methyl, (cyclohexyl)ethyl, (cyclohexyl)propyl, (3-methylphenyl)methyl-, (4-methylphenyl)methyl-, (3-CF$_3$-phenyl)methyl-, (4-CF$_3$-phenyl)methyl-, (3-methoxyphenyl)methyl-, (4-methoxyphenyl) methyl-, phenylmethyl-O-, phenylethyl-O-, (naphth-1-yl)methyl-O-, and (naphth-2-yl)methyl-O-;

R$^6$ is H or Cl;

R$^9$ is selected from the group:
methyl, ethyl, propyl, butyl, pentyl, hexyl, trifluoromethyl, phenylmethyl, phenylethyl, phenylpropyl, (3-phenyl-phenyl)methyl-, (4-phenyl-phenyl)methyl-, (2-methylphenyl)methyl-, (3-methylphenyl)methyl-, (4-methylphenyl)methyl-, (2-fluorophenyl)methyl-, (3-fluorophenyl)methyl-, (4-fluorophenyl)methyl-, (2-chlorophenyl)methyl-, (3-chlorophenyl)methyl-, (4-chlorophenyl)methyl-, (2-bromophenyl)methyl-, (3-bromophenyl)methyl-, (4-bromophenyl)methyl-, (2-cyanophenyl)methyl-, (3-cyanophenyl)methyl-, (4-cyanophenyl)methyl-, (2-nitrophenyl)methyl-, (3-nitrophenyl)methyl-, (4-nitrophenyl)methyl-, (2-aminophenyl)methyl-, (3-aminophenyl)methyl-, (4-aminophenyl)methyl-, (2-CF$_3$SO$_2$-phenyl)methyl-, (3-CF$_3$SO$_2$-phenyl)methyl-, (4-CF$_3$SO$_2$-phenyl)methyl-, (2-CF$_3$-phenyl)methyl-, (3-CF$_3$-phenyl)methyl-, (4-CF$_3$-phenyl)methyl-, (2-methoxyphenyl)methyl-, (3-methoxyphenyl)methyl-, (4-methoxyphenyl) methyl-, (2-CF$_3$O-phenyl)methyl-, (3-CF$_3$O-phenyl) methyl-, (4-CF$_3$O-phenyl)methyl-, (2-CF$_3$S-phenyl) methyl-, (3-CF$_3$S-phenyl)methyl-, (4-CF$_3$S-phenyl) methyl-, (3,5-diCF$_3$-phenyl)methyl-, (3,4-diCF$_3$-phenyl)methyl-, (3,5-diCl-phenyl)methyl-, (2,5-diCl-phenyl)methyl-, (3,4-diCl-phenyl)methyl-, (3,5-diF-phenyl)methyl-, (2,5-diF-phenyl)methyl-, (3,4-diF-phenyl)methyl-, (2-furanyl)methyl-, (3-furanyl)methyl-, (2-pyridyl)methyl-, (3-pyridyl) methyl-, (4-pyridyl)methyl-,(1,3-benzodioxolo-5-yl) methyl-, (cyclopropyl)methyl-, (cyclobutyl)methyl-, (cyclopentyl)methyl-, and (cyclohexyl)methyl-;

R$^{11}$ is, at each occurrence, independently H, methyl, ethyl propyl, or butyl;

R$^{11a}$ is, at each occurrence, independently H, methyl, ethyl propyl, butyl, or trifluoromethyl;

R$^{13}$ is H or methyl; and q is 0, 1 or 2.

8. A compound according to claim 7, wherein the compound is selected from the group:

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[4-methoxyphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2,5-difluorophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-methylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-(trifluoromethyl)thiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3,4-difluorophenyl]methyl]amino]-pyrrolo[1,2-a]pyrazine-6-carboxamide;

(6S, 8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3,5-bis(trifluoromethyl)phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[1,3-benzodioxolo-5-methyl]amino]-pyrrolo[1,2-a]pyrazine-6-carboxamide;

(6S, 8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-phenylpropyl)-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-biphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-nitro-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2-furanyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[1-hexyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[(methyl)amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[phenylmethyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-fluoro-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-chloro-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-methoxy-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[4-methoxy-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-cyano-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-benzyl-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-naphthylmethyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-dimethylethylbenzyl)-3-[[[3-trifluromethyl-phenyl]methyl]amino]-pyrrolo[1,2-a pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-methylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(4-trifluoromethylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-benzyl-3-[[[3-cyano-phenyl]methyl]amino]-pyrrolo(1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-methylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3,5-dimethylbenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-methoxybenzyl)-3-[[[3-trifluromethyl-phenyl]methyl]amino]-pyrrolo[1,2-a]pyrazine-6-carboxamide;

(6S)-1-chloro-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8,8-dimethyl-4-oxo-3-[[[3-(trifluoromethyl)phenyl]methyl]amino]pyrrolo[1,2-a]pyrazine-6-carboxamide;

(6S,8R)-1-chloro-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S,8S)-1-chloro-N-[(1R)-1-[(3aS,4S,6S,7aR)-Hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S)-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8,8-dimethyl-4-oxo-3-[[[3-(trifluoromethyl)phenyl]methyl]amino]pyrrolo[1,2-a]pyrazine-6-carboxamide;

(6S,8R)-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S,8S)-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-8-methyl-4-oxo-8-(3-phenylpropyl)-3-[[[3-(trifluoromethyl)phenyl]methyl]amino]pyrrolo[1,2-a]pyrazine-6-carboxamide;

(6S)-1-chloro-N-[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-4-oxo-8,8-di(3-phenylpropyl)-3-[[[3-(trifluoromethyl)phenyl]methyl]amino]pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-naphthylmethoxy)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-(4-trifluoromethylphenylethyl)]-1-chloro-4,6,7,8-tetrahydro-4-oxo-8-(3-methoxybenzyl)-3-[[[3-trifluromethyl-phenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-(2-naphthyl)propyl)-3-[[[3-trifluromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-ethyl]-1-chloro-4,6,7,8-tetrahydro-4-oxo-8-(3-(2-naphthyl)propyl)-3-[[[3-trifluromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-(2-naphthyl)propyl)-3-[[[3-trifluromethylthiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-ethyl]-1-chloro-4,6,7,8-tetrahydro-4-oxo-8-(3-(2-naphthyl)propyl)-3-[[[3-trifluromethylthiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-(2-naphthyl)propyl)-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-[2,2-difluoroethyl]]-1-chloro-4,6,7,8-tetrahydro-4-oxo-8-(3-(2-naphthyl)propyl)-3-[[[3-trifluoromethylthiophenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[2-propyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-(2-methylpropyl)amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-(cyclohexylmethyl)amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-trifluoromethoxyphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2-difluoromethoxyphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[2-pyridinyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[4-pyridinyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-8-(3-phenylpropyl)-3-[[[3-pyridinyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[5-methyl-2-pyrazinyl)methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-4,6,7,8-tetrahydro-4-oxo-3-[[[3-trifluoromethylphenyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[[tert-butoxylcarbonyl]methyl]amino]-pyrrolo[1,2-a]pyrazine-6-carboxamide;

(6S,8R)-N-[[(1R)-1-[(3aS,4S,6S,7aR)-hexahydro-3a,5,5-trimethyl-4,6-methano-1,3,2-benzodioxaborol-2-yl]-3-butenyl]-1-chloro-4,6,7,8-tetrahydro-4-oxo-3-[[(2-tert-butoxylcarbonyl)ethyl]amino]-pyrrolo[1,2-a]pyrazine-6-carboxamide;

[(1R)-1-[[[(6S,8R)-1-chloro-4,6,7,8-tetrahydro-4-oxo-8-(3-phenylpropyl)-3-[[[3-(trifluoromethyl)phenyl]methyl]-amino]pyrrolo[1,2-a]pyrazin-6-yl]carbonyl]amino]-3-butenyl]-boronic acid;

[(1R)-1-[[[(6S, 8R)-1-chloro-4, 6,7,8-tetrahydro-4-oxo-8-[3-(2-naphthyl)propyl]-3-[[[3-(trifluoromethyl)phenyl]methyl]-amino]pyrrolo[1,2-a]pyrazin-6-yl]carbonyl]amino]-3-butenyl]-boronic acid; and

[(1R)-1-[[[(6S,8R)-1-chloro-4,6,7,8-tetrahydro-4-oxo-8-[3-(2-naphthyl)propyl]-3-[[[3-(trifluoromethyl)phenyl]methyl]amino]pyrrolo[1,2-a]pyrazin-6-yl]carbonyl]amino]-3-ethyl]-boronic acid.

9. A pharmaceutical composition comprising a pharmaceutically acceptable carrier and a therapeutically effective amount of a compound of claim 1 or a pharmaceutically acceptable salt form thereof.

10. A method of treating HCV infection which comprises administering to a host in need of such treatment a therapeutically effective amount of a compound of claim 1 or a pharmaceutically acceptable salt form thereof.

* * * * *